United States Patent
Harman et al.

(10) Patent No.: US 11,477,952 B2
(45) Date of Patent: Oct. 25, 2022

(54) ENDOPHYTIC MICROBIAL SEED TREATMENT FORMULATIONS AND METHODS RELATED THERETO FOR IMPROVED PLANT PERFORMANCE

(71) Applicant: ADVANCED BIOLOGICAL MARKETING, INC., Geneva, NY (US)

(72) Inventors: Gary Harman, Geneva, NY (US); Andrea Shelley Marino, Geneva, NY (US); Molly Cadle-Davidson, Geneva, NY (US)

(73) Assignee: ADVANCED BIOLOGICAL MARKETING, INC., Geneva, NY (US)

( * ) Notice: Subject to any disclaimer, the term of this patent is extended or adjusted under 35 U.S.C. 154(b) by 0 days.

(21) Appl. No.: 16/171,203

(22) Filed: Oct. 25, 2018

(65) Prior Publication Data

US 2019/0174692 A1 Jun. 13, 2019

Related U.S. Application Data

(60) Provisional application No. 62/576,684, filed on Oct. 25, 2017.

(51) Int. Cl.
| | | |
|---|---|---|
| *A01H 3/00* | (2006.01) | |
| *B08B 9/045* | (2006.01) | |
| *A01N 63/38* | (2020.01) | |
| *A01N 63/22* | (2020.01) | |

(52) U.S. Cl.
CPC ............ *A01H 3/00* (2013.01); *A01N 63/22* (2020.01); *A01N 63/38* (2020.01); *B08B 9/045* (2013.01)

(58) Field of Classification Search
None
See application file for complete search history.

(56) References Cited

U.S. PATENT DOCUMENTS

| | | | |
|---|---|---|---|
| 6,808,917 B1 | 10/2004 | Johnson | |
| 8,716,001 B2 * | 5/2014 | Harman | C12R 1/885 435/252 |
| 8,877,480 B2 * | 11/2014 | Harman | A01N 63/30 435/252 |
| 8,877,481 B2 * | 11/2014 | Harman | C12R 1/885 435/252 |
| 9,249,061 B2 * | 2/2016 | Harman | C05C 9/00 |
| 2002/0103083 A1 | 8/2002 | Harman | |
| 2005/0096225 A1 | 5/2005 | Johnson | |
| 2008/0318777 A1 | 12/2008 | Lin et al. | |
| 2014/0323297 A1 | 10/2014 | Harman | |
| 2016/0186273 A1 | 6/2016 | Taghavi et al. | |

FOREIGN PATENT DOCUMENTS

| | | | |
|---|---|---|---|
| CN | 105733975 A | 7/2016 | |
| CN | 106754537 A | 5/2017 | |
| WO | WO9520879 A2 | 8/1995 | |
| WO | WO2010091337 A1 | 8/2010 | |
| WO | WO2011032281 A1 | 3/2011 | |
| WO | WO-2013078365 A1 * | 5/2013 | ............ C12P 21/06 |
| WO | WO2015013558 A1 | 1/2015 | |
| WO | 2017192117 A1 | 11/2017 | |
| WO | 2018183976 A1 | 10/2018 | |
| WO | 2018183977 A1 | 10/2018 | |

OTHER PUBLICATIONS

Yedidia et al. Induction of defense responses in cucumber plants (*Cucumis sativus* L.) by the biocontrol agent trichoderma harzianum. Appl. Environ. Microbiol. Mar. 1999;65(3):1061-70. (Year: 1999).*
Vinale et al. Trichoderma secondary metabolites that affect plant metabolism. Nat. Prod. Commun. Nov. 2012;7(11):1545-50. (Year: 2012).*
International Preliminary Report on Patentability regarding related PCT App. No. PCT/US2018/057592; dated Apr. 28, 2020.
Adi, S. 2016. Rhizosphere, food security, and climate change: a critical role for plant-soil research. Rhtzopshere 1:1-3.
Alfano, G., Lewis Ivey, M. L., Cakir, C., Bos, J. I. B., Miller, S. A., Madden, L. V., Kamoun, S., and Hoitink, H. A. J. 2007. Systemic modulation of gene expression in tomato by Trichoderma harzianum 382. Phytopathology 97:429-437.
Blaser, M. J., Cardon, Z. C., Cho, M. K., Dangl, J. L., Donohue, T. J., Green, J. L., Knight, R., Maxon, M. E., Northen, T. R., Pollard, K. S., and Brodie, E. L. 2016. Toward a predictive understanding of Earth's microbiomes to address 21st century challenges. mBio 7:e00714-00716.

(Continued)

*Primary Examiner* — Cynthia E Collins

(74) *Attorney, Agent, or Firm* — Reising Ethington P.C.

(57) ABSTRACT

This invention describes discovery and development of a biological system of plant growth promotion and environmental improvement by carbon sequestration and/or nitrogen utilization by application of a microbial agent, e.g., a highly effective strain of *T. viride*, particularly strains NRRL B-50520 and/or K5. This strain outperforms the best current strains of *Trichoderma* used for this purpose available commercially. The highly active products also are expected to increase plant productivity and improve quality of fruits, vegetables, flowers or other plant products. The invention also describes and demonstrates that strain combinations including *Bacillus amyloliquifaciens* AS2 or AS3, as well as disclosed metabolites, promote plant growth. This is true across monocots and dicots, seed treatments and foliar sprays. In the field plant height, shoot weight, root weight, and photosynthesis (Spad meter readings) were all increased in comparison to the untreated control as well as the leading biological seed treatments. The invention also describes metabolite utilization for enhancing plant growth.

6 Claims, 26 Drawing Sheets

(56) References Cited

OTHER PUBLICATIONS

Calvo, P., Watts, D. B., Kioepper, J. W., and Torbert, H. A. 2016. The influence of microbial-based inoculants on N2O emissions from soil planted with corn (Zea mays L.) under greenhouse conditions with different nitrogen fertilizer regimens. Canadian Journal of Microbiology 62:1041-1056.

Cawoy, H., Mariutto, M., Henry, G., Fisher, C., Vasilyeva, N., Thonart, P., Dommes, J., and Ongena, M. 2014. Plant Defense Stimulation by Natural Isolates of Bacillus Depends on Efficient Surfactin Production. Molecular Plant-Microbe Interactions 27:87-100.

Chaverri, P., Casttebury, L. A., Samuels, G. J., and Geiser, D. M. 2002. Multilocus phyiogentic structure of Trichoderma harzianum/Hypocrea lixii complex. Molec. Phylogen. and Evol. Submitted.

Committee on Geoengineering Climate, B. o. A. S. a. C., Ocean Studies Board, National Research Council. 2015. Climate Intervention: Carbon Dioxide Removal and Reliable Sesquestration. National Academies Press, Washington DC.

Djonovic, S., Pozo, M. J., Dangott, L. J., Howell, C. R., and Kenertey, C. M. 2006. Sm1, a proteinaceous elicitor secreted by the bioconfrol fungus Trichoderma vlrens induces plant defense responses and systemic resistance. Molec. Plant Microbe Interact. 8:838-853.

Doni, F., Zain, C. R. C. M., Isahak. A., Faturrahaman, F., Anhar, A., Mohamad, W., Yusoff, W. M. W., and Uphoff, N. 2017. A simple, efficient, and farmer-friendly Trichoderma-based biofertilizer evaluated with the SRI rice management system. Organic Agric. In press.

Ertani, A., Francioso, O., Tugnoil, V., Right, V., and Nardi, S. 2011. Effect of Commercial Lignosulfonate-Humate on Zea mays L. Metabolism. Journal of Agricultural and Food Chemistry 59:11940-11948.

Feofilova, E. P. 2010. The fungal cell wall: Modern concepts of its composition and biological function. Microbiology 79:711-720.

Gopal, M., and Gupta, A. 2016. Microbiome selection could spur next-generation plant breeding strategies. Front. in Micrbiol. 7:1971.

Guanter, L., Zhang, Y., Jung, M., Joiner, J., Voigt, M., Berry, J. A, Frankenberg, C., Huete, A. R., Zarco-Tejada, P., Lee, J.-E., Moran, M. S., Ponce-Campos, G., Beer. C., Camps-Valls, G., Buchmann, N., Gianelle, D., Klumpp, K., Cescatti, A., Baker, J. M., and Griffis, T. J. 2014. Global and time-resolved monitoring of crop photosynthesis with chlorophyll fluorescence. Proceedings of the National Academy of Sciences of the United States of America 111:E1327-E1333.

Guler, N. S., Pehlivan, N., Karaoglu, S. A., Guzel, S., and Bozdeveci, A. 2016. Trichoderma atroviride ID20G inoculation ameliorates drought stress-induced damages by improving antioxidant defence in maize seedlings. Acta Physiologiae Plantarum 38:132.

Han, H. S., and Lee, K. D. 2005. Plant growth promoting rhizobacteria effects on antioxidant status, photosynthesis, mineral uptake and growth of lettuce under soil salinity. Res. J. Agric. Biol. Sci. 1:205-215.

Hansen, J., Satio, M., Kharecha, P., von Schukmann, K., Beerling, D. J., Cao, J., Marcott, S., Masson-Delmotte, V., Prather, M. J., Rohling, E. J., Shakun, J., and Smith, p. 2016, Young People's Burden: Requirement of negative CO2 emissions. Earth Syst. Dynamic.Discussion.

Harman, G. E. 2000. Myths and dogmas of biocontrol. Changes in perceptions derived from research on Trichoderma harzianum T-22. Plant Dis. 84:377-393.

Harman, G. E., Petzoldt, R., Comis, A., and Chen, J. 2004a. Interactions between Trichoderma harzianum strain vinT22 and maize inbred line Mo17 and effects of these interactions on diseases caused by Pythium ultimum and Colletotrichum graminicola. Phytopathology 94:147-153.

Harman, G. E., Howell, C. R., Viterbo, A., Chet, I., and Lorito, M. 2004b. Trichoderma species—opportunistic, avirutent piant symbionts. Nature Rev. Microbiol. 2:43-56.

Jaskiewicz, M., Conrath, U., and Peterhaensel, C. 2011. Chromatin modification acts as a memory for systemic acquired resistance in the plant stress response. EMBO Reports 12:50-55.

Kane, D. 2015. Carbon sequestration potential on agricultural lands: A review of current science and available practices. National Sustainable Agriculture Coalition. Breakthrough Strategies and Solutions LLC.

Kell, D. B. 2012. Large-scale sequestration of atmospheric carbon via plant roots in natural ecosystems: why and how. Philosophical Transactions of the Royal Society of London B Biological Sciences 367-1597:1589-1597.

Lal, R. 2004, Soil carbon sequestration impacts on global climate change and food security. Science 304:1623-1627.

Long, S. P., Marshall-Colon, A., and Zhu, X.-G. 2015 Meeting the global food demand of the future by engineering crop photosynthesis and yield potential. Cell 161:56-66.

Lorito, M., Woo, S. L., Hannan, G. E., and Monte, E. 2010. Translational research on Trichoderma: from 'omics to the field, Annu. Rev. Phytopathol. 48:395-417.

Marra, R., Ambrosino, P., Carbone, V., Vinale, F., Woo, S. L., Ruocco, M., Ciiiento, R., Lanzuise, S., Ferraioli, S., Soriente, I., Turrà, D., Fagliano, V., Scala, F., and Lorito, M. 2006. Study of the three-way interaction between Trichoderma atroviride, plant and fungal pathogens using a prateome approach. Curr. Genet. 50:307-321.

Mastouri, F. 2010. Use of Trichoderma spp. to improve plant performance under abiotic stress, PhD. Cornell University, Ithaca, NY.

Mastouri, F., Bjorkman, T., and Harman, G. E. 2010. Seed treatments with Trichoderma harzianum alleviate biotic, abiotic and physiological stresses in germinating seeds and seedlings. Phytopathology 100:1213-1221.

Mastouri, F., Bjorkman, T., and Harman, G. E. 2012. Trichoderma harzianum strain T22 enhances antioxidant defense of tomato seedlings and resistance to water deficit. Molec. Plant Microbe Interact. 25:1264-1271.

Mo, Y., Wang, Y., Yang, R., Zheng, J., Liu. C., Li, H., Ma, J., Zhang, Y., Wei, C., and Zhang, X. 2016. Regulation of plant growth, photosynthesis, antioxidation and osmosis by an arbuscular mycorrhizal fungus in watermelon seedlings under well-watered and drought conditions. Frontiers in Plant Science 7.

Morath, S. U., Hung, R., and Bennett, J. W. 2012. Fungal volatile organic compounds: A review with emphasis on their biotechnological potential Fungal Biol. Rev. 26:73-83.

Nath, K., Jajoo, A., Poudyal, R. S., Timilsina, R., Park, Y. S., Ara, E.-M., G., N. H., and Lee, C.-H. 2013. Towards a critical understanding of the photosystem II repair mechanism and it regulation under stress conditions. FEBS Letters 587:3372-3381.

Pascale, A., Vinale, F., Manganiello, G., Nigro, M., Lanzuise, S., Ruocco, Marra, R., Lombardi, N., Woo, S. L., and Lorito, M. 2017. Trichoderma and its secondary metabolites improve yield and quality of grapes. Crop Protection 92:176-181.

Paustian, K., Campell, N., Dorich, C., Marx, E., and Swan, A. 2016. Assessment of potentiai greenhouse gas mitigation from changes to crop root management and architecture. Booz Allen Hamilton Inc., Washington DC.

Samuels, G. J., and Hebbar, P. K. 2015. Trichoderma. Identification and Agricultural Properties. The American Phytopathological Society, St. Paul MN.

Shoresh, M., and Harman, G. E. 2008a. The relationship between increased growth and resistance induced in plants by root colonizing microbes. Plant Signal. Behavior 3:737-739.

Shoresh, M., and Harman, G. E. 2008b. The molecular basis of maize responses to Trichoderma harzianum T22 inoculation: a proteomic approach. Plant Physiol. 147:2147-2163.

Shoresh, M., Mastouri, F., and Harman, G. E. 2010. Induced systemic resistance and plant responses to fungal biocontrol agents. Annu. Rev. Phytopathol. 48:21-43.

Thompson, K. A., Bent, E., Abates, D., Wagner-Riddle, C., and Dunfleid, K. E. 2016. Soil microbial communities as potential regulators of in situ N2O fluxes in annual and perennial cropping systems. Soil Biology & Biochemistry 103:262-273.

(56) References Cited

OTHER PUBLICATIONS

Vargas, W. A., Mandawe, J. C., and Kenerley, C. M. 2009. Plant-derived sucrose is a key element in the symbiotic association between Trichoderma virens and maize plants. Plant Physiol 151:792-808.

Walter, F., Achate, B., Baltruschat, H., Fodor, J., Becker, K., Fischer, M., Heier, T., Hueckelhoven, R., Neumann, C., von Wettstein, D., Franken, P., and Kogel, K.-H. 2005. The endophytic fungus Piriformospora indica reprograms barley to salt-stress tolerance, disease resistance, and higher yield. PNAS 102:13386-13391.

Xu, S., Fu, X., Ma, S., Bai, Z., Xiao, R., Li, Y., and Zhuang, G. 2014. Mitigating Nitrous Oxide Emissions from Tea Field Soil Using Bioaugmentation with a Trichoderma viride Biofertiltzer. Scientific World Journal:793752.

Yedidia, I., Benhamou, N., and Chet, I. 1999 induction of defense responses in cucumber plants (*Cucumis sativus* L.) by the bioconfrol agent Trichoderma harzianum. Appl. Environ. Microbiol. 65:1061-1070.

Zachow, C., Berg, C., Mulller; H., Monk, J., and Berg, G. 2016. Endemic plants harbor specific Trichoderma communities with an exceptional potential for biocontrol of phtopathogens. J. Biotechnol. In press (http://dx.doi.org/10.1016/j.biotec.2016.03.049)).

Zibilske, L. M., and Materon, L. A. 2005. Biochemical properties of decomposing cotton and corn stem and root residues. Soil Science Society of America Journal 69:378-386.

Hatman, G. E., and Mastouri, F. 2010. Enhancing nitrogen use efficiency in wheat using Trichoderma seed inoculants. p. 4 in: Biology of Plant-Microbe Interactions, vol. 7. H. Antoun, T. Avis, L. Brisson, D. Prevost and M. Trepanier, eds. International Society for Plant-Microbe intereactons. St. Paul. MN.

Brazilian Office Action for BR Application No. 112020008227.9 dated Aug. 16, 2022 (3 pages).

\* cited by examiner

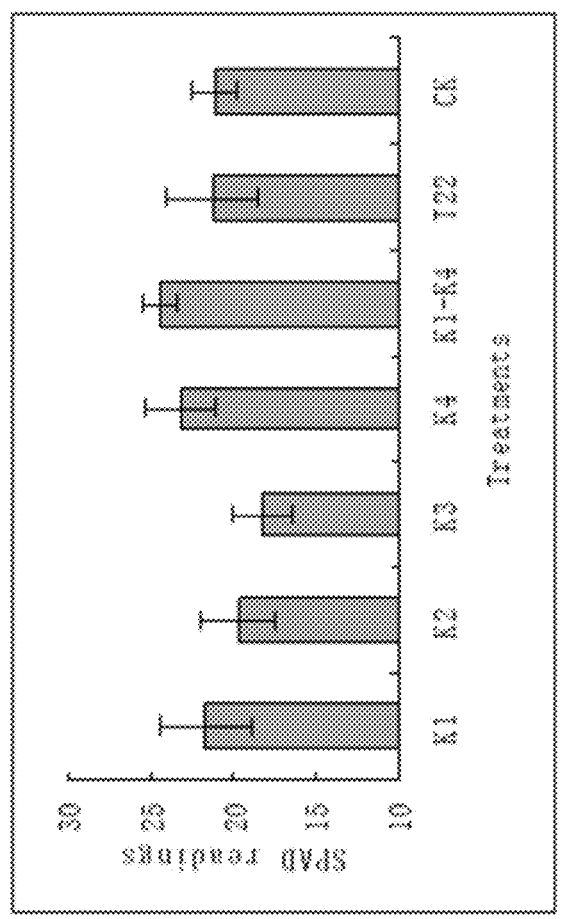
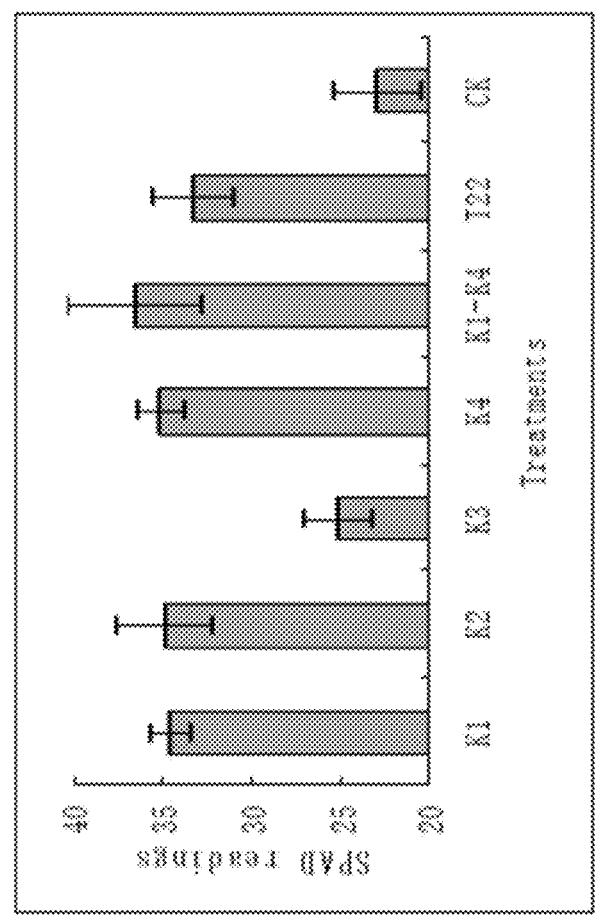
FIG. 21A
FIG. 21B

ENDOPHYTIC MICROBIAL SEED TREATMENT FORMULATIONS AND METHODS RELATED THERETO FOR IMPROVED PLANT PERFORMANCE

CROSS-REFERENCE TO RELATED APPLICATIONS

This application claims priority to U.S. Provisional Patent Application Ser. No. 62/576,684, filed on Oct. 25, 2017, entitled "Improving Plant Performance with Endophytic Microbial Seed Treatment Formulations: Making Better Holobionts" of which is hereby incorporated herein by reference in their entirety for all purposes.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

STATEMENT REGARDING FEDERALLY SPONSORED RESEARCH OR DEVELOPMENT

None.

REFERENCE TO SEQUENCE LISTING, TABLE, OR COMPUTER PROGRAM LISTING

Not Applicable

TECHNICAL FIELD

The present invention relates generally to discovery, development and gainful modification of plant systems, which impart plant growth promotion by a variety of mechanisms using multiple modalities, while supporting environmental stability by carbon sequestration.

BACKGROUND OF THE DISCLOSURE

The following description is provided to assist the understanding of the reader. None of the information provided or references cited is admitted to be prior art.

The plant root biome is a complex interactive system that includes root associated microbes, soil associated microbes, the plant root and other organisms. Some microbes, such as *Trichoderma* spp., have been known and suggested for decades as agents for control of plant pathogenic microbes (Weindling, 1932, Weindling and Fawcett, 1936). Since that time, understanding and use of these fungi and others has been the subject large and evolving body of knowledge (Harman, 2000, Harman, 2011, Harman, Howell, et al., 2004). Originally, as suggested by authors such as Weindling, the biocontrol abilities of these organisms was expected to occur as a consequence of mycoparasitism, antibiosis (Weindling, 1932, Weindling and Emerson, 1936, Weindling and Fawcett, 1936), and simply competition. Significant advances included the discovery of the abilities of very specific strains to be rhizosphere competent, i.e., to be able to colonize, persist and grow with roots to provide long-term benefits (Ahmad, 1987, Sivan and Harman, 1991). Beyond this, some strains were shown to penetrate and become established asymptomatically in root cortical cells. These strains induced the plant to wall off and limit the organism to the first few layers of root cells (Yedidia, Benhamou, et al., 1999). This was accompanied by signaling to the plant to provide induced systemic resistance via a priming type mechanism (Yedidia, Benhamou, et al., 2000, Yedidia, Shoresh, et al., 2003). MAPK signaling was required for the systemic effect (Shoresh, Gal-on, et al., 2006). The ability of certain selected strains to become established internally in roots, grow with roots and induce systemic changes in the plant we define as endophytic and rhizospheric competence. This capability is associated with induction of large changes in plant gene and protein expression, with the greatest changes occurring in the above ground parts of the plants even though the competent strains are located only on roots (Shoresh and Harman, 2008).

SUMMARY

Field and greenhouse studies were conducted with endophytic rhizosphere competent *Trichoderma* strains or one of their metabolites, 1-octen-3-ol, that were applied as seed treatments to corn. In some cases, they were co-applied with a strain of *Bacillus amyloliquifaciens* and/or adjuvant materials. The *Trichoderma* strains, as exemplified by *T. afroharzianum* strain K2, were demonstrated to colonize radicles of germinating corn seeds rapidly. All of the strains colonized roots of corn and soybeans endophytically, but they were restricted to roots and did not colonize above-ground plant parts or seeds. In field trials over three years, the microbial and biorational treatments provided increases in plant growth of both shoots and roots, and increased silage and grain yields in most cases, but for silage, yields of commercial hybrids developed as dual purpose silage and grain gave larger responses than those bred only for grain production. Cultural practices, especially N levels, affected yields of both grain and silage. Roots grown from treated seeds were larger and deeper than those of control plants. The percentage of C, N and other nutrients in harvested silage did not change as a consequence of the seed treatments. However, total levels on a per hectare basis were substantially increased by as much as 12 T/C ha. This increase in C is expected to reflect total photosynthetic capabilities of the plants and to represent C sequestration from the atmosphere. N and other nutrients also increased but must have been taken up by roots from the soil. Remarkably, even very small amounts of the metabolite plus adjuvants provided season-long improvements in growth and yield suggesting long-term alterations in plant physiology and/or the microbial communities in the rhizosphere (both internal and external). The plants derived from the biological or biorational seed treatments are referred to as enhanced holobionts and are likely to have significant effects on C sequestration and on soil organic material even though they do not differ genetically from the plants produced from seeds without the treatments.

The microbiome of most organisms is composed an assemblage of different species that form an ecological unit (https://en.wikipedia.org/wiki/Holobiont). These include plants and their associated microbial communities; the plant (or other organisms) plus its associated microflora is termed the holobiont (Gopal and Gupta 2016). The complex interactions of microbial communities with their plant host, or the phytobiome (www.phytobiomes.org/roadmap), affects the function and physiology of the host. Understanding the interactions and their effects are critical to developing predictive systems addressing challenges facing modern societies such as hunger and climate change (Blaser et al. 2016). Root and plant genetic make-up and physiology, the environmental milieu and their microbial and genetic communities affect nutrient uptake, water use efficiency, tolerance to a variety of stressors and are directly responsible for many yield-limiting traits (cf) (Adl 2016). The microbes that colonize internally can be pathogenic, symbiotic, or neutral their effects on plants. Further, these organisms may be part of natural microflora of plants, or they may be introduced with the intent of altering plant performance.

Numerous diverse organisms have adopted a symbiotic life style with plant roots, and can contribute markedly to plant growth and performance. Examples include nitrogen fixing Rhizobiaceae, plant growth promoting rhizobacteria (PGPR), Basidiomyeteous fungi in the sebiacales such as *Piriformaspora indica*, mycorrhizae, and specific strains of Ascomycetous *Trichoderma* spp (Harman et al. 2004b; Shoresh et al. 2010). Some of these are restricted to associations with specific plants, such as the Rhizobiaceae, while other such as *Trichoderma* and PGPR are more generalized. All of these diverse organisms appear to have abilities to enhance growth and performance of plants including qualitatively similar physiological and phenotypic responses; comparisons have been made of the of the qualitatively similar plant growth advantages provided by *Trichoderma* spp., *Piriformaspora indica* and PGPR include increased shoot and root growth, systemic resistance to disease, enhanced adventitious root growth, enhanced nutrient use efficiency and uptake, and enhanced resistance to oxidative stress (Shoresh et al. 2010) These phenotypic changes are associated with numerous changes in plant gene expression (Djonovic et al. 2006; Marra et al. 2006; Mastouri et al. 2012; Shoresh and Harman 2008b). Mycorrhizae also provide similar benefits and modes of action, cf (Mo et al. 2016). Both mycorrhizae and the *Trichoderma* strains described here colonize only root systems but induce systemic changes in plant gene and protein expression, thereby changing the physiology of the plant. Gene expression changes in plants by these diverse organisms result in up-regulation of entire pathways, such as those governing plant redox levels and photosynthetic activity (Han and Lee 2005; Kogel et al. 2003; Mastouri et al. 2012; Waller et al. 2005).

It is therefore an object of the present invention to provide a formulation and method for creating plant responses to these diverse organisms mediated by production of metabolites that interact with plants and give rise to beneficial systemic effects. The genetically diverse organisms induce similar kinds of changes that are mediated by metabolites, and the mechanisms of induction are different since the metabolomes of these diverse organisms are quite different in different groups of microbes. For example, with *Bacillus* species in the PGRP group, production of lipopeptides such as surfactin is critical for induction of induced systemic disease resistance (Cawoy et al. 2014), while active metabolites produced by *Trichoderma* spp. are chemically diverse from each other and to those from other microbes such as *Bacillus* spp. They include volatile apolar compounds, e.g., 6-pentyl-α-pyrone (6PP) and 1-octen-3-ol, non-volatile compounds such as heptelidic acid or koningic acid; peptaibiotics and peptaibols, and hydrophobins. These also induce systemic resistance to plant diseases (Lorito et al. 2010). Not only are the compounds quite different chemically, but they differ in their localization. For example, some are present in head spaces and presumably in the volatile form in soil, while other are water soluble, such as heptelidic acid or koninic acid, while the hydrophobins are partially embedded and part of the *Trichoderma* hyphae and cell walls and spores (Feofilova 2010). The differential localization and chemical structure therefore provides different routes of perceptions within plant-microbe interactions.

Improvements in plant performance, yield, and resistance to abiotic and biotic stresses are desired. Global climate changes are likely to increase disruptions of terrestrial weather patterns, which will limit crop production (Committee on Geoengineering Climate 2015). These changes, along with rising sea levels, desertification and increased urbanization will reduce land areas suitable for cultivation. Consequently, increasingly stressed and shrinking farm lands will need to feed an increasing human population, with an estimated 2 billion more people needing to be fed by 2050 (https://www.census.gov/population/international/data/idb/worldpopgraph.php). It is suggested that available food supplies need to double, either though enhanced plant productivity or a large reduction in food waste (Adl 2016).

Purposeful modification of the holobiont is potentially useful to enhance plant productivity and to overcome deleterious effects of biotic and abiotic stresses. For their advantages to be realized, these modifications must be applicable to agricultural systems. This means that they must be easily applied, reliable and relatively inexpensive compared to other agricultural inputs. Thus, studies need to be conducted in the field using standard agricultural practices.

The overall goal of this work was to evaluate purposeful modifications of the corn holobiont and their impact on crop performance. Specific objectives of the study reported here were to evaluate seed treatments with biological or biorational corn seed treatments applied over standard chemical pesticides to alter the corn holobiont, and evaluate: (1) the growth of the microbial agents onto radicles emerging from treated seeds, and subsequent localization of these agents on and in plants and their seeds; (2) evaluate these seed treatments with highly selected strains for their utility to increase yield, sequester C and improve nutrient uptake in the field; and (3) evaluate the abilities of the seed treatments to enhance root growth over an entire season.

Accordingly, there are numerous applications of the present technology as follows: (i) feeding a hungry world. The world population is expected to grow to about 9 billion persons by 2050, up from 7 billion now, and yields of major crop products will need to increase to meet this need (Taylor, 2015). The proposed research describes the potential of a significant alteration in the phytobiome of corn that has potential to improve the fundamental photosynthetic capability of this crop that will result in significant yield improvements. Moreover, while this project is primarily directed to large agbio in the developed world, the basic technology is appropriate also for small growers in the emerging nations; and (ii) addressing levels of greenhouse gases in the atmosphere. In 2010, there was a net increase of about 33 billion tons of CO2 in the atmosphere, which is contributing to global warming. Recently, a group of business leaders has called for net-zero increases in this gas in the atmosphere.

The present invention further provides for farmer-applied products and/or treatment of seeds by seed treatment or seed companies so that farmers get an in-the-bag solution, where the direct application by farmers and attendant variable application, can be modified and/or avoided.

To meet this goal, not only do emissions need to decrease, but methods for removal of CO2 need to be implemented. The proposed research envisions a system which can remove up to 91 t/ha of CO2 via photosynthesis. Annual crops have not been considered as candidates for sequestration and removal of this gas from the atmosphere because the crop is utilized and CO2 re-released into the atmosphere. However, only about 50% of crops are typically ever harvested, while the roots and other subterranean tissues are located in the soil, where they gradually decompose and are converted into organic matter in the soil. The proposed technology has been demonstrated to increase root biomass (up to doubling) with plants grown from treated seeds. This results in the soil becoming a reservoir of sequestered carbon and also results in an increase in organic matter in the soil, which results in more productive soils with higher tilth. Beyond this, the proposed technology increases the abilities of corn plants to take up nitrogen, and this can result in decreases of leaching of nitrates and nitrites into the ground water, and to decreases in nitrous oxide release into the atmosphere. Nitrates and nitrites are potent polluters of waterways and nitrous oxide contributes to global warming. Thus, the changes induced in corn can make them part of the solutions to global warming and water pollution rather than being part of the problems.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure:

FIGS. 21A-21D depicts laboratory data demonstrating enhanced capabilities of tomatoes grown in the presence of strains of the present invention in the absence of stress or under water deficit (soil moisture maintained at 60-70% of saturation) conditions Shown are Chlorophyll SPAD readings and Photosynthetic efficiency.

DESCRIPTION OF THE PREFERRED EMBODIMENTS

Figure 1:
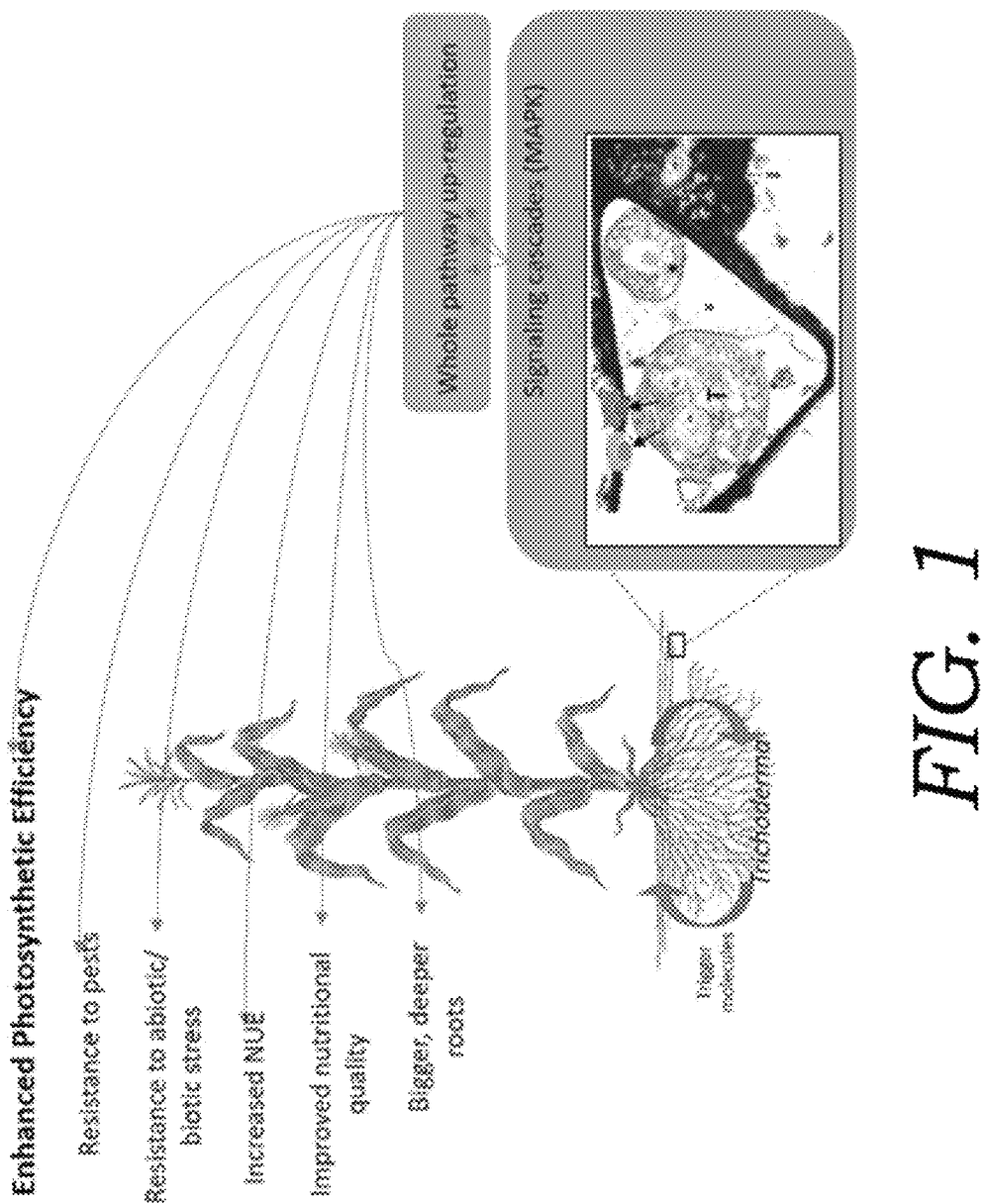
FIG. 1 depicts a diagrammatic representation of the interactions between endophytic *Trichoderma* strains and plants.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

In practicing the present invention, many conventional techniques in molecular biology, protein biochemistry, cell biology, immunology, microbiology and recombinant DNA are used. These techniques are well-known and are explained in, e.g., Current Protocols in Molecular Biology, Vols. I-III, Ausubel, Ed. (1997); Sambrook et al., Molecular Cloning: A Laboratory Manual, Second Ed. (Cold Spring Harbor Laboratory Press, Cold Spring Harbor, N.Y. (1989)); DNA Cloning: A Practical Approach, Vols. I and II, Glover, Ed. (1985); Oligonucleotide Synthesis, Gait, Ed. (1984); Nucleic Acid Hybridization, Hames & Higgins, Eds. (1985); Transcription and Translation, Hames & Higgins, Eds. (1984); Animal Cell Culture, Freshney, Ed. (1986); Immobilized Cells and Enzymes (IRL Press, 1986); Perbal, A Practical Guide to Molecular Cloning; the series, Meth. Enzymol., (Academic Press, Inc., 1984); Gene Transfer Vectors for Mammalian Cells, Miller & Calos, Eds. (Cold Spring Harbor Laboratory, New York (1987)); and Meth. Enzymol., Vols. 154 and 155, Wu & Grossman, and Wu, Eds., respectively. Methods to detect and measure levels of polypeptide gene expression products (i.e., gene translation level) are well-known in the art and include the use polypeptide detection methods such as antibody detection and quantification techniques. (See also, Strachan & Read, Human Molecular Genetics, Second Edition. (John Wiley and Sons, Inc., New York (1999).)

Unless defined otherwise, all technical and scientific terms used herein generally have the same meaning as commonly understood by one of ordinary skill in the art to which this invention belongs. As used in this specification and the appended claims, the singular forms "a," "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art. All references cited herein are incorporated herein by reference in their entireties and for all purposes to the same extent as if each individual publication, patent, or patent application was specifically and individually incorporated by reference in its entirety for all purposes.

Definitions

The definitions of certain terms as used in this specification are provided below. Definitions of other terms may be found in the Illustrated Dictionary of Immunology, 2nd Edition (Cruse, J. M. and Lewis, R. E., Eds., Boca Raton, Fla.: CRC Press, 1995). Unless indicated otherwise, the term "biomarker" when used herein refers to the human biomarker, e.g., a human protein and gene.

As used herein, unless otherwise stated, the singular forms "a," "an," and "the" include plural reference. Thus, for example, a reference to "an organism" or "the organism" includes a plurality thereof.

As used herein, the term "about" will be understood by persons of ordinary skill in the art and will vary to some extent depending upon the context in which it is used. If there are uses of the term which are not clear to persons of ordinary skill in the art, given the context in which it is used, the term "about" in reference to quantitative values will mean up to plus or minus 10% of the enumerated value.

As used herein, the term "composition" refers to a product with specified ingredients in the specified amounts, as well as any product which results, directly or indirectly, from combination of the specified ingredients in the specified amounts.

As used herein, the term "reference level" refers to a level or measurement of a substance or variable which may be of interest for comparative purposes. In some embodiments, a reference level may be a specified moisture content as an average of the moisture content taken from a control subject/plant. In other embodiments, the reference level may be the level in the same subject/plant at a different time, e.g., a time course of administering or applying a particular composition or formulation.

As used herein, the terms "produce", "crops", "food component", "system component", "augmentation variable" or "subject" refer to a plant, fungus, microbial colony, mammal, such as a human, but can also be another animal such as a domestic animal, e.g., a dog, cat, or the like, a farm animal, e.g., a cow, a sheep, a pig, a horse, or the like, or a laboratory animal, e.g., a monkey, a rat, a mouse, a rabbit, a guinea pig, or the like.

As used herein, the terms "treating" or "treatment" or "alleviation" refer to both therapeutic treatment and prophylactic or preventative measures, where the objective is to prevent or slow down (lessen) the targeted disease, condition or disorder. A subject/plant is successfully "treated" for a disorder if, after receiving therapeutic intervention/application according to the methods of the present invention, the subject/plant shows observable and/or measurable reduction in or absence of one or more targeted disease, condition or disorder.

As used herein, the terms "amphipathic" or "amphiphilic" are meant to refer to any material that is capable of polar and non-polar, or hydrophobic and hydrophilic, interactions. These amphipathic interactions can occur at the same time or in response to an external stimuli at different times. For example, when a specific material, coating, a linker, matrix or support, is said to be "amphipathic," it is meant that the coating can be hydrophobic or hydrophilic depending upon external variables, such as, e.g., temperature.

As used herein, the terms "matrix" or "support" or "hydrogel matrix" are used interchangeably, and encompass polymer and non-polymer based hydrogels, including, e.g., poly(hyaluronic acid), poly(sodium alginate), poly(ethylene glycol), diacrylate, chitosan, and poly(vinyl alcohol)-based hydrogels. "Hydrogel" or "gel" is also meant to refer to all other hydrogel compositions disclosed herein, including hydrogels that contain polymers, copolymers, terpolymer, and complexed polymer hydrogels, i.e., hydrogels that contain one, two, three, four or more monomeric or multimeric constituent units. Hydrogels are typically continuous networks of hydrophilic polymers that absorb water.

As used herein, the term "polymer" refers to a macromolecule made of repeating monomer or multimer units. Polymers of the present disclosure, include, but are not limited to, poly(hyaluronic acid), poly(sodium alginate), poly(ethylene glycol) (PEG), poly(lactic acid) polymers, poly(glycolic acid) polymers, poly(lactide-co-glycolides) (PLGA), poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(methacrylic acid), polylactic acid (PLA), polyglycolic acids (PGA), nylons, polyamides, polyanhydrides, poly(ethylene-co-vinyl alcohol) (EVOH), polycaprolactone, polyvinylhydroxide, poly(ethylene oxide) (PEO), and polyorthoesters or a co-polymer or terpolymer formed from at least two or three members of the groups, respectively.

As used herein, the term "introduce" refers to the incorporation of an eukaryotic or prokaryotic cell or component thereof into or on a plant or crop, where the cell or component may be incorporated into the formulation of interest. The term includes such nucleic acid introduction means as transfection, transformation, and transduction.

Microbes of the present invention belong to the fungal genus *Trichoderma* in some embodiments, although additional organisms are used within the concept of Focused Microbial Diversity, as further discussed herein. Such agents are applied as seeds treated with the living spores in various aspects of the present invention. And, while these fungi have been identified for about 90 years as having potential in agriculture (Weindling, 1932, Weindling, 1934), only through the present innovation has strain selecting and technology development permitted successful application and unexpected efficacy. More than 10,000 strains were screened, e.g., *T. virens* strain 41, *T. harzianum* strains T22, strain ATCC accession number PTA 9707 and 9708, *T. atroviride* strain accession number PTA 9709, some of which are employed as active ingredients of various aspects of the technology in various modalities as well, e.g., as farmer applied planter box (PB), and for commercial seed treaters as a dry high concentrate (HC) and as a liquid (LQ) product. Strain specificity is an integral component of the present technology at least insofar as it cannot be assumed that because one strain of, for example, *T. harzianum* is effective another strain will be. Indeed, these fungi are very common in soil, and the total amount of wild strains in soil probably will outnumber the numbers of the strains applied as seed treatments by 10,000× or more.

The strains of the present invention are unique and effective. In certain embodiments, a primary screen is performed to ascertain the ability of the strains to colonize roots and establish endophytically within the root cortex. When applied to seeds and the seeds planted, the strains grow very rapidly onto the emerging radicle of most seeds—within the first 48-72 hr, their populations may increase by as much as 10,000 fold. Further, shortly thereafter, the root hairs become colonized (see FIG. 13A-B). The hyphae are restricted to the cortex, but are able then to grow with and colonize the entire root, giving season-long benefits. This ability of very highly selected strains to be endophytically and rhizosphically competent is of fundamental importance not shared by most strains. This allows them to become fully integrated into the plant and function as true plant symbionts (Harman, 2000, Harman, 2011, Harman, Howell, et al., 2004, Shoresh, Mastouri, et al., 2010).

FIG. 1 shows a diagrammatic representation of the interactions between endophytic *Trichoderma* strains and plants. The fungi (represented by the box and the term beneficial microbes) colonize the roots, and are restricted to the cortical cells. The strains used in this study continue to proliferate in the plant and, as shown, induce season-long effects (Harman et al. 2004; Shoresh et al. 2010). These fungi produce a variety of metabolites that can mimic the effect of the organisms and these are hypothesized to bind to receptors in the plant cells. One such metabolite is 1-octen-3-ol used in the present invention. As a consequence, plants respond with numerous changes in plant gene expression (Djonovic et al. 2006; Marra et al. 2006; Mastouri et al. 2012; Shoresh and Harman 2008). This results in substantial changes in plant physiology and performance, including increased biomass of both shoots and roots, enhanced photosynthetic efficiency (see also (Doni et al. 2017; Vargas et al. 2009)), resistance to diseases (Djonovic et al. 2006; Shoresh et al. 2010), resistance to abiotic stresses such as drought, salt (Guler et al. 2016; Mastouri et al. 2012), and flooding (this disclosure), increased nitrogen use efficiency (Guler et al. 2016; Harman and Mastouri 2010) and this disclosure, and enhanced antioxidant levels in produce.

The symbiotic capabilities are realized by the ability of the root-contained fungi to establish chemical communication with the plant, and to transmit that signal systemically, giving plant-wide changes in the plant (Shoresh, Gal-on, et al., 2006, Shoresh, Mastouri, et al., 2010). These systemic changes result in changes in plant gene expression; hundreds of genes are up-regulated (Shoresh and Harman, 2008). These include coordinated up-regulation of entire pathways, and not just random gene or protein expression enhancement. This results in plants that (a) have enhanced resistance to disease, (b) markedly enhanced resistance to abiotic stresses such as drought, salt, flooding and others, (c) bigger and deeper roots, (d) increased abilities to utilize nitrogen and other fertilizers, and enhancement of seed germination (Harman, Cadle-Davidson, et al., 2015, Mastouri, Bjorkman, et al., 2010, Shoresh, Mastouri, et al., 2010). This is shown diagrammatically in the electron micrograph above from (Yedidia, Benhamou, et al., 1999). All of these benefits are energy-intensive, and cannot without improved photosynthetic capability of the plant (Shoresh and Harman, 2008).

The concepts underlying the induction of stress resistance in plants are unique. Plants suffer from accumulation of reactive oxygen species (ROS) as a consequence of stress, such as drought, salt, temperature or flooding, and as a by-product of over-excitation of photosynthetic systems. Thus, the internal environment of plants frequently contain an unfavorable redox balance. Our beneficial organisms induce changes in plant gene expression including upregulation of entire pathways. Among those pathways that are enhanced are those that minimize accumulation of harmful ROS. In the presence of our organisms, plants have an optimized internal redox environment (OIRE) that provides many benefits. Induction of the plant pathways leading to OIRE in the presence of stress appear to be an inducible primed system, just as resistance to diseases is (Harman, Cadle-Davidson, et al., 2015). In addition, several lines of evidence indicate that the total photosynthetic machinery in plants is enhanced (Shoresh and Harman, 2008, Vargas, Mandawe, et al., 2009). Photosynthesis itself gives rise to ROS as a by-product of over-excitation of photosynthetic pigments, and so also results in ROS. This complex interaction is facilitated by the combinations of strains in the present disclosure to upregulate the entire redox control pathway leading to OIRE, which is important for control of abiotic stresses and to provide additional photosynthate for plant growth.

With corn, in hundreds of trials plant growth promotion and enhancement, improvement of root size and there is almost always an amelioration of abiotic stresses such as drought. In some cases, but not always, this increased plant growth in translated into increased plant yields, either of biomass (silage) and/or grain yield, although there appears to be less or more efficient translation depending on the variety. Previously developed strains of *T. harzianum* (T22) by the present inventors were analyzed using extensive field trials with T22 on corn, and found that T22 increased yields and growth on most corn genotypes, where about 20% of the genotypes saw no increase in yield. Additional field trials on these strains, and different strain combinations were used for different crops, with *T. harzianum* strain K2 (PTA ATCC 9708) and *T. atroviride* strain K4 (PTA ATCC 9707). See, e.g., U.S. Pat. Nos. 8,716,001 and 8,887,480. Land and facilities for envisaged, additional, large trials that are envisioned. They also have access to the remote sensing capabilities that are required. These providers will permit the cross-regional data necessary for the success of the present invention, and will permit immediate access to their precision agriculture systems that will allow for rapid implementation of the such compositions and methods.

In some aspects of the present invention, biological products and strains colonize roots through their endophytic associations and the changes in gene expression. The result is a plant that may upregulate more than 100 specific genes. These upregulated genes are not random, but are coordinately organized into specific plant pathways. The result is a non-engineered plant that nonetheless functions very differently than plants without the microbial agents. The plants thus produced are basically new plants that differs considerably from the same variety without the organism. Likewise, corn and many other crops respond reliably to root colonization by known *Trichoderma* strains to give the following reliable and reproducible results.

Enhanced growth and leaf greenness in young plants (for corn, this is typically growth stages (V4-V6), with associated increases in root growth. For example, in GH15 and GH 15 field trials, five different varieties were evaluated and the average increase in early growth was about 12%, which, with one exception, were statistically significant at P=0.01 with the commercial seed treatment SabrEx LQ™ (SABREX. LQ) sold by Advanced Biological Marketing. These plant height differences are visible in the field and frequently associated with increased leaf greenness (Harman, 2000). This occurs even though the biological treatment is applied over standard fungicide-insecticide combinations.

Consistent and reliable resistance to abiotic stresses such as drought, flooding, and salt. Recovery from flooding was demonstrated in the GH15 field trials, where one variety was located in a low part of the field and, in a very wet spring, seedlings emerged and then were submerged for about three weeks, after which they had good growing conditions. The initial growth during the submerged stage was very poor, but after conditions improved, the plants grown from SabrEx™ (SABREX)-treated seeds recovered and grew with greater vigor. The grain yield of the plants not treated with such products was about 9.5 t/ha but in the presence of SABREX the yield was 13 t/ha, which was 36% better, while plant growth was enhanced even more, and plants were 85% larger. These improvements were attributable to recovery from flooding and also because of the intrinsic ability of the strains to enhance plant growth and performance.

Figure 2A:
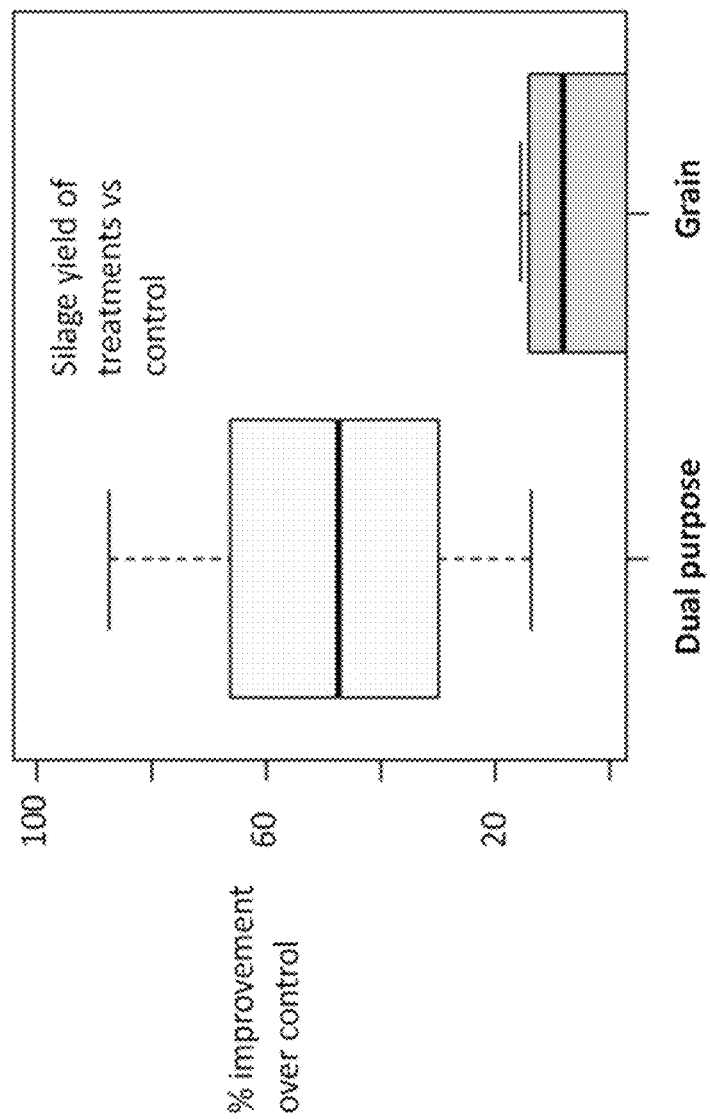
FIGS. 2A-2B depicts charts showing increase in silage (FIG. 2A) or grain yield (FIG. 2B) in two types of hybrids. The data shown is from two hybrids of each type two hybrids of each type and four separate biological treatments. Data from each variety×treatment was the mean across four replicates.
Figure 2B:
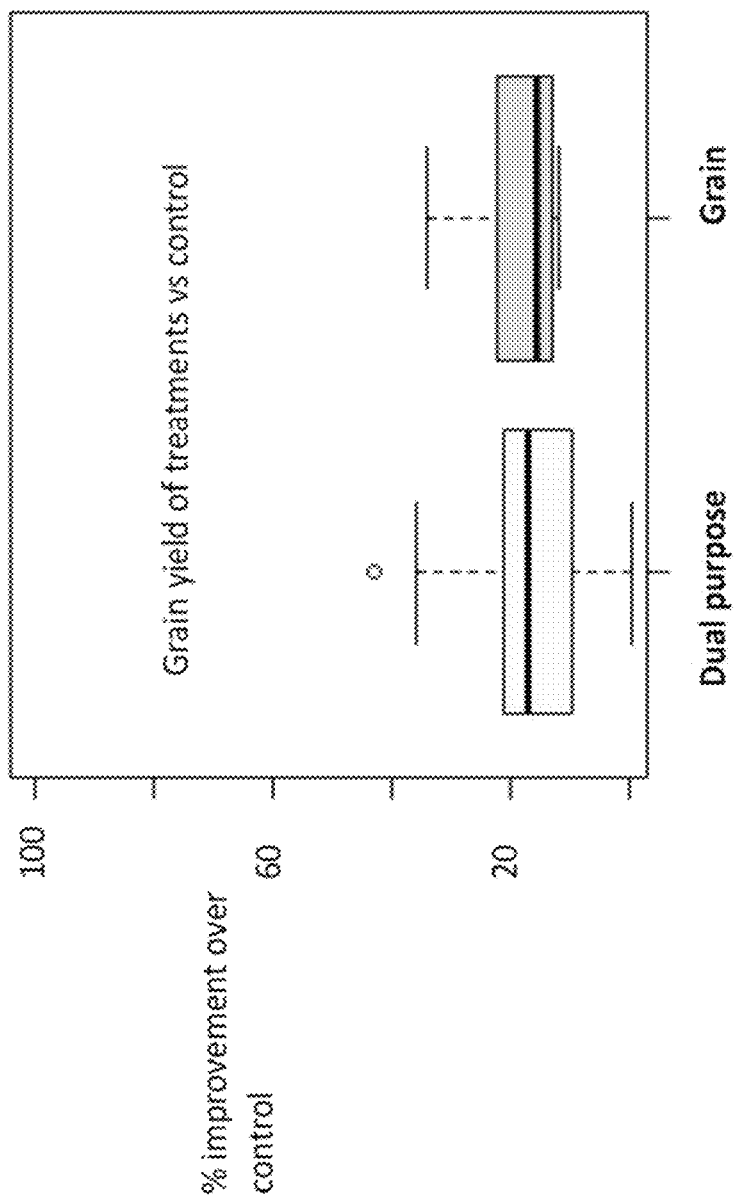

Effects of corn variety respond with improved growth, better resistance to stress and enhanced photosynthetic capability, but that the translation of the benefits is dependent upon corn genotype. Our results in the GH15 field trial indicate that the type of corn, whether it is intended as a dual purpose silage (total biomass) or strictly for grain, strongly affected results. This is shown in FIGS. 2A-2B. The data, which is from replicated field trials across two hybrids of each type and four separate biological treatments, demonstrates that the silage yield response to our biological treatments is small to nonexistent in the grain hybrids but quite large in dual purpose hybrids.

However, improvements in grain yields were similar with both hybrid types. Further, in both cases, as noted in the general information above, there were substantial and significant differences in vegetative growth of all varieties about 2 months after planting, so all of the lines responded to the biological treatments. Finally, it should be emphasized that yields with all lines were quite good with silage yields of 50-<70 t/ha and grain yields of 12-<15 t/ha. In every case, the biological treatments resulted in statistically significant yield increases in silage and/or grain. Clearly, the hybrids intended for grain and as dual purpose use differ in response to the microbial agents (FIGS. 2A-2B). One important component of these appears to be in starch type-grain varieties may have a higher bulk density because they contain more vitreous starch, while silage varieties have a lower bulk density, which is reflective of a more floury endosperm where the starches are bound more loosely in a strain:protein matrix (Mahanna and Thomas, 2015).

Regardless of the mechanisms, differences in response demonstrate that different corn genetotyes provide differences in genetic×microbial agent response, and these may be unpredictable in the absence of empirical data. In the case noted above, it is hypothesized that the photosynthate to starch loading into grain differs. All of the varieties tested responded positively to the biological treatment but the end result differed. Data like these are indeed very important to farmers and users of corn. However, when we consider the potential for carbon sequestration in greenhouse gas amelioration, then total biomass becomes very important. Obviously, dual purpose type hybrids will be more efficient in assimilation of carbon than will grain varieties.

Effects of nitrogen fertilization are also relevant to the present invention. Corn growing requires high nitrogen levels for best yields, either of biomass (silage) or of grain. The yield response to N fertilization has been modeled, and while specific models differ, it is apparent that there is an initial increase of yield as N rates increase, but that there then follows a leveling of the response, which is designated the yield plateau and, above which, little additional yield response occurs (Cerrato and Blackmer, 1990). The level of the plateau occurs at around 150-200 kg of N/ha. However, several lines of evidence suggest that the model is not adequate to describe the N/yield relationship in the presence of the altered plant that occurs as a consequence of endophytic colonization with our organisms. Some of these lines of evidence are as follows. The yield plateau begins at a lower level (i.e., less N is required to obtain similar yield levels) (Harman, 2000).

In one embodiment of the present invention, nitrogen uptake facilitated by OIRE continues to increase as yields increase. There is no evidence that corn in the presence of N requires any less N for a specific yield response in the presence of our endophytes, and the increase in yields that are frequently observed is accompanied by higher total N uptake. In GH14 field trials in, biomass was increased by 31% and total N, as measured by analyses of the biomass, increased to about 760 vs 560 kg/ha, while in the GH15 trial the greatest biomass yield increase was almost doubled, and the total N was about 1000 kg vs again, 560 kg. The high values are in considerable excess of the applied N fertilizer, which suggests that endophyte-colonized corn roots are more effective in acquiring N than non-treated ones. The reason that N continues to accumulate and to drive yields even more is a function of the presence of greater photosynthate levels and higher overall energy for the plant. Greater photosynthate levels provides the carbon scaffolding onto which amino acids can be located. Of course, the greater root volume and depth of penetration assists in this result. Regardless, these data suggest that the corn in the presence of the compositions of the present invention can effectively use more N, and convert this into biomass, than nontreated corn. These data, regarding both corn hybrid type and N utilization demonstrate that corn (and by extension other plants) are dissimilar in responses to noncolonized corn. This is further evidence that the treated plants are new plants and new models for corn and its use need to be developed.

Such evidence is further supported by real-time data on the performance of the crop as it develops. In the large trials that are envisioned, direct measurements on the ground are impractical. The use of known observation means, such as unmanned aerial vehicles (UAVs), may be used to capture visible light images and Normalized Difference Vegetation Index (NDVI) data. These strategies are rapidly becoming a functional part of agriculture with satellite and/or UAV-based yield predictions being provided by several companies around the U.S. (e.g., http://www.agrinetix.com/, http://www.precisiondrone.com/, http://www.ursula-agriculture-.com/). Based on reflectance over multiple infrared wavelengths, these data measures changes in photosynthesis that have been correlated to drought, nitrogen stress, or other conditions (Clay, Kim, et al., 2006, Osborne, Schepers, et al., 2002, Zaman-Allah, Vergara, et al., 2015). Also of potential use here is reflectance measurement in the visible green band, which has been shown to correlate more specifically with nitrogen stress (Clay, Kim, et al., 2006, Osborne, Schepers, et al., 2002). The Nitrogen Reflectance Index (NRI) is a comparison of near-infrared (NIR) and green band reflectance (Bausch and Duke, 1996); however, acquiring the appropriate wavelengths requires multi- or hyperspectral cameras which are not commonly available with agricultural UAV services due to their costs. Another alternative is LiDAR, which uses reflected laser beams to measure topography and, after a crop has grown, to measure plant height. Using such techniques, sample NRI data is obtained to determine plant nitrogen stress/content. Using these methods, plant growth characters and stress conditions can be monitored in a few minutes rather than the several hours—or even days—it would take field technicians on the ground. This rapid data capture also reduces the variability caused by time of day, changeable weather conditions, and other confounding factors, and thus increases the quality of data for the later association analyses To conduct comprehensive field trials to determine the complex interactions of the microbial products of the present invention for ×corn hybrid types×nitrogen fertility levels are considerations tied to the present technology. Likewise, improving remote sensing capabilities for prediction and validation of corn performance criteria is envisaged. Such trials will be conducted on grower fields in various locations around the country and consist of at least five different commercial corn hybrids adapted to the climate and area where the trials occur. Each of these will receive five separate levels of nitrogen fertilizer, ranging from about 100 to 400 kg N/ha. Various treatments and controls are performed (the untreated control and all biological products will already be treated with standard fungicides and insecticides appropriate to the crop and area).

Figure 3:
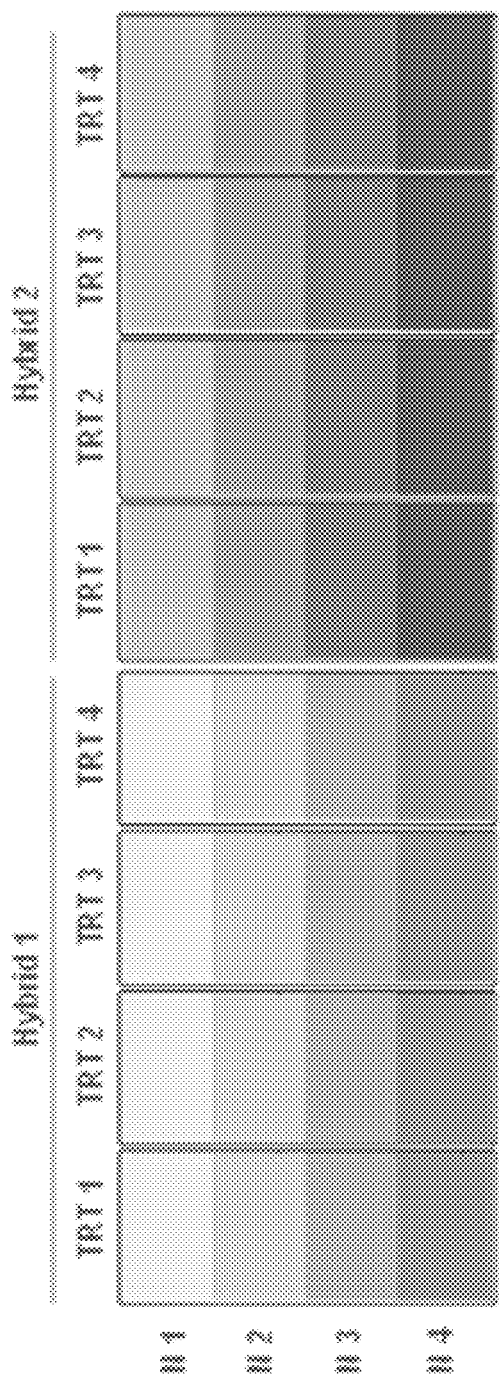
FIG. 3 depicts the field configuration for trials, where two hybrids of five that are expected in each trial are shown, with representatives of each important class (grain vs dual use; determinate and indeterminate ear type) are included. N1-N4 represent different levels of N that will be applied primarily at V4-V6 to give a range between 100 and 400 kg/ha, including whatever starter fertilizer will be used.

Examples of known treatments include SABREX LQ seed treatment, which a product currently sold, and which contains *T. afroharzianum* strain K2 and *T. atroviride* strain K4 in a liquid formulation at $1\times10^9$ colony forming units per ml. This product will be used at a rate of 0.7 ml/kg seeds, which is the commercially recommended rate. K5As2. Seeds will be treated with this mixture at the rates as indicated above except that *B. amyloiquifaciens* can be used at the rate of $1\times1010$ colony forming units per ml. OMEGA™, sold by Advanced Biological Marketing (OMEGA) seed treatment will also be used. This material contains as the active ingredient a *Trichoderma* metabolite that is strongly active in plant growth promotion and induction of plant disease resistance. This material in previous experiments is active at very low concentrations (less than 1 µl/seed) and to have activity that persists on seedlings for at least two months after planting. The non-microbial agent will also contain a humate compound and a plant nutritive substance. This material confers many of the advantages of our living organisms and was discovered as part of our in depth studies on mechanisms. This product appears to be advantageous where customers wish to use a biologically-incompatible formulation but still obtain the advantages of the microbial agents. Untreated control, but that will include standard fungicide/insecticide mixtures, as will be case for all treatments. Trials are conducted in the field with each treatment×rep consisting of at least 12 rows of treated seeds. An example of the field configuration is provided in FIG. 3, where two hybrids of five that are expected in each trial are shown, with representatives of each important class (grain vs dual use; determinate and indeterminate ear type) are included. N1-N4 represent different levels of N that will be applied primarily at V4-V6 to give a range between 100 and 400 kg/ha, including whatever starter fertilizer will be used.

These trials were established, at 2 geographic locations and the following data were collected at one location: soil analysis, plant height, stand density, stalk diameter, stalk nitrogen content, and plant gene expression profile.

For this data collection, as much as possible is acquired through remote acquisition using NVDI or, preferably, multispectral or LIDAR imaging. These remote systems remove much of the requirement for actual ground sampling. However, leaf sampling as indicated is conducted as well, and the stalk diameter measures are also conducted via ground sampling. Further, we anticipate that there may be environmental issues that arise, such as outbreaks of disease, drought, or other factors. These can be detected initially via remote sensing, but then ground truth will have to be determined by actual observations by trained staff.

In addition to these analyses, we also measure final yields of both biomass (silage) and grain yield. For the latter two data types, plots will be harvested by machine that include yield monitors and telemetry. These are anticipated to give pseudo-replications across different specific locations in the field and will obviate the requirements for hand harvesting. Once samples of silage and grain are obtained, their quality is evaluated. This includes analyses of content of C, N, protein quantity, protein levels, starch and digestible and nonstructural carbohydrates, lignin and elemental analyses of both grain and silage. Data and predictive analyses are performed on four separate replicates for each parameter measured. Data was analyzed to determine differences using the R statistical package (The R Foundation for Statistical Computing Platform). A great deal of information on crop performance that will define the performance of the corn plants that will differ typically expected existing systems. These are as shown below.

Figure 4:
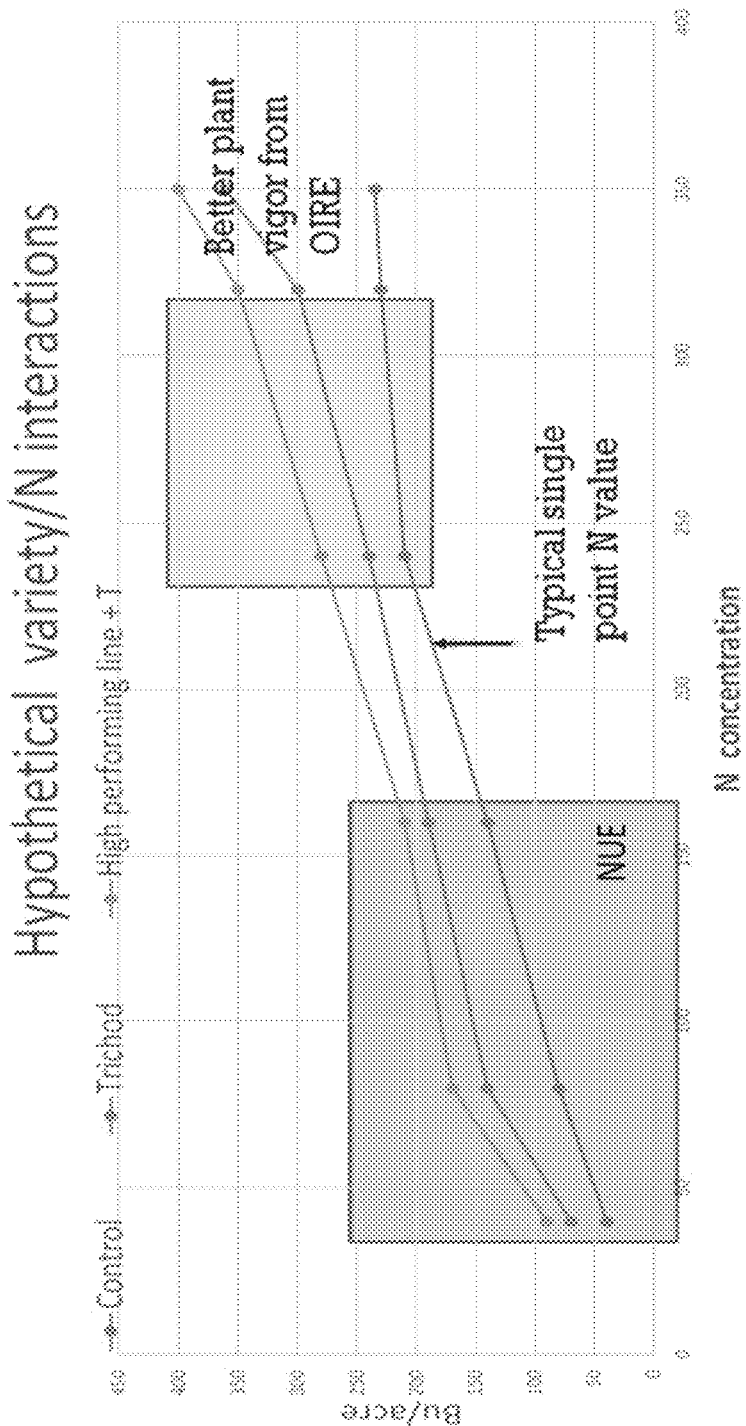
FIG. 4 depicts a graph showing relationships between varieties, N level and yield, suggesting that, at low levels of N, the presence of *Trichoderma* will increase yields. Data from standard N levels are shown, as is the consequence of improved vigor at high N levels.

The relationship of yield of both silage and grain yields across varieties and differing N levels is shown in FIG. 4. The expectations are that these will differ from nontreated lines and is exhibited. Data indicating that different hybrids will perform differently have been obtained and higher levels of photosynthate is envisaged, which translates into increased yields if N is not limiting. However, it is only through N dosage response curves in the presence or absence of Trichoderma and across different types of corn that the actual relationships can be ascertained. Regression analyses based on data across N levels are standard analyses and these are performed (Cerrato and Blackmer, 1990).

These analyses provide for information on the relationships and are confirmed across multiple years and geographic and climatic regions. Gaining abilities to predict plant performance primarily based on remote sensing data is also an aspect of the present invention. For example, validation of our models for C sequestration are proportional to biomass yields. This is validated using NVDI measurements in addition to, if necessary, LIDAR which measures plant heights. The values we obtain from the remote sensing measures can be correlated with plant yields as measured from silage (total above-ground biomass) measurements. Moreover, being able to predict, for corn type across N applications, what final yield is likely to be from measurement at V4-V6 is possible, which is then employed as a prescriptive recommendation for yields at specific levels.

The data discussed above and obtain as detailed further herein provide for refinement of both the types of remote sensing and yield predictable models, if necessary. Such systems are used as prediction of yields according to inputs and for validation of C sequestration for use in any system that is developed for removal of greenhouse gases, a preferred embodiment of the present invention.

In the systems described herein, crop yields are increased, and thereby meet challenges of a growing world population, and to mitigate global climate change. Adopting methods, systems and programs for the immediate worldwide implementation by the agricultural community are also envisaged. To accomplish this, the field trials are conducted in various geographic locations for validation.

Aspects of the present invention provide advantages based on methods and products that exploit advantageous microbial mechanisms. While other technologies have course approaches involving evaluating scores of microbes over hundreds of trials and then using statistical approaches to discovery and then develop products based on efficacious microbes, the present invention includes the development of combinations of strains by understanding their mechanisms of action, developing enabling technologies (e.g., efficacious formulations), and have field-predictive screening in extensive laboratory trials. Field trials are used to confirm results, and, if necessary, return to developmental work in the lab and the field to cure negative effects. This is accompanied by complete sequencing of strains and identification of active metabolites and we are seeking to link specific microbial genes and metabolites to specific functions and changes in gene expression in plants. As such, the present methods are efficient and effective, and is the only possible system providing for increased plant growth and stability while improving the environment. The evolutionary development of the present technologies also provide for predictive modeling based on remote sensing.

Carbon Offsetting—Current forecasts for carbon offsets per ton of CO2 sequestered range from $7 to $170 between now and 2050. These estimates are based on extrapolation of the experience the European Union Emission Trading Scheme (EU ETS) that established a functioning carbon market with a large-scale emissions cap and trade system. Between April 2005 and April 2006, the spot price averaged at approximately £22 per ton carbon offset. These prices are premised on the assumption that CO2 emitting industries and sources can trade their emissions for carbon offsets that reduce equivalent emissions elsewhere. Challenges to the system have included the fact that the reduction in emissions are difficult to verify and that offsetting reductions in emission would have happened anyway (thereby reducing the value of the offsets). New proposals for Cap and Trade systems are under discussion before the Copenhagen meeting in Copenhagen 2009.

The methods of carbon sequestration of the present invention are immune to both these challenges. Firstly, the sequestered carbon is physically available for analysis and can be documented without any ambiguity. Secondly, none of the biomass would have been created otherwise. The purpose of the scheme is entirely to create additional biomass from abundant resources without offsetting other food, biomass-generating or carbon 60 fixing activities (and without creating new sources of CO2 emission, for example, through the burning of fossil fuel to generate the power needed to operate the system). The carbon intensity of traditional OTEC is already lower than that of hydroelectric power.

Based on these advantages, the methods hereof qualify for the highest quality carbon offset ratings and can secure the maximum rewards available through direct payments. Alternatively, revenue can be generated from the biomass generated alongside the CaCO3, making the system independent of the carbon offset market.

The present invention relates to, inter alia, the discovery and development of a biological system of plant growth promotion by application of a highly effective strain of *T. viride*. This strain outperforms the best current strains of *Trichoderma* used for this purpose available commercially. It can be used in conventional or organic agriculture for the promotion of plant growth and increase in crop yields when applied topically as a foliar spray or as a seed coating. It consists of a biologically active strain of *Trichoderma viride*.

The plant root biome is a complex interactive system that includes root associated microbes, soil associated microbes, the plant root and other organisms. Some microbes, such as *Trichoderma* spp., have been known and suggested for decades as agents for control of plant pathogenic microbes (Weindling, 1932, Weindling and Fawcett, 1936). Since that time, understanding and use of these fungi and others has been the subject large and evolving body of knowledge (Harman, 2000, Harman, 2011, Harman, Howell, et al., 2004). Originally, as suggested by authors such as Weindling, the biocontrol abilities of these organisms was expected to occur as a consequence of mycoparasitism, antibiosis (Weindling, 1932, Weindling and Emerson, 1936, Weindling and Fawcett, 1936), and simply competition. Significant advances included the discovery of the abilities of very specific strains to be rhizosphere competent, i.e., to be able to colonize, persist and grow with roots to provide long-term benefits (Ahmad, 1987, Sivan and Harman, 1991). Beyond this, some strains were shown to penetrate and become established asymptomatically in root cortical cells. These strains induced the plant to wall off and limit the organism to the first few layers of root cells (Yedidia, Benhamou, et al., 1999). This was accompanied by signaling to the plant to provide induced systemic resistance via a priming type mechanism (Yedidia, Benhamou, et al., 2000, Yedidia, Shoresh, et al., 2003). MAPK signaling was required for the systemic effect (Shoresh, Gal-on, et al., 2006). The ability of certain selected strains to become established internally in roots, grow with roots and induce systemic changes in the plant we define as endophytic and rhizospheric competence. This capability is associated with induction of large changes in plant gene and protein expression, with the greatest changes occurring in the above ground parts of the plants even though the competent strains are located only on roots (Shoresh and Harman, 2008).

These endophytic microorganisms frequently are fully symbiotic with plants (Harman, Howell, et al., 2004). These endophytic symbionts have abilities to induce multiple beneficial effects in plants, including induced resistance to diseases and potentially other pests; resistance to abiotic stresses such as drought, salt and flooding; improved efficiency of uses of nitrogen and other plant nutrients; enhancement of seed germination and seedling vigor; and enhanced plant growth and development. There are numerous diverse genera of microbes that induce at least most of these changes in plant performance, including mycorrhizae, plant growth promoting rhizobacteria, and Basidomycetous fungi in the Sebaciles such as *Piriformaspora indica*. These organisms have an endophytic versus a plant pathogenic life style (Shoresh, Mastouri, et al., 2010) typical of numerous other plant-associated microorganisms. The systemic changes in plant gene expression are presumed to be induced by the production of specific triggering metabolites from these different organisms. These metabolites must be different from these diverse organisms, since they effective organism are very distantly related, and some are even in different kingdoms, so it is unlikely that the same specific pathways of gene expression upregulation and even the specific plant genes upregulated are the same. A number of microbial metabolites with that are strongly active in altering plant phenotypes at low concentrations (<1 μmolar) have been identified; e.g., lipopeptides from *Bacillus* spp. (Cawoy, Mariutto, et al., 2014, Debois, Fernandez, et al., 2015), and hydrophobic proteins (Djonovic, Vargas, et al., 2007, Ruoccco, Lanzuise, et al., 2015) and volatile and nonvolatile metabolites from *Trichoderma* spp. (Vinale, Sivasithamparam, et al., 2008). In our preliminary work we have discovered that, at very low concentrations, 1-octene-3-ol (mushroom alcohol), a metabolite of *T. harzianum* and other species (Hung, 2014), strongly enhances plant growth and is highly effective in induction of plant disease resistance.

In an additional embodiment, a collection of sixty eight *Bacillus* spp. isolated from plant parts or roots were examined for their abilities to qualitatively induce the same positive responses in plants that our selected strains of *Trichoderma* do. Assessed was their ability to induce increases in plant growth and to confer disease and stress resistance. Strain As2 from alfalfa stems was a strongly performing strain. However, as noted above, *Bacillus* spp. cannot produce the same metabolites or affect plants via the same mechanisms. For this reason, one embodiment of the present invention utilizes combined strains of *Trichoderma* with As2. In addition, humate-based formulations are included for maximum efficacy and provides superior performance to the current commercial product SABREX. This gave the formulations used in trial GH15, set forth herein, that were deemed highly effective.

A practical component of the present invention was to evaluate the current commercial product, SABREX (composed of strains K2 and K4), and to develop seed treatments products that improved on the capabilities of this product. The development of the strain or metabolite mixtures used in this study was based on the concept of Focused Microbial Diversity (FMD). FMD has the following components: (1) microbial strains each individually are rhizospheric and endophytically competent. In addition (2) we expect that metabolites are the specific triggers of changes in plant gene expression, so the concept of FMD also includes the triggering compounds. In such definition, FMD requires metabolites that give benefits for a period of months (for metabolites) or at least a season (microbes) and strains or metabolites that are effective when added as seed treatments at levels of about 70 mg/ha (microbes) or at less than 1 μl/seed (metabolites). Effective strains, metabolites or mixtures of the two are then combined into single treatments that are expected to provide better results than any of the components used singly. Since each component is strongly able to colonize plant roots and become an integral and long-lasting component of the plant (microbes) or to have long-term effects (both microbes and metabolites) substantial and beneficial changes in the plant phytobiome that lead to long-term benefits to plant performance are possible.

Initially, these organisms and metabolites were implicated in enhanced resistance to plant diseases. However, the capabilities of both microbes and metabolites have recently been shown to have much wider ranges of action. For example, *Trichoderma* spp. have been demonstrated to improve seed and seedling performance of aged seeds and to induce resistance to stresses such as water and drought stress (Mastouri, Bjorkman, et al., 2010, Mastouri, Bjorkman, et al., 2012). In both of these cases, alleviation of these diverse stresses are due in large part to amelioration of the toxic and negative effects of reactive oxygen species (ROS) that accumulate in plant under stress. In drought or salt challenged plants, levels of antioxidants in plants (ascorbate or glutathione) were unchanged but the ratio of reduced to oxidized forms increased in plants whose roots were colonized by *T. harzianum*, while the ratio decreased in plants under stress not containing the organism. The highest ratio was when both stress and the fungus was present. Moreover, both levels of enzymes catalyzing the cycling of oxidized to reduced forms of the antioxidants and expression of the genes encoding the enzymes all increased. Finally, the presence of the fungus reduced the toxic effects of methyl viologen, which strongly induces ROS formation. Thus, the effects of the fungus in part act as an agent to optimize ROS levels in plants.

All of these improvements in plant performance noted herein are energy intensive, and for specific microbes to induce these changes, the plants also must have improved photosynthetic efficiency (Shoresh and Harman, 2008). In support of the concept of an improvement in the basal level of photosynthesis are the following: there are many reports of enhanced leaf greenness as a consequence of inoculation with microbial agents (cf. (Harman, 2000). This is evidenced by results of gene expression and/or proteomic studies that demonstrate that photosynthetic elements are among those overexpressed. These include rubisco and photosystem II oxygen evolving complex protein (Shoresh and Harman, 2008, Vargas, Mandawe, et al., 2009). If photosynthesis is enhanced, then available resource such as starch should also be increased and this does occur (Shoresh and Harman, 2008). Substantiating the expectations that these changes directly affect plant photosynthesis was the demonstration that a strain of *T. virens* resulted in an increase of carbon sequestration in corn more than 60% (Vargas, Mandawe, et al., 2009).

Moreover, photosynthesis and photosynthetic machinery are highly susceptible to damage by reactive oxygen species (ROS). Stresses such as drought, salt, and flooding result in accumulation of levels of ROS that are highly damaging to them (Nath, Jajoo, et al., 2013). Even other otherwise optimal growing conditions, light in excess of its utilization in photosynthesis result in production of ROS, including the superoxide anion, that are detrimental to pigments, proteins and lipids.

Therefore, damage to photosynthetic systems occurs as a consequence of ROS accumulation that may be induced by stresses or even by otherwise optimal conditions at high light levels. This is of serious consequence, since photosynthesis is therefore the ultimate limiting factor in the growth of plants. Unfortunately, the best measured photosynthesis is only about 20% of the theoretical maximum conversion rates (which are 0.1 and 0.13 for C3 and C4 plants) and this has not noticeably improved through plant improvement efforts. Thus, yields have increased without improving the photosynthetic rate, which is the fundamental limiting factor (Long, Marshall-Colon, et al., 2015). The rate of increase in yield improvements of major crops has decreased in recent years, in part because the other inputs and improvements are becoming limited by the lack of improvement in photosynthetic efficiency (Long, Marshall-Colon, et al., 2015).

Yield potential (YP) of crop plants can be approximated as the product of the solar radiation received over the unit of land in a single growing season (Q), the efficiencies of the plant to intercept the radiation (E1), conversion of radiation energy into biomass energy (E2), and partitioning of the biomass into the harvestable parts of the plants (E3) (YP=Q·E1·E2·E3) (Long, Marshall-Colon, et al., 2015).

Modern developments in plant improvement, as exemplified by advances in the green revolution, have focused primarily on E1 and E3, while E2, a trait not easily evaluated in most breeding programs, has not been targeted. E1 is the proportion of available light intercepted by plant stands and is currently around 90%, while E3 has been improved by selecting varieties that convert more of their biomass into harvestable product rather than total biomass. For wheat, improvements in E3 were accomplished by semi-dwarfing genotypes that reduced the amount of biomass allocated to the stem relative to that incorporated into the grain. For corn (maize) E3 was enhanced by genetically limiting the number of ears per plant to one of a genetically predetermined maximum size, even though some genotypes have the potential to produce more ears/stalk or larger ears. The development of E3 strategies has been primarily to provide the greatest yields in plants where photosynthate is the primary limiting factor. For crops where maximum biomass is required, such as sugar cane and corn for silage, the need for improvement in E2 is particularly important. Further, if E2 was improved some of the standard dogmas of plant breeding—e.g, only one ear/stalk of corn, E3 strategies may be less desirable than is the case currently. Other E2 strategies are more common for field corn; ears may be determinate (of fixed size and one ear per stalk) or semi-flex or flex (ears are able to increase in size in response to additional plant resources, primarily photosynthate).

These data imply or indicate that both abiotic stress resistance and enhanced functional photosynthetic efficiency can be improved in crop plants by maintenance of an optimized redox potential in plants. This can occur through the ability of selected strains of *Trichoderma* spp. to colonize roots, and induce systemic changes in plant gene expression especially in the pathways and enzymes involved in antioxidant cycling and detoxification of reactive oxygen species such as the superoxide anion. This requires coordinated upregulation of the entire gene sets involved in these reactions.

Thus root colonization by selected strains of these fungi are expected to have numerous advantages to plant performance, including all of those noted earlier. The ability of the strains to ameliorate ROS to nontoxic levels is anticipated to have numerous benefits and these would be expected to result in improved plant performance and yield enhancement in the field. Moreover, based on earlier observations and in analogy with induced resistance to pathogens, we hypothesized that resistance to stresses such as drought are likely to involve gene priming events; i.e., where genes expressed more rapidly and at higher levels after a stressful event. These genes are poised for activity, perhaps through specific histone modifications to specific genes in the chromatin (Jaskiewicz, Conrath, et al., 2011).

Further, the capabilities of these organisms to improve at least field level photosynthetic efficiency (functional photosynthesis efficiency (FPE)) provide a greater reservoir of biomass energy (photosynthate) to plants. FPE is defined as the avoidance of loss of the already-low levels of photosynthetic efficiency due to ROS levels induced by stresses or even high light intensity. Of course, it may also be that not only FPE can be attained, but also total photosynthetic efficiency (TPE) can be improved, as suggested by the observation that the presence of a strain of *T. virens* resulted in a 69% increase in photosynthesis rate in corn (Vargas, Crutcher, et al., 2010). If improved levels of biomass energy are available through FPE or FTE induced by endophytic fungi, then it is possible that yields of important crops can be markedly improved. However, if plant productivity levels are limited by E3 strategies, i.e, matching of yields to currently expected levels of photosynthate, then alternative E2 strategies may be useful that have not been heretofore practical. Clearly, the genetics of plants are important in their response to plant symbiotic microbes, especially in determination of plant yield responses.

All of these strategies and alternatives positively affect the environment. For example, FPE or FTE have the potential to increase carbon sequestration, and the organisms also enhance nitrogen use efficiency (NUE) and thereby reduce the important greenhouse gases $CO_2$ and NO. In addition, greater NUE is likely to reduce water pollution from $NO_3$ and $NO_2$ from runoff from fertilized fields (Harman, 2011). If this potential is being realized, then greater total incorporation of C and N should be present in harvested biomass. Clearly, if greater levels of C or N are sequestered or incorporated into crop plants, then they are not present in either the atmosphere or waterways. The impact of annual crops on these environmental factors has not been seriously considered with annual crops because sequestered C or N are rapidly cycled back into the environment as the plant products are harvested and used. However, this does not take into consideration the biomass in roots, which is large and increased by the changed phytobiome that results from use of these organisms. The C and N contained within root biomass is slowly degraded and the organic materials and incorporated into organic materials in the soil. Thus, the soil become a reservoir for both of these elements and, with larger root systems, soil organic material, and therefore soil tilth and productivity, are enhanced.

Thus in one embodiment of the present invention, the system focuses on the early events of seed and seedling colonization of selected endophytic *Trichoderma* strains. The abilities of the same strains to alter tomato growth, photosynthetic efficiency and leaf greenness under stressful conditions in the greenhouse were evaluated as provided herein. To report results with corn to drought stress in the field and assess field experiment results using corn varieties that differ in their abilities to utilize photosynthate for either total biomass or grain weight the following data was obtained. Determinate ear varieties having little or no ability to increase ear or plant size beyond a genetically limited amount will not increase grain yields as much as varieties that have indeterminate ear and plant habits.

Enhanced FPE or TPE increase CO2 sequestration in field grown plants in some embodiments, where since the endophytic fungi increase root development, much of this sequestered carbon will be placed underground, where it will not be rapidly re-released into the air. Further, the increased abilities of plants to utilize nitrogen efficiently result in more nitrogen incorporated into the plant and less that is available to pollute water or air. Therefore, the total C and N incorporated into field grown corn was measured. Yield and photosynthesis interact strongly with nitrogen available to the plants. This study also examined the interaction of different corn varieties with nitrogen uptake.

The highly active products of the present invention also increase plant productivity and improve quality of fruits, vegetables, flowers or other plant products. Microbial agents applied as seed treatments or other methods of application have been shown to increase plant growth and development. In some embodiments, the most effective of these organisms colonize plant roots internally and induce beneficial changes in gene expression and that therefore give rise to changes in plant physiology. These alternations in plant physiology include coordinated up-regulation of entire biochemical pathways in plants. These changes comprise: reliable and consistent plant growth and yield promotion; enhanced root growth and development resulting in larger and deeper root systems; improved resistance to such abiotic stress including too little or too much water, salt and soil contamination; increased fertilizer use efficiency and especially nitrogen fertilizer use efficiency; and enhanced antioxidant levels in produce.

All of the effects noted above require energy, and can only occur if photosynthesis is enhanced. In one embodiment selected microbial agents efficiently improve photosynthesis. Beneficial microorganisms with the capabilities described above, in some embodiments, have been and are used commercially. Previous product may entail mixtures of a fungus in the genus *Trichoderma* and a bacterium in the genus *Bacillus*, e.g., sold as QUICKROOTS™. This product does increase yields, but in numerous replicated trials it was relatively inconsistent. However, the strains of *Trichoderma* spp. can be combined (different specific strain mixtures are present in the products sold for different crops). These products give the advantage just enumerated above, in some embodiments, and provide consistent yield improvements of about 8.5 bushels of maize per acre. In some embodiments, other crops give comparable results and include soybeans, rice, cotton, vegetables, alfalfa and other forage legumes, and small grains including wheat.

The present invention, moreover, concerns the strain *Trichoderma virens* NRRL B-50520, which was isolated from a chicken manure compost. It, along with two other fungi, was selected for their abilities to produce ammonia and amino acids from bird feathers because of its high levels of proteinase activity in certain embodiments. The ammonia and amino acids provide nitrogen to plants, while feathers themselves are broken down very slowly and do not provide immediate nutrients for plant growth. In other embodiments of the claimed invention, strain 50520 is exploited to release nutrients for plant growth.

In the present invention, the use of this strain is described as plant growth promoting agent in suitable embodiments. It provides superior plant growth advantages when compared to the prior art, including SABREX, which is among the most effective commercially available product for plant growth promotion. The present inventors have discovered that, the primary mode of action of the claimed invention is via seed treatment, with other applications and embodiments demonstrating efficacy with respect to foliar applications on various plant sources, such as, e.g., wheat. Since it is effective as a seed and as a foliar treatment, there are various other embodiments and applications that are effective, such as, e.g., including: applications as an in-furrow granule; application as a soil drench where the organism will come into contact with roots and colonize roots; application as a root treatment, e.g, during transplant operations; and as a component of liquid or solid fertilizers. In many embodiments, the organism comes into contact with roots and establishes a beneficial relationship with the plant leading to plant growth promotion.

Likewise, the present invention is also highly effective in control of various deleterious organisms including plant pathogenic bacteria, fungi and nematodes. Nematodes contain structural proteins (collagens) in the outer surface and in eggs. In other work, *Trichoderma* strains with high levels of effective enzymes that degrade proteins such as keratin (in feathers) or collagen are effective in control of plant parasitic nematodes (Sharon, Bar-Eyal et al. 2001), includes eggs and the worms themselves. Thus, the present invention includes claims to control of both nematode and plant pathogenic microorganisms.

Examples

The present compositions and methods will be understood more readily by reference to the following examples, which is provided by way of illustration and is not intended to be limiting in any way.

Materials and methods—Microbial strains. The *Trichoderma* strains used in this study included *T. virens* strain 41 (ATCC accession 20476; K1), *T. harzianum* strain RR17Bc (ATCC accession PTA 9708; K2), *T. harzianum* F11Bab (ATCC accession PTA 9709; K3), *T. atroviride* strain WW10TC4 (ATCC accession PTA 9707; K4), *T. gamsii* (formerly *viride*) strain NRRL B50520 (K5) and strain T22 (ATCC 20846). All of the strains except 41 and B50520 were prepared using the protoplast fusion process we have described earlier (Stasz, Harman, et al., 1988). Hereafter, these strains were described as K1 through K5 and T22 and all have been described previously (Harman, 2014, Harman, Bjorkman, et al., 2008, Harman and Lei, Pending, Harman, Taylor, et al., 1989, Smith, Wilcox, et al., 1990). All of these strains are used commercially except for K5. Also used is a *Bacillus amyloliqifaciens* strain isolated from alfalfa stems in Ontario County, N.Y. This strain also is strongly rhizosphere competent and it, like all of the *Trichoderma* strains used here, when added singly as seed treatment, strongly increases plant growth in greenhouse tests (data not shown and field results with corn, especially under stressful conditions; see tomato experiments). The strains are endophytically and rhizospherically competent, with data presented in this paper Quantification and observations of post-planting colonization of seedling by *Trichoderma* strains—Corn seeds of a commercial hybrid were treated with the designated fungal strains with conidial suspensions at 1×109 cfu/ml and used to treat seeds at the rate of 0.9 ml/kg for each organism and germinated on moistened sterilized blotters. Samples were collected at 0, 24, 48, and 72 hours post imbibition with one cm of root being collected where possible and chopped into one mm pieces. The 0 hour time point was collected as a root washing and at 24 hours the radical had either emerged or dramatically swelled and this nascent tissue was harvested. All samples were collected in 2.5% Tween 80. Total DNA was extracted using DNeasy Plant Mini 96 kit (Qiagen) on a QIAcubeHT instrument. Ten microliter Quantitative PCR reactions were set up using the Rotor-gene SybrGreen PCR kit (Qiagen) and 1 uM primers based on the *Trichoderma* sp. ITS region. Cycling conditions were as follows: 95 C 15 min; 10 touchdown cycles of 95 C 20 s, 65 C 20 s decreasing 1 C each cycle, 72 C 20 s; 35 PCR cycles of 95 C 10 s, 55 C 15 s, 72 C 20 s; and ending with a melt from 70 C to 95 C increasing 1 C/step. Quantification of *Trichoderma* DNA was accomplished by including a *Trichoderma* DNA dilution series in all PCR runs to establish a standard curve. A minimum of three technical replicates were performed per sample.

Effects of strains K1–K5 on stressed tomatoes—Seed of tomato (*Lycopersicum esculentum* L.) cv. Supersweet 100 were used in this study. Seeds were planted in a peat-vermiculite mix (Cornell mix) and a fertilizer was used for the pot experiments, which had the following properties: pH 5.98, NO3-N 55.6 ppm, NH4-N 13.9 ppm, P 15.3 ppm, K 110 ppm, Ca 67.0 ppm, Mg 71.1 ppm, S 131 ppm, B 0.103 ppm, Fe 0.480 ppm, Mn 0 0.661 ppm, Cu 0.071 ppm.

*Trichoderma* strains K1, K2, K3 and K4, as well as the combination of K1–K4 were applied to the mix as coating onto organic fertilizer granules. The granules were prepared by adding sufficient water to chicken feather powder to produce a slurry and then dissolving in this slurry in a solution of gelatin (7% w/v). The resulting slurry was spread in a sheet and air dried and the result was a flat brown sheet. This then was ground and sieved to provide particles of about 2 mm in diameter. These granules are composed totally of animal protein so the final nitrogen content was 12-14%. To this was added a slurry containing $10^{\wedge}6$ colony forming units (cfus) of each *Trichoderma* strain or the mixture of K1–K4, as liquid suspensions of conidia in a volume to avoiding obvious wetting of the granules. The goal was to obtain a granule that would have sufficient nutrients for growth of the test fungi; unless the fungi grow well they cannot colonize plant roots. It was found that addition of tapioca dextran (Crystal-Tex, National Starch) worked well (See FIG. 5A). Granules coated or not coated with the fungal strains in the presence of the Crystal Tex were added to the soil mix contained in 10 cm diameter plastic pots. Five seeds were planted per pot, and after emergence plants were thinned to three/pot. All plants were treated identically with full greenhouse watering for five weeks and then on one set of three pots per treatment, watering was reduced to maintain a soil water capacity of 60-70% of saturation (measured by repeated weighing of pots), and on another set of three pots, normal water schedules were maintained but with a solution of 75 mM NaCl. This provides three blocks of three pots (9 plants) of unstressed, water-stressed and salt-stressed plants. Stress conditions were continued for 30 days. Temperatures were maintained at 20° C. to 25° C.

Various parameters were measured at the end of the 30 day stress period. These included plant heights and chlorophyll content (on the tip leaf of the 5th set of leaflets) estimated using a chlorophyll meter (SPAD-502, MINOLTA CO., LTD. JAPAN). The estimates of chlorophyll content with such units appear to be equal to those obtained using more complex spectral reflectance indices and reflective of actual chlorophyll contents based on extractions (Casa, Castaldi, et al., 2015). In addition, photosynthetic efficiency was determined using chlorophyll fluorescence kinetics using a handy PEA (HansaTech) on the youngest fully developed leaf of per tomato plant. Leaves to be tested were dark-adapted for 30 min using the leaf clips (A preliminary experiment was conducted on tomato seedlings to determine the minimum period required for dark adaptation; data not shown). Determinations were carried out three to five hours after the start of the photoperiod. Several photosynthetic parameters were measured: minimal (FO) and maximal (Fm) fluorescence and the performance index (PI) are presented here since they were the most useful. Fv/Fm is a measure of the expression of the maximum quantum yield of primary photochemistry. The performance index is a parameter devised to quantify the effects of environmental factors on photosynthesis and that combines the three main functional steps taking place in PSII (light energy absorption, excitation energy trapping, and conversion of excitation energy to electron transport) (Strauss, Krueger, et al., 2006). PI was generated directly by software contained with the HansaTech apparatus. Both Fv/Fm and PI have been widely used as direct measures as a measure of biotic, abiotic or genetic interactions affecting photosynthesis (Christen, Schoenmann, et al., 2007, Ghotbi-Ravandi, Shahbazi, et al., 2014, Oukarroum, El Madidi, et al., 2007, Sheratmeti, Tripathi, et al., 2008).

Example 1—Colonization of germinating corn seeds by *Trichoderma* strains—Corn seeds treated with spores of *Trichoderma* strains K1–K5 and germinated on blotter paper showed clear differences in timing and vigor of germination. Total DNA isolated from either seed washings (ungerminated seeds) or roots from germinated seeds was used for qPCR detection of *Trichoderma* over the germination time course. All strain enhanced the growth rate of *Trichoderma* on germinating seeds. In particular, strains present in the seed treatment product SABREX LQ for corn, K2 and K4, peaked by 24 hours post imbibition from 1000 to 10,000 fold from 0 hours post imbibition. While the study reported here only extended to three days post imbibition, the qPCR data suggests an early peak in biomass followed by a decline to very similar levels by all strains. We speculate that this may be due to the system reaching a homeostatic point at or around this time wherein the plant root has reached a carrying capacity for endosymbiont support that is strain independent.

Example 2—Effects of strains K1–K5 on stressed tomatoes—The conditions of water and salt stress were relatively severe, although nonlethal, and decreased growth of tomatoes substantially. Plants in the absence of the *Trichoderma* strains and water or salt stress were only 60-65% as tall as those grown without stress. The presence of the *Trichoderma* strains, which are confined to the roots, reduced the growth reduction. For example, plants in the presence of the mixture of strains K1-K4 were 35% taller than similar plants without the strains when under water stress, while plants with the organisms under salt stress were 19% taller than ones with the stress in the absence of the organisms. Most of the microbial treatments gave an increase in plant height under stress relative to the nontreated stressed control; however, the older strain T22 was very similar to the control. In the absence of stresses, there was no difference in the height of tomatoes treated with the organisms.

Example 3—Leaf greenness (correlated with chlorophyll content) in plants in the presence of the fungal strains varied in the absence of stress, Strains K4 and the mixture of K1-K4 were greener, while those with K2 and K3 were lower and with T22 about the same as the control plants. However, in the presence of stress and the beneficial fungi, levels of leaf greenness increased markedly. Strains K1, K2, K4, T22 and K1-K4 gave values 40% higher than the nontreated nonstressed control, while with K3, the level of increase was about 20-25%. Photosynthetic measures based on dark-adapted chlorophyll fluorescence on the same plants differed according to the units measured. Fv/Fm, which measures the maximum yield of photosystem II (Ghotbi-Ravandi, Shahbazi, et al., 2014), was enhanced by the presence of any of the strains, regardless of the presence or absence of stress. This parameter was depressed in the presence of either stress, but even in the presence of stress, with any of the microbial strains, this photosynthetic measure increased to a consistent high level and was unaffected by stress.

A more complex measure of photosynthesis is the Performance Index (PI). This parameter integrates the main photochemical process, including density of reaction centers, absorption and trapping of excitation energy and electron transfer beyond plastoquinone (Christen, Schoenmann, et al., 2007, Lepedus, Brkic, et al., 2012). PI values for plants without the fungi were relatively low and were decreased even more in the presence of either stress. However, in the absence of stress, the presence of the fungi increased the PI levels, and in the presence of stress, the PI values were much higher, by 80 to over 100%, relative to the nontreated nonstressed control and even more relative to the stressed controls. Thus, this complex measure of overall photosynthetic function was enhanced and activated by the combination of stress and the organisms, but decreased in stress in the absence of the microbes.

Example 4—Field observations—In Illinois, there was a very severe drought, with widespread crop failure. At this time, some seeds of corn were treated with K2+K4 as the commercial product SABREX™. Differences in drought susceptibility were obvious in the mature crop, even though (a) the plants were approximately 2 meters tall and (b) the seeds were treated several months before the drought became acute. Differences were obvious in plant growth, in ear growth and development, and in root development. This field observation is consistent with the greenhouse observations reported in the previous section on tomato and in other work on that plant (Mastouri, Bjorkman, et al., 2010, Mastouri, Bjorkman, et al., 2012).

Example 5—Field experiments GH14—Field trials of several seed treatment microbial mixtures and formulations were conducted. These trials recorded a number of variables. First, plant heights were measured at two different times; on August 5, just before tasseling, there was a large difference (116 cm in the control vs about 150 cm for the most promotive treatment) but by the time of harvest, there was no difference (See Table 1). The difference is that corn is genetically programmed to about a certain height but the stem diameter and general robustness of the plant reflects this early growth advantage. Roots are also much larger and more robust with the most effective strains used as seed treatments. This increase in above-ground plant robustness resulted in an increase of more than 10 t/ha in total biomass (silage) at the time of harvest (just after the second plant height measurement), or just a little more than a 30% increase in plant biomass (silage). However, the grain yield increase was somewhat lower, with about a 24% increase.

The most effective strains were *T. viride* strain K5 plus *Bacillus amyloliquefaciens* in the presence of a humic acid containing adjuvant, K5 alone, and *T. harzianum* strain K2 plus the humic acid addition. These gave improvements in yield over the commercial product SABREX, which is K2 plus *T. atroviride* strain K4 (SABREX). These seed treatment formulations also resulted in a reduction in northern corn leaf blight (causal agent *Exserohilum turcicum*), but corn rust (*Puccinia sorghi*) increased on the plants grown from the treated seeds.

Based on the results reported above with tomato, it was expected that there would be a net increase in photosynthesis in the corn trials. We therefore measured the total C content of the biomass that was harvested. It was also expected an increase in nitrogen incorporated and so total N in the biomass was measured. Neither the C nor N content percentages were increased; however, there was an increase in the total C and N per hectare because the biomass increased markedly (See Table 2). Of course, the biomass harvested was only the above-ground portions of the plants, and there is a very significant amount of subterranean roots biomass. It is therefore estimated the total plant biomass as 2× the level harvested above ground. In so doing it was discovered that there were up to 4 tons of C/ha increase over the control and up to 145 kg/ha of additional N incorporated into the plants that grew from the treated seeds (See Table 2).

Field experiments GH15—The results of experiments GH14 suggested that even if corn is more robust, not all of this is translated into grain yield. Thus, there might be a genetic component to high grain yields that would not take full advantage of the increased plant growth and development. Commercial corn varieties differ in ear character: some are determinant, which means that a single ear of a certain size will be produced per stalk regardless of the amount of photosynthate that is available to the plant, others are semi-flex, which allows some increase in the size of ears depending on plant resources, while still others are full flex, which allows for plasticity in the size of ears, with larger ears depending on the photosynthate resources. Therefore, in 2015, we conducted trials on five different commercial corn hybrids that differed in this character (Table 3-appearance of plant growth differences).

The GH15 field season was very wet, receiving 22.2 cm of rain during the month of June at the research plot location, and the lower end of the field comprising the entire planting of a single variety was flooded for about 3 weeks. Through mid-June all of the plants were very small, only a few cm high. After this, growing conditions improved markedly, but the plants grown from seeds treated with the biological agents were much more robust and recovered from the flooding episode much more fully than those without the agent. There was a substantial increase in growth by the end of July with plants treated with the microbial agents and a large increase in biomass which also translates to grain yield (Table 3).

The seed treatments overall gave different results across varieties. In general, the SABREX treatment gave the greatest response. The seed treatment with a formulation of the present invention named OMEGA, which contains a *Trichoderma* metabolite, but no living organism, gave very good results as well. Mixtures containing both microbes and the OMEGA treatment provided lesser responses. Quite apart from the flood-stress interaction, there was a substantial difference in growth and development of the different varieties in reaction to the biological seed treatments. One variety, 6490, responded with a very large increase in biomass (up to 2×). Other lines responded with lesser increases; in general, lines developed for grain as opposed to dual purposes gave lesser, and nonsignificant, increases in plant biomass (Table 3).

The lines that provided the greatest yield increases also increased C sequestration and N incorporation into plants. The greatest C sequestration (with variety 6490) totaled 25.6 t/ha, and plants grown from seeds treated with SABREX, which was a doubling of that with the untreated lines. The total N incorporation was 1056 kg/ha, which is about a 3-fold greater level than that total amount of N from soil. The various lines responded differently, with less of a ton increase with variety 5469 (See Table 4).

Discussion—microbial strains.

Example 6—The efficacy and capabilities of microbial agents for plant agriculture is, in our experience, totally strain specific. We have been unable to generalize regarding species level criteria—just because one strain of *T. harzianum*, for example, is effective for a particular function is no indicator that another strain of the same species will be. In this work, we have tested and evaluated the function of three strains of *T. harzianum*, one strain of *T. atroviride*, one of *T. virens*, one strain of *T. gamsii*, plus a strain of *Bacillus amyloliquifaciens*, either singly or in combination. T22, K1, K2, K3 and K4 are all components of commercial products that are in wide scale use on one crop or another. T22 and K1 were isolated more than 30 years ago. T22 is widely and successfully used, especially in horticulture and greenhouse applications (Harman, 2000) (www.bioworksinc.com), but on corn as a seed treatment, its performance was found to be inconsistent (Harman, 2006, Harman, Bjorkman, et al., 2008). For this reason, K2, K3, and K4 were developed and widely tested and used in the field. Further, for commercial applications, mixtures of strains (e.g., K2 and K4 for corn (SABREX LQ™ for corn)) were produced for use with different crops, while K2 and K3 have been used for wheat seed treatments (SABREX LQ™ for wheat). Conversely, K1 is used for soybean treatments in combination with *Bradyrhizobium* strains (e.g. EXCALBRE™); field testing of K1 with corn indicates that this strain has adverse reactions on this crop. The selection of these mixtures is largely empirical but based on the concept of FMD described earlier. The use of multiple strains has given more reliable results than a single strain.

This first criteria that has evolved over decades of testing is that the strains need to be able to colonize roots (i.e., be rhizosphere competent), which by definition means that they need to grow with and provide benefits from a single application, for the life of an annual crop. The data in the experiments reported here plus earlier work (Harman, 2000, Sivan and Harman, 1991), indicates that all of the strains or strain mixtures used in the present invention have this ability.

Beyond that, the data set forth herein indicate that the strains have a remarkable ability to proliferate rapidly as seed treatments to the roots of developing corn seedlings. Within 48-72 hr, roots are strongly colonized and the biomass of the added strains increases up to 10,000 fold within this time period. The level of colonization differed between strains; K2 proliferated to the highest level. This rapid ability to colonize radicles emerging from corn seeds may be a component of its high abilities to improve corn growth and have affected its empirical selection as a reliable improver of seedling performance. Probably early capability in colonization affects its overall performance. It is also noteworthy that some strains clearly colonized seedling radicles and sporulated within the root structure.

However, abilities to colonize roots rapidly and establish an endophytic relationship are not the only determinants of overall efficacy. Once they become established in roots, they establish a chemical communication with the plants they colonize that is dependent upon production of specific triggering molecules by the root-embedded microbe that reprogram plant gene expression (Djonovic, Pozo, et al., 2006, Shoresh, Mastouri, et al., 2010, Waller, Achatz, et al., 2005, Yedidia, Benhamou, et al., 1999). These triggering molecules induce signaling cascades that result in system-wide, long-term induction of changes in plant gene expression (Alfano, Lewis Ivey, et al., 2007, Shoresh, Gal-on, et al., 2006, Shoresh and Harman, 2010). More than 100 plants genes have shown to be up-regulated and changes in above-ground plant gene expression is frequently greater than in roots, where the root colonizing microbes reside (Shoresh and Harman, 2008).

Some strains of *Trichoderma* clearly have evolved/can be characterized as endophytic plant symbionts (Harman, Howell, et al., 2004), but most wild strains lack this capability. It is worthwhile to note that the total numbers of *Trichoderma* in typical field soils are 10,000 fold or so higher than the levels added with the seed treatments in this paper, but these native strains are without observable effects on plant growth. Thus, while most soil-inhabiting strains have little effect on plant performance, addition of specific endophytic plant symbiotic strains can make a large difference.

*Trichoderma* strains are not the only organisms that include strains that have qualitatively similar abilities to enhance plant performance. Fungi in the Sebicales, such as *Plriformaspora indica*, mycorrhizae and plant-growth promoting rhizobacteria all include at least some strains that can be considered as endophytic plant symbionts and all can increase plant growth and induce other changes within the plant that contribute to plant performance, such as resistance to diseases, resistance to abiotic plant stresses, and improved nitrogen use efficiency (Shoresh, Mastouri, et al., 2010). They also frequently are confined to roots but induce systemic changes in plant gene expression, which implies the production of triggering compounds. However, it probably impossible that these genetically very diverse groups of microorganisms express the same triggering molecules. For this reason, even if their qualitative effects are similar, their specific mechanisms are likely to differ. As an example, both *Bacillus* spp. and *Trichoderma* strains produce amphiphilic metabolites that are very active at low concentrations (less than 1 µmole), but they are chemically dissimilar. In *Bacillus* these include lipopeptides; production of the lipopeptide surfactin is strongly implicated in induction of systemic plant disease resistance in plants (Cawoy, Mariutto, et al., 2014). In *Trichoderma*, hydrophobic proteins probably have a similar role in inducing resistance and other plant responses.

The data reported here indicate that we have succeeded in developing effective strain combinations and formulations. Greenhouse tests on tomato demonstrated the efficacy of each individual strain on parameters leading to improved photosynthetic efficiency and leaf greenness especially in the presence of water or salt stress. In previous research, we demonstrated that the presence of strain T22 resulted in overexpression of a variety of genes and gene products involved in antioxidant cycling or direct degradation of ROS (Mastouri, Bjorkman, et al., 2010, Mastouri, Bjorkman, et al., 2012). This process requires coordinate upregulation of the entire pathways such as those involved in redox control and not just upregulation of single genes at random. Therefore, effects of the beneficial organism include maintenance of an optimized internal redox environment (OIRE) in the plant across a wide variety of environments and that OIRE induced by these endophytic plant symbionts is of fundamental importance in the plant benefits observed in this paper.

Moreover, the systems leading to stable OIRE appear to be inducible if both stress and the beneficial organisms are present. In the presence of stress and the absence of the microorganisms, all of the parameters except leaf greenness decreased. However in the presence of both stress and the beneficial fungi, all of the parameters increased over either stress in most cases increased, sometimes markedly so. However, in the absence of stress neither leaf greenness nor PI improved, this suggesting the operation of an inducible system analogous to the priming response frequently noted by these same fungi in induced resistance to plant diseases (Goellner and Conrath, 2008).

In field trials, the combination of K5+As2, and K5 alone, gave superior results to SABREX. In certain GH15 tests, these strain mixtures, in the presence of a formulation containing humic acid and 1-octene-3-ol also provided an important improvement over SABREX. Surprisingly, a formulation containing the formulation and 1-octene-3-ol with no microorganisms provided very good results as well, even though each seed treated contained less than 1 µl of this metabolite of Trichoderma. These results strongly imply the chemical can itself induce relatively long-term changes in plant gene expression, perhaps through modification of the structure of plant chromatin. Various chemical plant elicitors of plant disease resistance have been shown to induce chromatin modifications on defense genes normally found of active genes even though the genes themselves are not expressed. These changes result in histone modification patterns in the chromatin the allow the genes to completely and rapidly expressed when properly stimulated (Jaskiewicz, Conrath, et al., 2011), resulting in reprogramming of plant gene expression (Waller, Achatz, et al., 2005). In this circumstance, the specific mode of action for the induction of scores of genes in the presence such agents would comport with plant chromatin-histone modification, which would elucidate the incongruence of extremely low levels of compounds such as 1-octene-3-ol having effects upon plant performance for months after application.

Example 7—Effects of Trichoderma strains on photosynthesis—As indicated herein there are a large number of benefits to the use of beneficial microbial strains and metabolites on plant performance. However, essentially all these benefits require energy—there is an energy/fitness cost even to physiological responses such as induced resistance (Deitrich, Poss, et al., 2006). Of course, the energy requirements for enhanced shoot and root growth demonstrated in this work also require large amounts of energy and the only source for energy in plants is photosynthesis. Therefore, if the observed effects are correct, photosynthetic rates and capabilities of plants must increase (Shoresh and Harman, 2008).

There are numerous reports that Trichoderma strains, and no doubt other beneficial microbes and metabolites, do have this capability. With the present invention, leaf greenness and Fv/Fm, a measure of the maximum quantum output of photosystem II also increases. All of these measurements and observations are indications that the total photosynthetic capability of plants colonized with strains of Trichoderma increases relative to noncolonized plants. By way of comparison, another endophytic organism that improves plant performance lacked the ability to improve the quantum output of photosystem II in the absence of drought (Sheratmeti, Tripathi, et al., 2008). The results of these studies on tomato were largely confirmed by the field trials with corn; the remarkable increase in carbon sequestration with some lines from the GH14 and GH15 tests, which demonstrates and enhancement in photosynthetic capability in corn, but there appears to be a strong varietal difference.

Example 8—The relationship between photosynthesis and resistance to stress—As already discussed, stresses, such as drought, salt, flooding and biotic stress give rise to highly damaging levels of ROS. A principal reason for the tan color of the control plants is probably is due to degradation of photosynthetic and other pigments by ROS. Thus, the maintenance of OIRE in plants is very important to plant growth and yield. OIRE will maintain FPE at a maximum level.

Photosynthetic systems (as well as other systems and pathway in plants) are damaged by stresses such as drought, salt and heat even more than by over-excitation by light. The performance index of barley photosynthesis (a measure that integrates several different aspects of photosynthesis) was reduced by 14 to 28% under mild and severe drought stress in a drought resistant cultivar and by 23 to 49% in the same two conditions in a susceptible cultivar. This reduction in measured photosynthesis was accompanied by decreases in chlorophyll content, carotenoid content and levels of the protein D1 in chloroplasts (these are critical pigments and a crucial structural protein in photosynthetic reaction centers, respectively). These changes also were associated with changes in stomatal conductance and CO2 assimilation rate, which are other critical measures of photosynthesis. All of these changes were indicative of drought-mediated damage to the photosynthetic systems in the drought affected plants. Resistant plants were more able to repair damage to these systems, a trait associated with higher levels of the plant antioxidant α-tocopherol that detoxifies ROS. Under conditions of stress, the levels of α-tocopherol increased in the resistant, but not the susceptible line.

Improvements in FPE by the various microbes and the metabolite used in this study are obvious. In tomato direct measurement of especially PI demonstrated this. In addition, in the field studies of GH14 and GH15, the levels of carbon sequestered ("C sequestration") increased markedly as a consequence of the seed treatments. It is also evident that different strains and formulations have similar effects. In tomato, all of the strains improved leaf greenness and photosynthetic measures, but not to the same level. Further, none of the components of the SABREX treatment are present in the K5As2 OMEGA treatment, and the OMEGA alone (a.i. 1-octene-3-ol) also improved C sequestration on an area basis (See Table 2). This improvement in C sequestration, which must, or at least primarily, must arise from photosynthesis. It is also evident that this increase in C sequestration does not result from an increase in C levels on a percentage basis, but occurs as a consequence of total assimilation over the entire area of the planting. This suggests that, at least at the end of season, the assimilated carbon is converted into plant biomass (which in corn is silage yield).

However, the conversion of grain yield as a consequence of larger plants was not totally reflected in grain yield. There are commercial maize genetics variants, for ear genotype including flexible, fixed, determinant, indeterminate and prolific. Determinate and fixed ear types are limited in their response to environment. Flexible and/or indeterminate ear types, by contrast which can adjust to growing conditions by changes in ear size. Varieties or lines that can expand both numbers of rows of kernels and length according to environmental conditions are available.

It appears the variety used in GH14 trials were fixed in kernel row number and length. A more plastic variety for this character may be useful; corn genetics will affect the increase in yield that we will obtain. Therefore in GH15, five corn varieties were examined that differ in this character and the flex ear variety responded more strongly than the semi-flex or determinate varieties.

There was a difference in the reaction of corn to microbial agents in GH14 vs GH15. In GH14 the single line used responded to give somewhat better results with K5As2+the adjuvant used relative to SABREX. In GH15, SABREX was clearly the most effective treatment. This difference may have occurred because of changes in the formulation. In GH15, 1-octene-3-ol was added to the K5As2 formulation while in GH14 this component was not included. K5, As2 and OMEGA all gave positive results when used alone, and in the GH15 trials, the chemical was used in the OMEGA formation also gave very positive results when used with microbials. However, the combination of these individually plant promotive effects may have given a negative interaction when used in combinations. Thus, components of FMD must be tested in combination when synergistic positive effects are suspected.

In addition, the results of especially GH15 demonstrate that nitrogen strongly interacts with the corn variety×microbial combinations. It required much more N to produce the yields of especially 6490+SABREX than other varieties or the controls (Table 4) or than was added as N fertilizer to the plots. These results indicate that varieties may differ in their abilities to take up large quantities of N from the soil in the presence of the microbial agents, so the interaction of variety×microbial agents×nitrogen are vitally important. It also suggests that much higher yields may occur in the presence of the strains but that, for many varieties, more N may need to be applied than the norm. Thus, the corn variety/genetics×microbial strain×nitrogen fertility needs to be examined in detail.

Example 9—Environmental and food security implications—The total net emissions (after correcting for sequestration by plants and other methods of removal) of CO2 from human activities totaled about 33 billion tons in 2010, with another 2 million tons CO2 as nitrous oxide. Clearly many activities need to occur together to reduce this accumulation of global greenhouse gases since they are rapidly changing Earth's climate and making the globe less hospitable to a growing population (http://www.epa.gov/climatechange/science/indicators/ghg/global-ghg-emissions.html).

Certainly plants need to be better adapted to stresses such as drought and flooding. It is therefore an exemplary embodiment of the present invention that root colonization by beneficial microbes can improve the abilities of plants to cope with environmental changes and stresses. It may be that plant genetic alterations can also provide such benefits, but the changes in stress resistance by our organisms and metabolites are immediate and do not require plant genetic manipulation of any kind. The endophytic organisms alter gene expression across a diverse plants in ways that are predictable and that permit the plant genomes to express pathways that give rise to strong resistance to stresses.

It is also true that there needs to be an increase in food for a growing population. By 2050, there will be an estimated 9 billion people on Earth, which is 2 billion more than the current population (Taylor, 2015). The improvements in yield and in resistance to stress shown here are attractive components to meeting challenges both from a changing climate and in simply providing more food of one of the most important food crops in the world.

Beyond this, these systems are appropriate for removal and sequestration of CO2 from the air. Table 2 demonstrates that significant amounts of Carbon are sequestered—in 2014 the largest plants sequestered an estimated 17.2 tons of C/ha with 4 tonnes more in the presence of K5As2 than in its absence, while in 2015 the increase was even larger—up to 25.6 tons with the most efficient variety.

This 17.2 or 25.6 tonnes was calculated from the actual measured % C in the above-ground biomass multiplied by 2 to account for the C contained in roots. If there are up to 25.6 tonnes sequestered in corn, this would seem to be a useful tool for combatting global warming. The dogma at the present time is that annual crops are not useful for long-term C sequestration because the crops are harvested and utilized, which results in re-release of carbon into the air. However, this does not take into consideration the roots of plants. It would be expected and is necessary for roots to contain a similar proportion of the sequestered C to that in above-ground parts, and our estimation of total C assumes that 50% of the total biomass is subterranean. However, rooting differed markedly in corn between treatments (Table 1, FIG. 3, of this section).

Additionally, in earlier studies with seed treatments with T22, the numbers of corn root intercepts on a soil surface exposed adjacent to (within 15 cm of the stalks) revealed twice as many root intercepts with the treated as opposed to the untreated plants 25 to 75 cm below the soil surface (Harman, 2000). The results in this paper demonstrate the proliferation of near-surface roots and the earlier study demonstrates that rooting depth and density are both increased.

Taken together, these data demonstrate that the biological treatments described in present invention markedly increase roots in soil as well as increasing above-ground yield parameters. Roots, of course, are not harvested in corn and remain in the soil where they gradually decompose into soil organic matter. Thus, the soil becomes a reservoir for sequestered C, and as the roots decompose, soil organic matter will increase and soil organic matter is an important component of improved soil health and quality. Thus, according to the present invention C can be sequestered and soil quality improved at the same time.

The levels of C sequestration o the present invention are significant. Table 4 demonstrates a total C sequestration in the best corn treatments of about 25 t/ha. This is, of course, just C, and the total CO2 represented by this figure is 91 t/ha of CO2. If it is assumed that 50% of this total is in relatively long-term storage in soils, then about 45 t/ha would be removed and stored in this system. There were about 100 million ha (39 billion bushels/300 bu/ha yield) of corn harvested in 2014 (http://www.worldofcorn.com/#), and so at 91 t/ha, the total that could be removed using this system is about 9.1 billion t worldwide. If 50% of this is represented by roots in soil, which is reasonable fraction, (about 14%) of the total CO2 net emissions of 33 billion tons in 2010. Of course, not all of the corn will be treated with our biological systems, but on the other hand, similar results could be expected for other crops especially widely planted legumes and small grains including wheat and rice.

Beyond this, total N incorporated into the corn in the 2014 plots was substantially greater (1056 kg vs about 563 kg) with the treated than in the nontreated corn. Nitrogen applied to corn as fertilizer can be released into the environment, either as gaseous NO or as NO3 in solution. In the first case, the NO released becomes part of the greenhouse gas mixtures that lead to global warming. In the second, NO3 or NO2 in ground and surface waters is a significant component that leads to eutrophication of waterways and the formation of "Dead Zones" in estuaries where excess nutrient loads from rivers leads to excessive plankton growth and leads to anoxia where organisms cannot survive. Clearly, if applied N is taken up by plants, this N is no longer available to pollute either air or water. The amount of total N incorporated into plants is about 3× that applied, suggesting a strong ability of some strains to 'mine' nitrogen from soil; deeper rooting and greater exploration of the soil volume may account for at least a portion of this increase. However, some lines were unable to increase N uptake nearly as much as variety 6490. With these lines, uptake of N was greater than with 6490, but the increase in N uptake was less. This suggests that to achieve maximum success either in yield enhancement or C sequestration, more N may need to be applied. This is unlikely to increase water pollution since the deeper rooting and capabilities of the plants grown from the treated seeds is likely to be enhanced over untreated plants.

In every case with corn over the two years of field studies, more N was incorporated into the corn than was added from the N fertilizer application. This indicates that corn itself can harvest residual N from soil, either from soluble forms or most likely from organic matter in the soil. This, however, is in large part returned to the soil in the form of unharvested roots and other vegetative debris. The net effect of at least the most effective treatments would be to enhance soil organic material and thereby soil health.

These data suggest that the treatment of plant seeds with selected beneficial microbes or metabolites could be a cost-effective method of reducing levels of atmospheric green gases. If it was employed as a carbon cap trading system, then verification and validation of the efficacy of the treatment would probably be necessary. Recent advances in remote sensing from drones or satellites can record multi-spectral images that can both measure plant leaf characteristics including ones that can measure higher levels of photosynthesis and chlorophyll content, and soil characteristics including organic matter. The former (normalized vegetation density index) could be used as validation of the efficacy of the treatment, and the latter could be used for multi-season evaluation of the prediction of higher organic soil content produced by the treatments. These remote systems could be used in conjunction with application of the microbes herein, especially if these microbes were used with plant genetics (e.g., flex ear corn), for validation, modeling and verification of the processes just described. Modeling of plant growth parameters using remote sensing to predict yields and other parameters from the complex interaction of variety×microbial strain×nitrogen fertility levels is probably essential.

Field experiments—field experiment were established on corn (Zea mays) near Phelps, N.Y. in GH14. Seeds of a transgenic, glyphosate-resistant commercial hybrid, A91-92R were obtained from Albert Lea Seeds, Albert Lea, Minn. The seeds were commercially treated with Acceleron™ (ACCELERON), a pesticide mixture containing ipconazole, metalaxyl, trifloxystrobin (fungicides) and clothianidin (insecticide). Seeds were over treated with a liquid formulation mixture of K2 and K4, which is the commercial product SABREX LQ, according to the manufacturer's directions. Other seeds were treated with a commercial blend of a humic acid product and minor nutrients, together with K2, K5+As2, or K2+As2. The fungal strains used were a liquid suspension of conidia at $8\times10^8$ cfu/ml, and the As2 concentration was $8\times10^9$ cfu/ml. The microbial suspensions were used to treat seeds at the rate of 0.9 ml/kg for each organism. This is the same *Trichoderma* seed treatment rate as is recommended with the SABREX product. Preliminary experiments have demonstrated that all of the organisms used in the overtreatment are stable in the presence of the chemical pesticides (data not shown).

Plots were established on a sandy loam soil with moderate yield potential. These trials were conducted in a replicated block design with four replicates. Each treatment+replicate consisted of four rows 76 cm apart and 6 m long planted in a north-south orientation. Seeds were planted June 17 following a cool wet spring, silage harvest was September 15 and grain harvest on or about November 20. The first killing frost was in the last week of October. Weeds were controlled with glyphosate herbicide following the manufacturer's recommendations. Fertilization at the time of planting was with 46 kg of actual N/Ha in a 19:19:19 formulation. This was followed with a side dressing of 96 kg in mid-July as a surface broadcast application. All harvest for yield was only in the middle two rows. For grain yield, the middle 4.6 m of the rows were harvested and for silage the northern 2.3 m was harvested. For root measurements and other destructive sampling, plants were dug or otherwise harvested from the outer rows away from areas that would be harvested. Plant densities were not significantly different between treatments and was about 63,000 plants per Ha. Plant growth was measured throughout the season. Weights of silage and grain were collected after harvest, and the % nitrogen and carbon were assayed by a commercial service (A&L Laboratories or the Cornell Nutrient Analysis Laboratory.

Field experiments (GH15)—Field trials were conducted again in GH15. The data in GH14 strongly suggested that grain yields were limited by the genetic limits of the variety used. Therefore, in GH15 five varieties of corn were tested that include varieties that are described by the supplier with ear types as determinate (2 varieties), semi-flex (2 varieties), and full flex (1 variety). These were provided by the Chemgro Company are designated as 5469 RSX, 5018 G3 (determinate); 5245 RDP, 5455 RDP (semi-flex) and 6490 (full flex). We hypothesized that since determinate, semi-flex, and flex ear types differ in their abilities to translate improved biomass resources (photosynthate) into grain, that the ratio of grain to biomass yield would differ if the seed treatments (a) resulted in an increase in photosynthetic resources, and (b) that the varieties differ in their abilities to utilize photosynthate. All seeds used in the experiments were treated with an insecticide/fungicide mixture (Cruiser Maxx 250, Syngenta Crop Protection) that contains thiamethoxam, fludioxonil, mefenoxam, azoxystrobin, and thiabendazole.

Prior to planting subsamples of each variety were treated with SABREX LQ according to the manufacturer's direction. Addition treatments to separate subsamples were a mixture designated OMEGA, which contains 20 g of humate (Leondarite shale), 5 g of yeast extract, and 100 µl of 1-octene-3-ol (Sigma Chemical Co.) all suspended in 1 L of water, and then the pH was adjusted to 6.2. This mixture was applied at the rate of 0.65 ml/kg of seeds. This mixture was developed to provide a chemically defined replacement for the humate material used in 2014. A low concentration of 1-octene-3-ol (mushroom alcohol), which a volatile metabolite of Trichoderma strains, was included because preliminary experiments indicated it was a potent plant growth promoter and because it induces resistance to plant diseases as also been reported by others (Morath, Hung, et al., 2012).

In addition other subsamples of seeds were treated with OMEGA plus K5As2 or OMEGA plus K2As2. The microbes were added at the same rate indicated for the GH14 trials. This trial was located on a loamy clay soil near Waterloo, N.Y. Plots were arranged by variety across the field as two rows 22.5 m long. Each treatment×variety was harvested for silage and grain. For this harvest, each set of rows was divided into four blocks each 1.8 m long for silage harvest interspersed with four blocks each 3.6 m long for grain harvest. In addition, the area of the plots received intensive rain of more than 20 cm over a three week period just after seedlings emerged in the plots (the last week of May through the first two weeks of June). The plots were laid out such that for this entire 3 week period a portion of the field was either saturated or, through much of the time, completely submerged. This area of the field coincided almost exactly with that planted with 5245 RDP, and was relatively uniformly flooded. Thus, the trials with this variety afforded a good opportunity to examine the ability of the seed treatments to assist the corn in recovery from flooding stress. The remainder of the varieties were on higher ground and so were not subjected to this stress.

Harvest and analyses of data were as described for the plots in GH14—Example 10—Data analysis qPCR A per experiment standard curve of Trichoderma DNA was calculated by the Rotor-gene Q series software and all experimental samples were compared to this to determine the quantity of fungal DNA present. Fold increase over the untreated control was calculated from these data and plotted on a log scale versus time. Field data Yield, biomass, and other characters measured during the GH14 and GH15 growing seasons were analyses using alpha=0.1 for ANOVA and Least Significant Difference tests and the analytical systems described in the tables.

TABLE 1

Growth parameters, disease ratings and yields of corn treated with different strains or strain mixtures in GH14.

| TRT | Ht on Aug. 5, 2014 (cm)[1] | Ht on Oct. 20, 2014 (cm)[1] | Stalk dia. on Aug. 5, 2014 (mm)[2] | Shoot wt on Aug. 4, 2014 (g)[3] | Root wt on Aug. 4, 2014 (g)[3] | Corn leaf rust (%)[4] | Northern leaf blight (%)[4] | Grain yield (tonnes/ha)[5] | Silage Yield (tonnes/ha[6]) | % inc over control-silage | % inc over control-grain |
|---|---|---|---|---|---|---|---|---|---|---|---|
| K2AS2 MJ | 152.5a | 86.2a | 16.8a | 558a | 134a | 4.33b | 5.0bc | 11.7a | 62.2ab | 19.2 | 20.6 |
| K5As2 MJ | 145.9a | 87.5a | 17.2a | 522a | 133a | 4.3c | 4.6c | 12.0a | 68.6a | 31.4 | 23.7 |
| K5 MJ | 135.4ab | 85.5a | 16.8a | 452ab | 95b | 5.4a | 5.44bc | 12.0a | 62.5ab | 24.9 | 23.7 |
| SabrEx LQ | 122.5b | 84.3a | 16.4a | 363b | 69bc | 4.3b | 6.1b | 10.8ab | 59.5b | 13.9 | 11.3 |
| Control | 116b | 81.3a | 14.7b | 342b | 56.5c | 3.81bc | 8.0a | 9.7b | 52.2c | | |

Numbers followed by dissimilar letters within columns are significantly different at P = 0.10 (Duncan's NMR). There were 4 replicates/treatment in a randomized plot design.
[1]Average height of 10 plants from the center of the plots.
[2]Stalk diameter at ground level measured, average over 10 plants/plot.
[3]Average weight of shoots or roots from 10 plants/plot from outside the harvested area.
[4]Corn rust and leaf blight (average across 20 plants/plot) estimated by the % of leaf area with disease.
[5]Average grain yield across replicates calculated from bu/acre. The test weights were consistently 53 lb/acre.
[6]Average silage (total biomass) yield per ha at 70% moisture content.

TABLE 2

Biomass, and carbon and nitrogen contents of corn harvested in GH14

| Treatment | Dry wt (kg/ha) | % carbon[1] | % nitrogen[2] | carbon sequestered (t/ha) | Nitrogen incorporated (kg/ha) | Total C, shoots and roots (t, est)[3] | Total N, shoots and roots (kg, est)[3] | Net increase C over control | Net increase N over control |
|---|---|---|---|---|---|---|---|---|---|
| K2As2 MJ | 18660 | 42.31 | 1.73 | 7.9 | 323 | 15.8 | 646 | 2.6 | 83 |
| K5As2 MJ | 20460 | 42.18 | 1.73 | 8.6 | 354 | 17.2 | 708 | 4 | 145 |
| K5 MJ | 18750 | 42.4 | 1.78 | 7.9 | 334 | 15.8 | 668 | 2.6 | 105 |
| SabrEx | 17850 | 42.8 | 1.8 | 7.6 | 321 | 15.2 | 642 | 2 | 79 |
| Control | 15660 | 42.4 | 1.8 | 6.6 | 282 | 13.2 | 563 | — | — |

[1]Total C was determined at the Cornell Nutrition Analytical Laboratory using and automated combustion method via thermal conductivity.
[2]Total N was determined by A&L Analytical Laboratories Inc, Memphis, TN using AOAC method 4.2.08
[3]Total shoot and root C and N was estimated by assuming that roots make up 50% of the biomass of corn.

TABLE 3

Field conditions and yield data from GH15 plots. Each variety was in a separate block and so means can only be statistically compared within varieties. There was an elevation difference of about 5-10 m in the field, and the varieties are arranged from the lowest-lying to the highest lying plot. Just after seedlings emerged, the area received about 25 cm of rain in three weeks and for that period of time, the seedling in the lowest lying (5245) plot were submerged, as was the adjacent end of the next plot. Thus, this part of the experiment is a test of the abilities of the treatments to assist plants in recovery from this stress. Foliar diseases were not seen in these plots. The seeding density was provided to give 80,279 plants/ha for all varieties, and the final measured plant density was 74,100/ha.

| Variety[1] | Treatment | Plant height (cm) 7.21-25 | Stalk diameter (mm) 7.21-7.25 | SPAD reading (leaf greenness) (7.20-25) | Silage Yield (t/ha) (adjusted to 70% moisture) |
|---|---|---|---|---|---|
| 5245 RDP-dual purpose Semi-Flex Seedlings submerged for three weeks after emergence | Omega | 112.1b | 24.6b | 49.6ab | 50.3ab |
| | SabrEx LQ (K2 + K4) | 106.1c | 28.1a | 50.9a | 59.4a |
| | K2K4As2 Omega | 117.2b | 22.3a | 47.9bc | 56.5ab |
| | K5As2 Omega | 125.8a | 28.6a | 51.0a | 46.7b |
| | Control | 99.3d | 21.4c | 46.7c | 32.0c |
| 5469 RSX--grain Determinate | Omega | 200.3 | 31.9a | 33.3a | 73.9a |
| | SabrEx LQ (K2 + K4) | 191.4c | 29.5b | 30.4ab | 71.4a |
| | K2K4As2 Omega | 203.0ab | 27.8b | 27.5b | 59.8a |
| | K5As2 Omega | 210.1a | 28.4b | 31.0ab | 57.8a |
| | Control | 174.5d | 22.2c | 17.5c | 68.6a |
| 5455 RDP--grain Semi-flex | Omega | 194.3b | 25.7b | 51.4a | 65.3a |
| | SabrEx LQ (K2 + K4) | 196.0b | 28.3a | 51.3a | 65.7a |
| | K2K4As2 Omega | 203.5ab | 29.5a | 47.9b | 61.8a |
| | K5As2 Omega | 211.3a | 28.5a | 51.1a | 65.2a |
| | Control | 174.5c | 22.5c | 45.5c | 56.9a |
| 5018G3-dual purpose Determinate | Omega | 193.4ab | 25.7b | 49.8a | 72.5ab |
| | SabrEx LQ (K2 + K4) | 190.5b | 28.1ab | 53.2a | 73.3a |
| | K2K4As2 Omega | 205.6ab | 28.6a | 49.0a | 56.2bc |
| | K5As2 Omega | 208.1a | 28.4ab | 62.1a | 68.7ab |
| | Control | 174.0c | 22.4c | 47.1a | 49.4c |
| 6490-dual purpose Full flex | Omega | 200.9ab | 28.1b | 50.8a | 80.1b |
| | SabrEx LQ (K2 + K4) | 195.4b | 28.6b | 49.7a | 100.5a |
| | K2K4As2 Omega | 208.5a | 27.7b | 50.7a | 58.6c |
| | K5As2 Omega | 192.8b | 30.9a | 50.6a | 68.7bc |
| | Control | 170.5c | 22.3c | 46.3b | 53.6c |

Numbers followed by dissimilar letters are significantly different P=0.1 as determined by Agrciola LSD tests.

The letters and numbers following the varietal number indicate transgenic character; RDP indicates resistance to glyphosate, European corn borer and corn ear worm/fall armyworm; RSX indicates resistance to glyphosate, glufosinate, European corn borer, corn rootworm and corn earworm and armyworm; G3 indicates resistance to glyphosate, glufosinate, European corn borer, corn rootworm and corn earworm and armyworm. 1 The letters and numbers following the varietal number indicate transgenic character; RDP indicates resistance to glyphosate, European corn borer and corn ear worm/fall armyworm; RSX indicates resistance to glyphosate, glufosinate, European corn borer, corn rootworm and corn earworm and armyworm; G3 indicates resistance to glyphosate, glufosinate, European corn borer, corn rootworm and corn earworm and armyworm. Some varieties are bred for grain yield and some as dual purpose (grain and silage), and marketed this way by the supplier, Chemgro Seeds.

TABLE 4

Biomass, and carbon and nitrogen contents of corn harvested in GH15 across varieties for the most effective seed treatment (SABREX) vs the control.

| Treatment | Dry wt (kg/ha) | % carbon[1] | % nitrogen[2] | carbon sequestered (t/ha) | Nitrogen incorporated (kg/ha) | Total C, shoots and roots (t, est)[3] | Total N, shoots and roots (kg, est)[3] | Net increase C over control | Net increase N over control |
|---|---|---|---|---|---|---|---|---|---|
| 5245 SabrEx | 17820 | 42.5 | 1.75 | 7.6 | 311 | 15.2 | 622 | 7 | 286 |
| 5245 Control | 9600 | 42.5 | 1.75 | 4.1 | 168 | 8.2 | 336 | — | — |
| 5469 SabrEx | 21420 | 42.5 | 1.75 | 9.1 | 374 | 18.2 | 748 | 0.8 | 28 |
| 5469 Control | 20580 | 42.5 | 1.75 | 8.7 | 360 | 17.4 | 720 | — | — |
| 5455 SabrEx | 19710 | 42.5 | 1.75 | 8.4 | 345 | 16.8 | 690 | 4.2 | 6 |
| 5455 Control | 17070 | 42.5 | 1.75 | 7.3 | 342 | 14.6 | 684 | — | — |
| 5018 SabrEx | 21990 | 42.5 | 1.75 | 9.3 | 384 | 18.6 | 768 | 6 | 178 |
| 5018 Control | 14820 | 42.5 | 1.75 | 6.3 | 295 | 12.6 | 590 | — | — |

TABLE 4-continued

Biomass, and carbon and nitrogen contents of corn harvested in GH15 across varieties for the most effective seed treatment (SABREX) vs the control.

| Treatment | Dry wt (kg/ha) | % carbon[1] | % nitrogen[2] | carbon sequestered (t/ha) | Nitrogen incorporated (kg/ha) | Total C, shoots and roots (t, est)[3] | Total N, shoots and roots (kg, est)[3] | Net increase C over control | Net increase N over control |
|---|---|---|---|---|---|---|---|---|---|
| 6490 SabrEx | 30150 | 42.5 | 1.75 | 12.8 | 528 | 25.6 | 1056 | 12.8 | 494 |
| 6490 Control | 16080 | 42.5 | 1.75 | 6.4 | 281 | 12.8 | 562 | — | — |

Example 11: *Trichoderma* strain K5 increases growth in maize in the greenhouse and in the field when applied as a seed treatment. Field and greenhouse trials in upstate NY showed that corn seeds treated with *T. virens* NRRL 50520 resulted in plants with improved growth, development and yield. FIG. 1 of this section shows corn plants grown from seeds treated with K5 treatment as compared to the existing SABREX product as well as an untreated control. The treatments also included an adjuvant that is labeled as MJ. This adjuvant, which is proprietary, is a seed treatment further enhances the effects of strain K5. FIG. 5C shows primary and secondary ears from corn plants in the same experimental trial as shown in FIG. 5A. Primary ears from plants grown from K5 treated seeds treatment showed two additional (16 vs 18) kernel rows when compared to the untreated control. Kernel row number is an important yield component in advanced corn variety selection with more rows translating to improved yield. Extra kernel rows were also seen in the secondary ear and secondary ears were more developed. Corn row numbers and development of secondary ears are primary determinants of maize yield. In all cases, growth and development of plants and ears was visually superior to those grown with seeds treated with SABREX or with no seed treatment.

Figure 6:
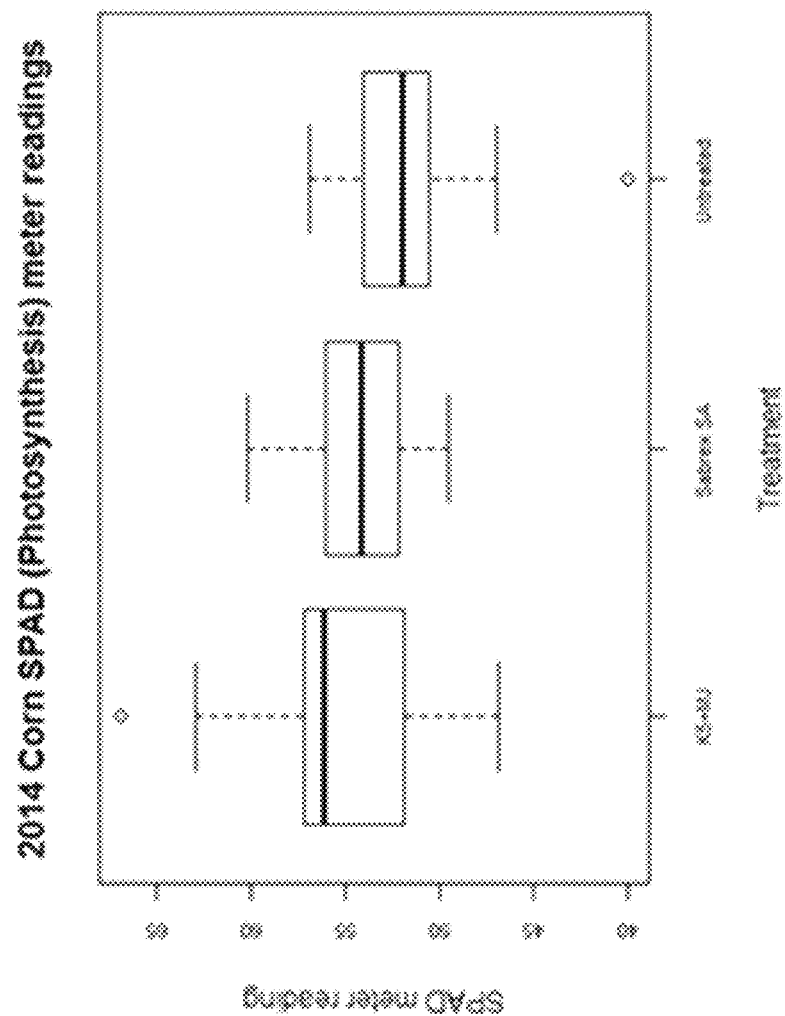
FIG. 6 depicts a graph showing box and whisker plots for SPAD meter readings on corn field trials comparing K5 with SABREX SA and the untreated control. While data distribution for K5 is broad, this treatment is significantly better than the control as shown in Table 1.
Figure 7B:
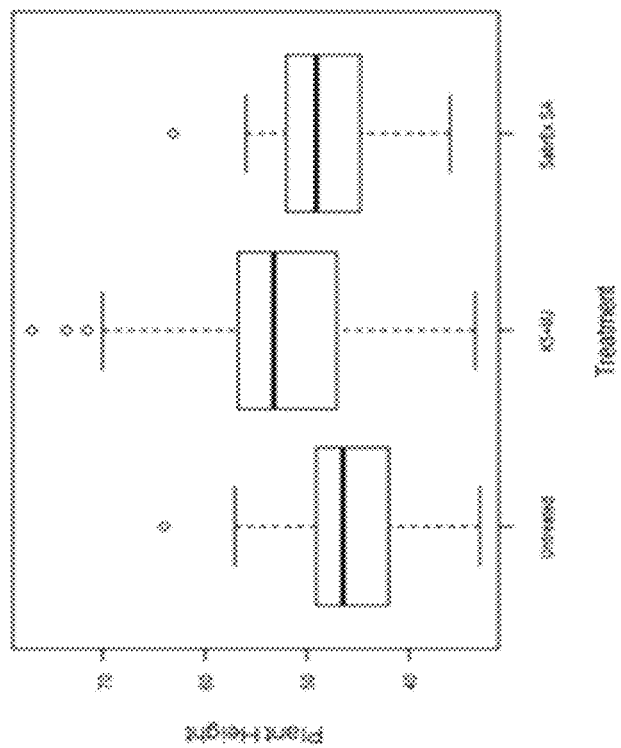
FIG. 7B depicts a graph showing box and whisker plots for plant height of untreated (left), K5-MJ (middle) and SABREX SA (right).
Figure 7A:
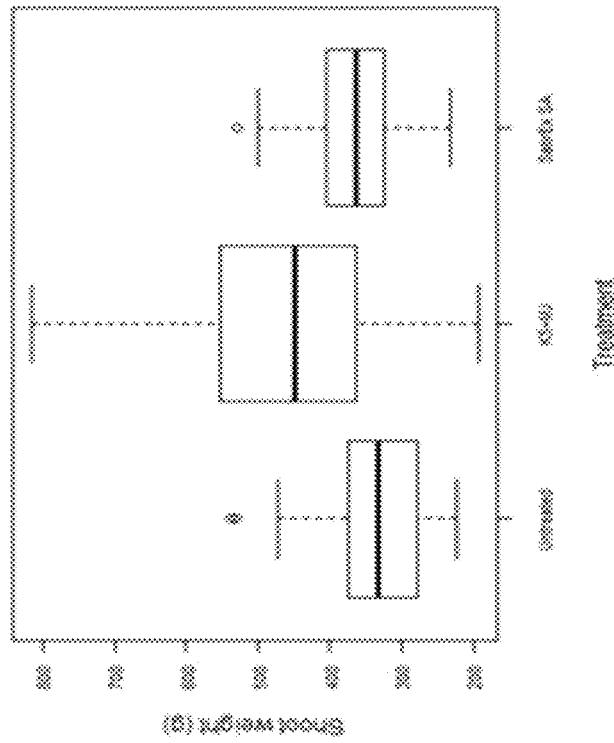
FIG. 7A depicts a graph showing box and whisker plots for shoot weight of untreated (left), K5-MJ (middle) and SABREX SA (right).

The statistical analysis of this field data follows. Plant height, shoot weight (FIG. 7A-7B), and Spad meter (photosynthesis; see FIG. 6) were both shown to be significantly improved in the K5 treatment. Both of these characters are critical for silage yield and translate to grain yield especially when the kernel row numbers on primary and secondary ears are also taken into account. Means separations tests (LSD, alpha=0.05) demonstrated that shoot weight and plant height in the K5 treatment were both significantly improved over both the untreated control as well as SABREX, the existing high-performance corn biological seed treatment.

Figure 8:
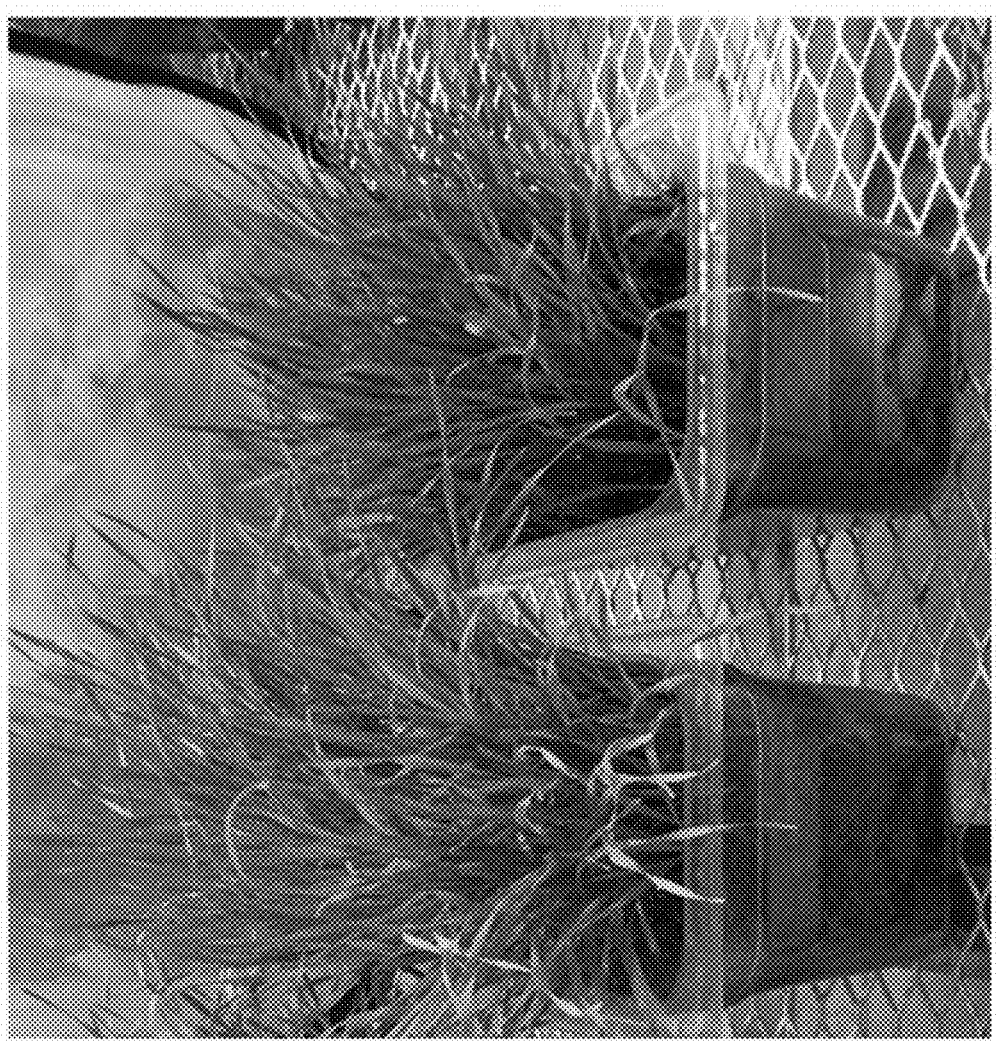
FIG. 8 depicts wheat seedlings from greenhouse trials of foliar sprays. K5 at left and untreated (water only) on the right shows significant growth increase with foliar application of strain K5.
Figure 9:
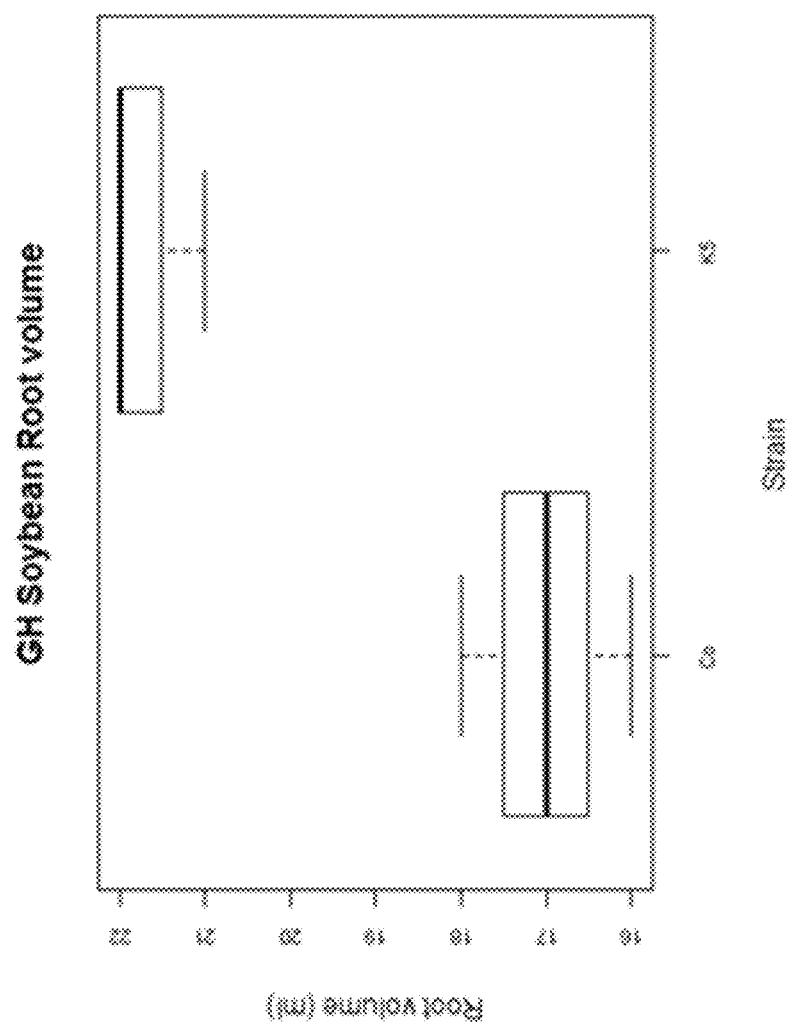
FIG. 9 depicts a graph showing root volume of greenhouse soybeans with a control (left) and K5 (right).
Figure 10:
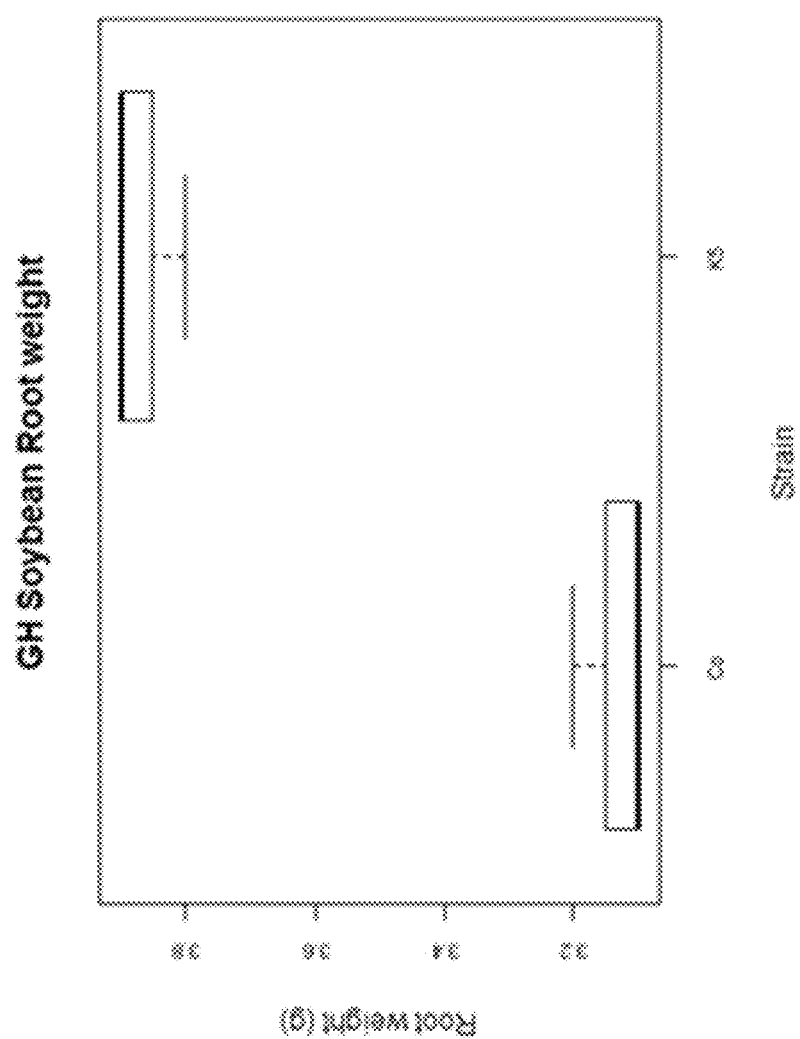
FIG. 10 depicts a graph showing root weight of greenhouse soybeans with a control (left) and K5 (right).
Figure 11:
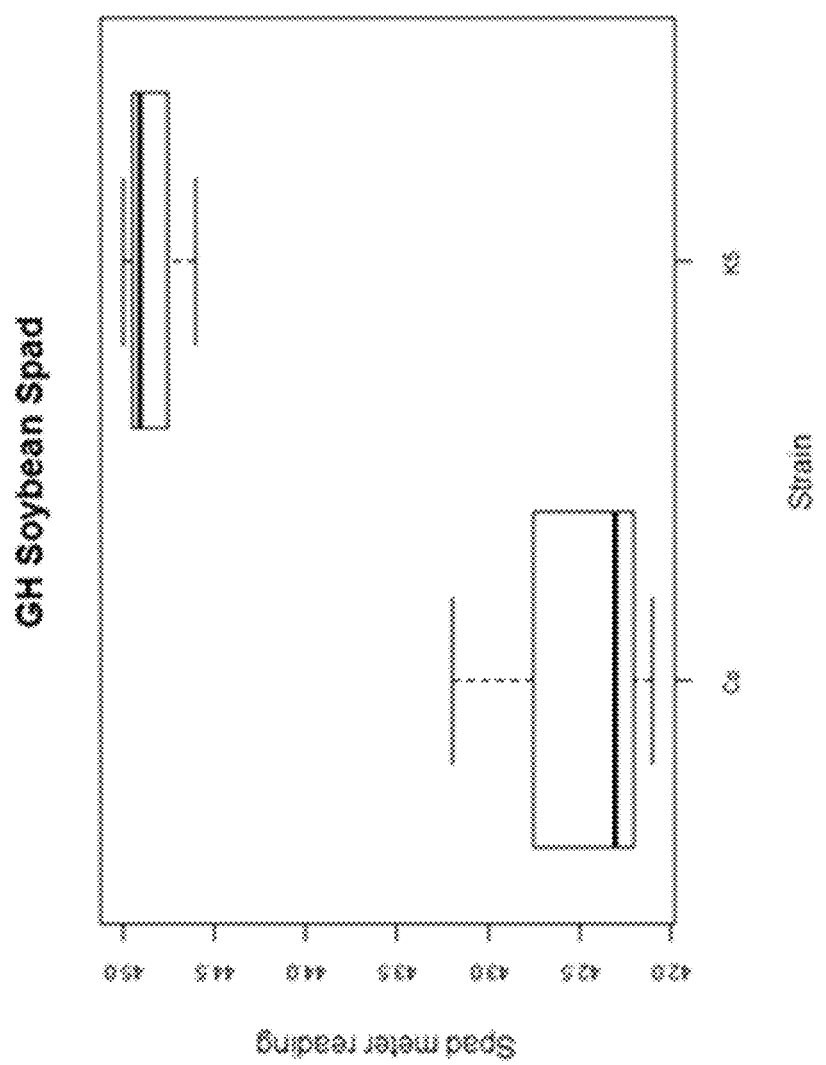
FIG. 11 depicts a graph showing SPAD measurement of greenhouse soybeans with a control (left) and K5 (right).
Figure 12:
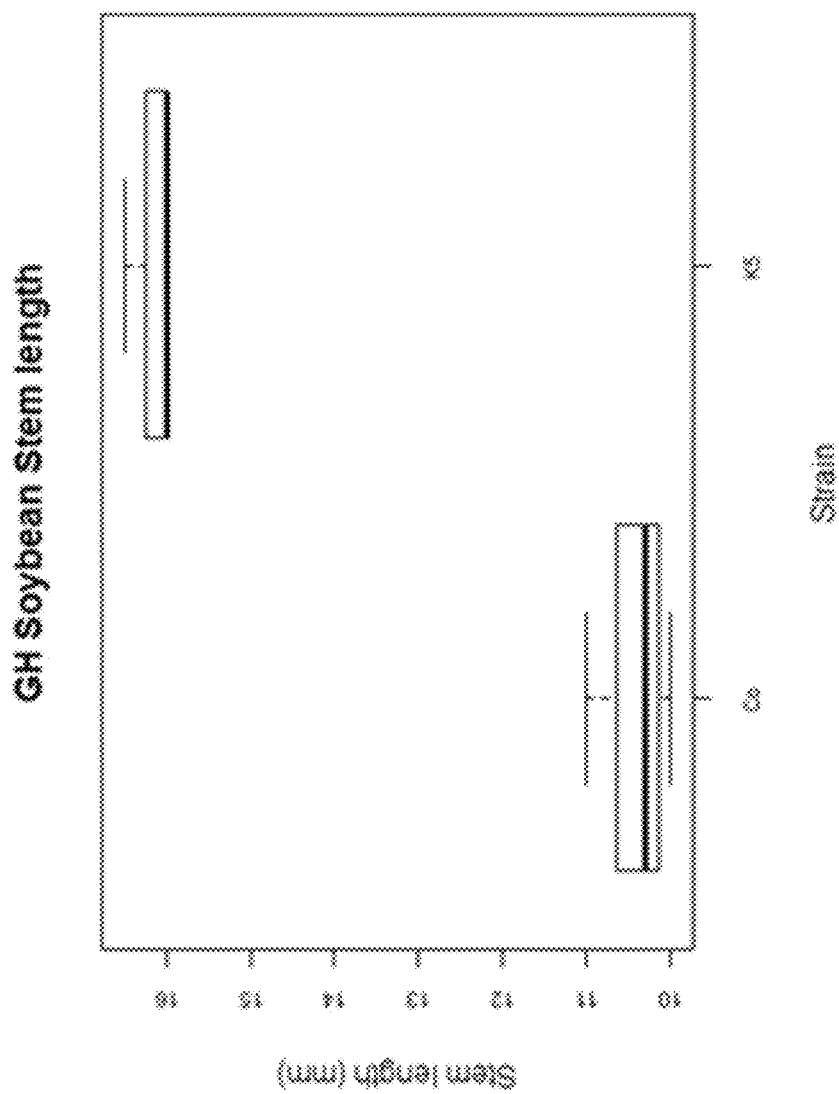
FIG. 12 depicts a graph showing stem length of greenhouse soybeans with a control (left) and K5 (right).

Example 12 of this section—*Trichoderma* strain K5 increases growth in greenhouse grown wheat when applied as a foliar. FIG. 4 of this section shows the results of these treatments with the K5 sample (at left) being clearly larger and more vigorous that the control (at Wheat seedlings were planted into well drained containers in the greenhouse and treated with a foliar spray following emergence). Control plants were sprayed with water only. FIG. 8 shows the results of these treatments with the K5 sample (at left) being clearly larger and more vigorous that the control (at right).

Figure 5:
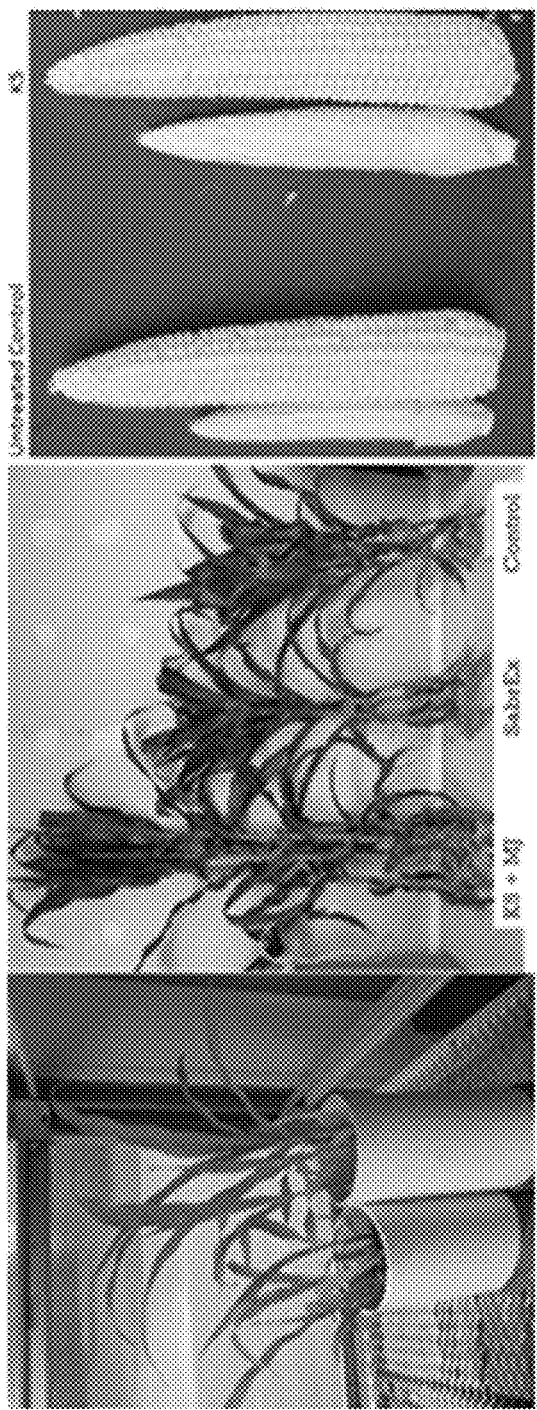
FIG. 5A shows plants grown from plants treated with nothing (left) and K5 (right).
FIG. 5B shows plants grown from field trials from seeds treaded with KS+MJ (left), SABREX (middle), and nothing (right).
FIG. 5C shows developing ears from seeds treated with nothing (left) and K5 (right).

Example 13 of this section—*Trichoderma* strain K5 increases growth in soybean in the greenhouse when applied as a seed treatment. Soybean seeds were treated with either *T. virens* NRRL B-5025 strain or left untreated with no other microbial or chemical treatments being applied. These were planted into sand tubes and growth data was collected as the seeds emerged and the seedlings grew. The *Trichoderma* treatment was found to significantly increase soybean seedling growth in these experiments as demonstrated in FIG. 5 showing stem length, Spad meter readings, root weight, and root volume. All of the differences shown in FIGS. 9-12 are significant at alpha=0.05 or 0.01.

FIGS. 9-12 show Box and whisker plots showing mean differences and data distribution for characters root volume (p=0.0198), root weight (p=0.0082), spad (p=0.0375), and stem length (p=0.0057) for soybeans in the greenhouse having been seed treated with *Trichoderma* strain K5.

Therefore, FMD—as it relates to the present invention in certain embodiments—has the following components: (1) microbial strains each individually are rhizospheric and endophytically competent. In addition (2) we expect that metabolites are the specific triggers of changes in plant gene expression, so the concept of FMD also includes the triggering compounds. In our definition, FMD requires metabolites that give benefits for a period of months (for metabolites) or at least a season (microbes) and strains or metabolites that are effective when added as seed treatments at levels of about 70 mg/ha (microbes) or at less than 1 µl/seed (metabolites). Effective strains, metabolites or mixtures of the two are then combined into single treatments that are expected to provide better results than any of the components used singly. Since each component is strongly able to colonize plant roots and become an integral and long-lasting component of the plant (microbes) or to have long-term effects (both microbes and metabolites) we anticipate substantial and beneficial changes in the plant phytobiome that lead to long-term benefits to plant performance.

These agents also can enhance or maintain photosynthetic efficiency in plants. All of these improvements in plant performance noted above are energy intensive, and for specific microbes to induce these changes, the plants also must have improved photosynthetic efficiency. In support of the concept of an improvement in the basal level of photosynthesis are the following: there are many reports of enhanced leaf greenness as a consequence of inoculation with microbial agents. This is evidenced by results of gene expression and/or proteomic studies that demonstrate that photosynthetic elements are among those overexpressed. These include rubisco and photosystem II oxygen evolving complex protein. When photosynthesis is enhanced, then available resource such as starch is also increased. Substantiating the expectations that these changes directly affect plant photosynthesis was the demonstration that a strain of *T. virens* resulted in an increase of carbon sequestration in corn more than 60%. Moreover, photosynthesis and photosynthetic machinery are highly susceptible to damage by reactive oxygen species (ROS). Stresses such as drought, salt, and flooding result in accumulation of levels of ROS that are highly damaging to them. Even other otherwise optimal growing conditions, light in excess of its utilization in photosynthesis result in production of ROS, including the superoxide anion, that are detrimental to pigments, proteins and lipids.

Therefore, damage to photosynthetic systems occurs as a consequence of ROS accumulation that may be induced by stresses or even by otherwise optimal conditions at high light levels. This is of serious consequence, since photosynthesis is therefore the ultimate limiting factor in the growth of plants. Unfortunately, the best measured photosynthesis is only about 20% of the theoretical maximum conversion rates (which are 0.1 and 0.13 for C3 and C4 plants) and this has not noticeably improved through plant improvement efforts. Thus, yields have increased without improving the photosynthetic rate, which is the fundamental limiting factor. The rate of increase in yield improvements of major crops has decreased in recent years, in part because the other inputs and improvements are becoming limited by the lack of improvement in photosynthetic efficiency. Yield potential (YP) of crop plants, likewise, can be approximated as the product of the solar radiation received over the unit of land in a single growing season (Q), the efficiencies of the plant to intercept the radiation (E1), conversion of radiation energy into biomass energy (E2), and partitioning of the biomass into the harvestable parts of the plants (E3) (YP=Q·E1·E2·E3).

All of these strategies and alternatives positively affect the environment. For example, FPE or FTE have the potential to increase carbon sequestration, and the organisms also enhance nitrogen use efficiency (NUE) and thereby reduce the important greenhouse gases CO2 and NO. In addition, greater NUE is likely to reduce water pollution from NO3 and NO2 from runoff from fertilized fields (Harman, 2011). If this potential is being realized, then greater total incorporation of C and N should be present in harvested biomass. Clearly, if greater levels of C or N are sequestered or incorporated into crop plants, then they are not present in either the atmosphere or waterways. The impact of annual crops on these environmental factors has not been seriously considered with annual crops because sequestered C or N are rapidly cycled back into the environment as the plant products are harvested and used. However, this does not take into consideration the biomass in roots, which is large and increased by the changed phytobiome that results from use of these organisms. The C and N contained within root biomass is slowly degraded and the organic materials and incorporated into organic materials in the soil. Thus, the soil become a reservoir for both of these elements and, with larger root systems, soil organic material, and therefore soil tilth and productivity, are enhanced.

Corn variety experiments, moreover, imparted their abilities to utilize photosynthate for either total biomass or grain weight, where determinate ear varieties having little or no ability to increase ear or plant size beyond a genetically limited amount will not increase grain yields as much as varieties that have indeterminate ear and plant habits. Enhanced FPE or TPE in this way increases CO2 sequestration in field grown plants and since the endophytic fungi increase root development, much of this sequestered carbon will be placed underground, where it will not be rapidly re-released into the air. Further, the increased abilities of plants to utilize nitrogen efficiently will result in more nitrogen incorporated into the plant and less that is available to pollute water or air. Therefore, the total C and N incorporated into field grown corn was measured. Yield and photosynthesis interact strongly with nitrogen available to the plants. This study also examined the interaction of different corn varieties with nitrogen uptake.

The endophytically and rhizospherically competent *Trichoderma* strains in the present invention utilize *T. afroharzianum* (formerly *T. harzianum*) strain RR17Bc (ATCC accession PTA 9708; K2), *T. harzianum* (formerly *T. harzianum*) F11Bab (ATCC accession PTA 9709; K3), *T. atroviride* strain WW10TC4 (ATCC accession PTA 9707; K4), and *T. atroviride* (formerly *viride*) strain NRRL B50520 (K5) all of which have been described previously. Also used is a *Bacillus amyloliquefaciens* strain (As2) isolated from alfalfa stems in Ontario County N.Y.

Example 14: Growth of the microbial agents onto radicles emerging from treated seeds, and their localization on and in plants and on the next generation of seeds.

Microscopy. Corn seeds of a commercial hybrid (Viking Seed Co. MX00029) without a fungicide treatment were treated with fungal conidial spore suspensions at 1×109 cfu (colony forming units)/ml and used to treat seeds at the rate of 0.9 ml/kg for each organism and germinated on moistened sterilized blotters for 48-72 hr. Radicles emerged from the seeds in less than 48 hr, and the surfaces of the emerged radicles were imaged with fluorescent microscopy. Confocal microscopic observations were conducted following application of Calcofluor-Evans blue strain used according to the manufacturer's directions (18909 Calcofluor White Stain, Sigma Aldrich, St. Louis Mo.). Microscopy was performed at the Cornell University Plant Cell Imaging Center on a Leica TCS SP5 Laser Scanning Confocal Microscope.

Shoot and root colonization from treated seeds in the greenhouse. Seeds of corn or soybeans were treated with different microbial agents or untreated and planted in the greenhouse in a standard potting mix (Sungro Professional Potting Mix). Seeds of corn were treated by the supplier with a fungicide mixture (Cruiser Maxx 250, Syngenta Crop Protection, which contains thiamethoxam, fludioxonil, mefenoxam, azoxystrobin, and thiabendazole) and the biological treatments were applied over the chemical treatments. The soybean seeds used had no chemical treatment. After 20-35 days of growth, plants were removed from the potting mix and roots were carefully washed. After harvesting, the root and shoot segments were separated and surface sterilized. Two roots were chosen from each plant and they were sampled in three places; relative to the seed they were proximal, medial and distal. All shoot or root segments were plated on acidified PDA (Remel) containing a colony restrictor, the surfactant Igepal c630 (Alfa Aesar) (PDA Ig) and screened for the presence of *Trichoderma*. Details of tested treatments and conditions are given in Table 5 (below).

Colonization of grain produced in the field from treated seeds. Seeds of corn or soybeans from plants that had been grown from *Trichoderma* treated seeds were harvested from the field trial (next section) in 2015 and tested for the presence of *Trichoderma* or bacteria. Soybeans from 2015 were harvested from plants grown from seeds treated with the commercial product GraphExSA™ that contains *T. virens* strain K1. Several thousand seeds of corn and soybean were plated on potato dextrose agar. In addition, both corn and soybeans seeds were surface sterilized as described above, crushed and then plated onto potato dextrose agar. This latter step was included specifically to detect internally borne fungi.

Field experiments. A field experiment was established on corn (*Zea mays*) near Phelps, N.Y. (Baar Scientific, LLC) in 2014. Seeds of a transgenic, glyphosate-resistant commercial hybrid, A91-92R were obtained from Albert Lea Seeds, Albert Lea, Minn. The seeds were commercially treated with ACCELERON, a pesticide mixture containing ipconazole, metalaxyl, trifloxystrobin (fungicides) and clothianidin (insecticide). Seeds were overtreated with a liquid formulation mixture of K2 and K4, which is the commercial product SABREX LQ, according to the manufacturer's directions.

Other seeds were treated with an adjuvant consisting of a blend of a humic acid product and minor nutrients, hereafter designated MJ, together with K2, K5+As2, or K2+As2. The fungal strains used were a liquid suspension of conidia at 8×10$^8$ cfu/ml, and the As2 concentration was 8×10$^9$ cfu/ml. The microbial suspensions were used to treat seeds at the rate of 0.9 ml/kg seed for each organism. This is the *Trichoderma* seed treatment rate recommended for a commercial product (SABREX LQ™ www.abm1st.com). Preliminary experiments have demonstrated that all of the organisms used in the overtreatment are stable in the presence of the chemical pesticides (data not shown).

Plots were established on a sandy loam soil with moderate yield potential. These trials were conducted in a replicated block design with four replicates. Each treatment+replicate consisted of four rows 76 cm apart and 6 m long planted in a north-south orientation. Seeds were planted June 17 following a cool wet spring, silage harvest was September 15 and grain harvest on or about November 20. The first killing frost was in the last week of October. Weeds were controlled with glyphosate herbicide following the manufacturer's recommendations. Fertilization at the time of planting was with 46 kg of actual N/Ha in a 19:19:19 formulation. This was followed with a dressing of 96 kg in mid-July as a surface broadcast application and a third similar application in mid-August. All harvest for yield was from the middle two rows of each treatment replicate. For grain yield, the middle 4.6 m of the rows were harvested and for silage the northern 2.3 m was harvested. For root measurements and other destructive sampling, plants were dug or otherwise harvested from the outer rows away from areas that would be harvested for yield.

Plant height was measured twice during the season: just prior to tasseling and at harvest. Weights of silage and grain (yield) were collected after harvest, and the % nitrogen and carbon were assayed by a commercial service (A&L Laboratories or the Cornell Nutrient Analysis Laboratory).

Field experiments, 2015. Field trials were conducted again in 2015. The data in 2014 suggested that grain yields were limited by the performance limits of the variety used. That is, increases in photosynthate apparently were converted to vegetative biomass more efficiently than to grain yield (Table 8). Therefore, in 2015 we tested five varieties of corn described by the supplier as determinate (2 varieties), semi-flex (2 varieties), and full flex (1 variety) ear types or as grain or dual purpose (silage and grain production). These were provided by the Chemgro Company and are designated as 5469 RSX (determinant, grain), 5018 G3 (determinant, dual purpose); 5245 RDP (semi-flex dual purpose), 5455 RDP (semi-flex grain) and 6490 (full flex dual purpose). All seeds used in the experiments were treated with an insecticide/fungicide mixture (Cruiser Maxx 250, Syngenta Crop Protection) that contains thiamethoxam, fludioxonil, mefenoxam, azoxystrobin, and thiabendazole.

Prior to planting, subsamples of each variety were treated with SABREX LQ according to the manufacturer's directions. Other subsamples were treated with, K5+As2, or K2+As2 in combination with an embodiment of the present invention designated OMEGA™, containing 20 g of humic acid (Leondarite shale), 5 g yeast extract, and 100 µl of 1-octen-3-ol (Sigma Chemical Co.) in 1 L of water, and adjusted to pH 6.2. OMEGA™ was also used alone as a separate treatment with no microbial agents. This mixture was applied at the rate of 0.65 ml/kg of seeds and was developed to provide a chemically defined replacement for the humate material used in 2014. A low concentration of 1-octen-3-ol (mushroom alcohol), which is a volatile metabolite of *Trichoderma* strains, was included because it induces resistance to plant diseases as has also been reported by others and we have observed that it is a potent inducer of enhanced plant growth at very low concentrations.

This trial was located on a loamy clay soil near Waterloo, N.Y. Plots were arranged by variety across the field as two rows 22.5 m long. Each treatment×variety was harvested for silage and grain. For this harvest, each set of rows was divided into four blocks each 1.8 m long for silage harvest interspersed with four blocks each 3.6 m long for grain harvest. The plots received about 56,000 L/ha of fresh manure incorporated before planting which resulted in an application of about 155 Kg N/acre and another 150 Kg of N was applied as a liquid suspension side dress containing 32% N at about V4.

The plots received intensive rain of more than 20 cm over a three week period just after emergence (the last week of May through the first two weeks of June). The plots were laid out such that for this entire 3 week period a portion of the field was either saturated or, through much of the time, completely submerged. This area of the field coincided almost exactly with that planted with 5245 RDP, and was relatively uniformly flooded. Thus, the trials with this variety afforded a good opportunity to examine the ability of the seed treatments to assist the corn in recovery from flooding stress. The remainder of the varieties were on higher ground and so were not subjected to this stress.

Grain and silage was hand harvested. Each block was divided into four segments and 10 ears of grain and 10 plants for silage was harvested for each treatment.

Field Experiments 2016. The trials in 2014 were limited to one variety and those in 2015 were small. Therefore a larger comprehensive trial was conducted to verify the earlier data. This trial was conducted in Whitewater, Wis. with Agri-Tech Consulting, in cooperation with applicants. Chemgro hybrids 5245 (semi-flex dual purpose), 5445 (semi-flex grain) and 5469 (determinate grain) were used for second season. These seeds of these were treated with Cruiser Maxx as described above and then overtreated with nothing (control), K2+K4 (SABREX), with 1-octene-3-ol (labeled OMEGA and using the same formulation described for 2015) or with K5 liquid formulations using the treatment rates shown above. No adjuvants or other microbes were used with the K2+K4 or the K5 treatments.

A base fertilizer treatment was applied to give 138 kgNha as urea and, in addition a side dress application as urea to give 78, 190, 302 and 414 kg N/ha was also applied as a side dressing. Plots were established using a randomized complete block for each N level and each N level was in a separate adjacent block. The soil was a deep Milford silty loam with 3.4% soil organic matter. The plots received adequate moisture throughout the season, and conditions were excellent for corn growth.

Similar plots were established near Lyons, N.Y. on a rocky gravelly loam. Unfortunately, in some plots, corn grew very poorly. However, in other parts of the field, corn grew normally and it was possible to observe root growth as described in the Objective below.

Enhanced Root growth. From field trials and other tests, it was apparent that the treatments used in the 2014 and 2015 field trials enhanced root growth and development. However, while greenhouse tests gave information on young plants, we had difficulty in harvesting and measuring root growth over the entire season in the field. Therefore, developed was a system allowing growth of plants over an full season in PVC pipes after which the entire root mass was removed from the soil and measured. Also conducted was observational trials on single plants in similar tubes above ground that contained a window to measure root length over time and in the field at Lyons N.Y. where the corn grew normally.

Experiments in PVC pipes. Seeds were treated as described in the previous objective. Seeds of hybrid 5245 were started in the greenhouse, and after about 2 weeks growth, they were transplanted into field soil contained in PVC pipes 20 cm in diameter×210 cm long with a PVC cap into which holes were drilled for drainage. These tubes were filled with soil to give a soil tube about 200 cm in length. The pipes were placed vertically into soil and a silty loam field soil was added to the pipes, and then watered to compact the soil. Root lengths of the more successful treatments completely filled the tubes from top to bottom.

Root observations in the field. Observational tests were conducted on roots in the field in Lyons N.Y. in side by side plots where corn grew normally. Areas chosen supported good root growth and received a total of 414 kg/ha nitrogen as a preplant application of 78 kg/ha followed by side dressing at about V4 to provide the remaining N.

Data Analysis. Yield, biomass, and other characters measured during the 2014 and 2015 growing seasons were analyzed using the statistical analyses performed using RStudio (https://www.rstudio.com/) as described in the results that follow.

Results—Growth of the microbial agents onto radicles emerging from treated seeds.

Figures 13A, 13B:
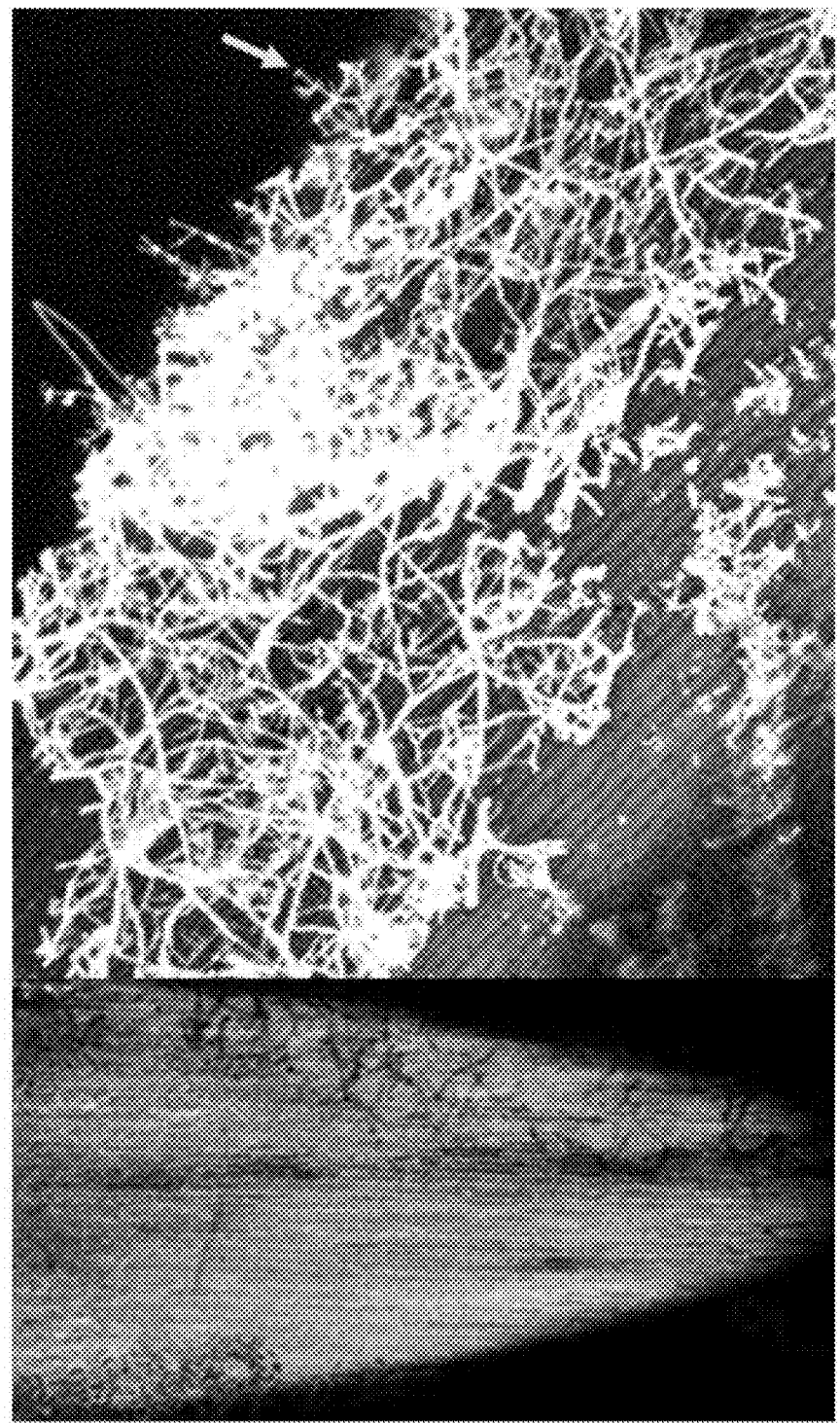
FIG. 13A depicts a photomicrograph of an emerging radicle of corn from seeds treated with conidia of strain K2, stained with Calcofluor and visualized with epifluourescent microscopy.
FIG. 13B depicts a gray tone image (used to enhance contrast) of a root 72 hr after imbibition.

The simplest and most effective method of applying endophytic microbes is via seed treatment. The *Trichoderma* strains were applied to seeds as conidia, and for the treatments described here to be effective, the conidia must germinate rapidly and colonize the radicle. This was evaluated microscopically with strain K2 (FIG. 13A-B). Confocal fluorescence microscopy revealed this strain colonized the radicle as hyphae after 48 h of seed imbition. By three days, heavy growth of the fungus was observed, together with formation of phialades for the next generation of conidia.

FIGS. 13A-B illustrate early colonization of seedlings from a seed treatment. At left is shown a photomicrograph of an emerging radicle of corn from seeds treated with conidia of strain K2, stained with Calcofluor and visualized with epifluourescent microscopy. Without staining and illumination, the organism cannot be seen. The picture was taken of radicle 48 hours after imbibition began, just after the radicle emerged from the seed coat (FIG. 13A). The blue webbing is the organism; hyphae are about 4 μm wide. FIG. 13B shows a gray tone image (used to enhance contrast) of a root 72 hr after imbibition. The growth of the organism is more pronounced and philiades are visible (arrow).

Localization on and in plants and grain produced from treated seeds. The ability of five strains presented here, representing three species, of endophytic *Trichoderma* was investigated by plating surface-sterilized shoot or root segments of either soybeans or corn. Root segments of young seedlings grown from treated seeds were frequently, but not always, colonized by the *Trichoderma* strains. Since root segments were surface-sterilized, the *Trichoderma* strains that grew were shown to have colonized the internal portions of the roots, and therefore were endophytes. A significantly lesser percentage of the root segments from untreated seeds were also colonized by some *Trichoderma* strains (see Table 5, below). Since *Trichoderma* strains are ubiquitous in most environments, we considered that the colonization of control roots may have arisen from contaminants in the environment. To evaluate this hypothesis, the fungi from some of the roots from control plants of corn hybrid 4250 were isolated on PDA, DNA was isolated, and DNA from the TEF1 (encoding translocation elongation factor 1) and ITS (encoding internal transcribed spacer) was amplified. These sequences are frequently used for taxonomy of *Trichoderma* strains (Samuels and Hebbar 2015) The results from three of the presumed contaminants indicated that two of the strains were *T. asperellum* while the third was *T. virens*. Clearly two of the three were of different species than any of our strains, thereby confirming the hypothesis that the strains colonizing the roots of control plants were from contaminating species. Even though the roots were colonized, none of the shoots were (Table 5), thus strongly indicating these endophytic *Trichoderma* strains were localized in the roots, and did not colonize the shoots.

Absence of any of the strains in seeds produced from plants grown from *Trichoderma* treated seeds.

TABLE 5

Tests comparing colonization of shoots or roots with *Trichoderma*.

| Variety | Days growth | % shoot segments colonized | % root segments colonized | Dunnett's test probability-roots* |
|---|---|---|---|---|
| Corn-Hybrid 6490 | | | | |
| SabrEx | 20 | 0 | 88 | 0.00167 |
| Control | | 0 | 14 | |
| Corn Hybrid 4250 | | | | |
| K1 | 21 | 0 | 89 | <0.001 |
| K2 | | 0 | 75 | 0.0554 |
| K3 | | 0 | 69 | 0.01993 |
| K4 | | 0 | 78 | 0.00283 |
| K5 | | 0 | 69 | 0.01988 |
| Control | | 0 | 36 | |
| Soybean-Viking MX000209 | | | | |
| K1 | 31 | 0 | 83 | 0.00166 |
| K2 | | 0 | 75 | 0.00373 |
| Control | | 0 | 12 | |

The values given in Table 5 are the probability (using Dunnett's Contrasts) that the percentage of roots colonized and harvested from treated seeds were not different from the percentage from the roots grown from control (non-treated) seeds. For each comparison, six seedlings were grown and two roots were harvested from each. Three 1 cm segments were taken from each root to represent proximal, medial and distal parts of the roots relative to the seed and then surface sterilized. The values presented are the percentage of total root segments from the six plants that were colonized as evidenced by plating on acidified potato dextrose agar with the colony restrictor Igepal Co630.

An important consideration for regulatory authorities is whether seeds of the next generation of seeds produced from plants grown from treated seeds will be colonized by *Trichoderma*. For these evaluations, corn seeds of five hybrids produced from the plots shown in FIG. 3 were harvested and plated on PDA Ig. Similarly, seeds of three varieties were harvested from soybeans grown in the field and either treated or not treated with K1+*Bradyrhizobium japonicum*. The testing was conducted on 5000 corn seeds and 1200 soybeans seeds. No *Trichoderma* strains were detected on any seeds although there was abundant colonization by contaminating bacteria (based on colony morphology probably *Bacillus* spp.) and fungi (such as *Penicillium* and *Fusarium* spp), on the medium (see Tables 6 and 7, below).

TABLE 6

Numbers of corn seeds from plants grown from Trichodema-treated seeds (200 seeds were tested) that gave rise to Trichoderma spp., and where tested, other microorganisms.

| Hybrid | Treatment | # 2$^{nd}$ generation seeds/200 tested giving rise to Trichoderma infection on PDA Ig | % seeds with other fungal contamination | % seeds with bacterial contamination |
|---|---|---|---|---|
| 6490 | K2 + K4 | 0 | Not done | Not done |
| 6490 | Metabolite only | 0 | Not done | Not done |
| 6490 | K2 + K4 + As2 | 0 | Not done | Not done |
| 6490 | K5 + As2 | 0 | Not done | Not done |
| 6490 | Control | 0 | Not done | Not done |
| 5018 | K2 + K4 | 0 | Not done | Not done |
| 5018 | Metabolite only | 0 | Not done | Not done |
| 5018 | K2 + K4 + As2 | 0 | Not done | Not done |
| 5018 | K5 + As2 | 0 | Not done | Not done |
| 5018 | Control | 0 | Not done | Not done |
| 5469 | K2 + K4 | 0 | Not done | Not done |
| 5469 | Metabolite only | 0 | Not done | Not done |
| 5469 | K2 + K4 + As2 | 0 | Not done | Not done |
| 5469 | K5 + As2 | 0 | 92 | 85 |
| 5469 | Control | 0 | Not done | Not done |
| 5245 | K2 + K4 | 0 | Not done | Not done |
| 5245 | Metabolite only | 0 | Not done | Not done |
| 5245 | K2 + K4 + As2 | 0 | Not done | Not done |
| 5245 | K5 + As2 | 0 | 79 | 98 |
| 5245 | Control | 0 | Not done | Not done |
| 5445 | K2 + K4 | 0 | 76 | 95 |
| 5445 | Metabolite only | 0 | 84 | 95 |
| 5445 | K2 + K4 + As2 | 0 | 80 | 90 |
| 5445 | K5 + As2 | 0 | 82 | 83 |
| 5445 | Control | 0 | 72 | 96 |

TABLE 7

Numbers of soybean seeds from plants grown from Trichoderma-treated seeds (200 seeds were tested) that gave rise to Trichoderma spp., and where tested, other microorganisms.

| Variety | Treatment | # 2$^{nd}$ generation seeds/200 tested giving rise to Trichoderma infection on PDA Ig | % seeds with other fungal contamination | % seeds with bacterial contamination |
|---|---|---|---|---|
| 1445 | K1 + Bradyrhizobium | 0 | Not done | Not done |
| 1445 | Control | 0 | Not done | Not done |
| 1749 | K1 + Bradyrhizobium | 0 | Not done | Not done |
| 1749 | Control | 0 | Not done | Not done |
| 1948 | K1 + Bradyrhizobium | 0 | 38 | 97 |
| 1948 | Control | 0 | 88 | 67 |

However, it could be argued these other microbes prevented growth of the Trichoderma strains. It is also possible that the seeds themselves prevented growth of internal contamination of Trichoderma spp. due to physical limitations. These issues were addressed by surface sterilization of additional seeds followed by crushing of them with pliers prior to plating the seeds on PDA Ig. Fifty seeds of corn hybrid 5469 and soybean variety 1445 were subjected to these treatments. Of the 50 seeds of each type, none of the surface-sterilized, crushed seeds gave rise to any Trichoderma strains. However, other organisms did colonize these seeds; the internal colonists included, based on colony morphology, Epicoccum, fungi with sterile hyphae, and Fusarium spp.

The results from the shoot-root plating and the seed colonization studies strongly indicate that the Trichoderma strains used in these studies colonize the roots but not shoots or seeds.

Field trials, 2014 and 2015. In 2014, yields (both grain and silage) and growth and development parameters were measured on a single variety. Plant heights, stalk diameter and shoot weights were all significantly increased by the seed treatments (i.e., K5+As2 with the adjuvant, K5 with the adjuvant, and SABREX) over the control when measured in the field just before tasseling (Table 8). However, treatment plant heights were not significantly different when measured after plants were mature (data not shown). Yields of both grain and silage were significantly increased by treatment with K5+As2, with K5. and to a lesser extent by SABREX, (1$^{st}$ set of columns in FIG. 3 and Table 3), but the increase from 9 to 12 t/ha with the SABREX treatment was nonsignificant with the SABREX treatment. K5 without As2 gave very similar results to those of K5+As2 (grain yields of both were 11.7 t/ha and silage yields were 68.6 and 62.5 t/ha, respectively, for K5+As2 and K5 alone) (See FIGS. 14A-D). At the end of the season, leaf diseases were evident. Treatment with the biological agents resulted in a significant reduction in northern leaf blight but an increase in corn leaf rust (Table 8).

TABLE 8

Plant growth and development measurements in 2014.

| Treatment | Plant Height (cm) | Stalk Diameter (mm) | Shoot wt/plant (g) | Root wt (g) | % Corn Leaf Rust | % Northern Leaf Blight |
|---|---|---|---|---|---|---|
| Control | 116 | 14.7 | 342 | 56.5 | 3.8 | 8 |
| K5 As2 MJ | 146 | 17.2 | 522 | 133 | 4.3 | 4.6 |
| K5 MJ | 135 | 16.8 | 452 | 95 | 5.4 | 5.4 |
| SabrEx | 123 | 16.4 | 363 | 69 | 4.3 | 4.3 |

Referring to Table 8, all statistical analyses were conducted with ARM version 8 (Gylling Data Management, Brooking S. Dak. 57006). Plant height data were collected on Aug. 5, 2014 and each value represents the mean of 10 plant heights from the center of the plot at about growth stage Vt. The CV was 11.44%, the Barlett's X2 value was 3.234. The probability that means of replicate values were similar was 0.78 and that treatment means were similar was 0.031.

Stalk diameter and shoot weight data were collected on Aug. 5, 2014 and each value represents the mean of stalk diameters of 10 plants from the center of the plot at about growth stage Vt. The CV was 9.16%, the Barlett's X2 value was 14.90, and the probability that replicate means were similar was 0.27 and that treatment means were similar was 0.012.

Root weight data were collected on Aug. 4, 2014 and each value represents the mean of root weights dug from 10 plants/plot from outside the harvested area. The CV was 18.8%, the Barlett's X2 value was 3.44, and the probability that replicate means were similar was 0.03 and that treatment means were similar was 0.0026.

Corn leaf rust data were collected at the end of the season and represent the mean leaf area covered by disease from 20 plants. The CV was 14.79%, the Barlett's X2 value was 10.44, and the probability that replicate means were similar was 0.107 and that treatment means were similar was 0.0087.

Northern leaf blight data were collected at the end of the season and represent the mean % leaf area covered by disease from 20 plants. The CV was 18.67%, the Barlett's X2 value was 6.497. The probability that means of replicate values were similar was 0.002 and that treatment means were similar was 0.0064.

In 2015, trials were conducted across five varieties with different ear types. The seed treatments evaluated further included the use of OMEGA which contained the metabolite and an adjuvant mixture consisting of yeast extract and a humic acid material and no microbial agents. Somewhat different growth and development parameters were measured in 2015 than in 2014, but plant height just before tasseling and stalk diameters were increased with all treatments and across all hybrids (Table 9). However, again as 2015, height differences were less at harvest than prior to tasseling. Leaf greenness as measured using handheld SPAD was measured and increased as a consequence of seed treatment.

TABLE 9

Plant growth and development measurements in 2015.

| Hybrid | Ear Type and Purpose | Treatment | Plant height (cm) | Stalk diameter (mm) | SPAD reading (leaf greenness) | Notes |
|---|---|---|---|---|---|---|
| 5245 | Semi-Flex, dual purpose | Control | 99 | 21 | 47 | Flooded for 3 weeks |
|  |  | K5As2 Omega | 126 | 29 | 48 |  |
|  |  | Omega | 112 | 21 | 50 |  |
|  |  | SabrEx | 106 | 28 | 59 |  |
| 5469 | Determinant, grain | Control | 175 | 22 | 18 |  |
|  |  | K5As2 Omega | 210 | 28 | 28 |  |
|  |  | Omega | 200 | 32 | 33 |  |
|  |  | SabrEx | 191 | 26 | 30 |  |
| 5455 | Semi-Flex, grain | Control | 175 | 23 | 46 |  |
|  |  | K5As2 Omega | 125 | 29 | 51 |  |
|  |  | Omega | 194 | 26 | 51 |  |
|  |  | SabrEx | 196 | 28 | 51 |  |
| 5018 | Determinant, dual purpose | Control | 174 | 22 | 47 |  |
|  |  | K5As2 Omega | 208 | 28 | 62 |  |
|  |  | Omega | 193 | 26 | 50 |  |
|  |  | SabrEx | 191 | 38 | 53 |  |
| 6490 | Full Flex, Dual Purpose | Control | 171 | 22 | 46 |  |
|  |  | K5As2 Omega | 193 | 31 | 51 |  |
|  |  | Omega | 201 | 38 | 51 |  |
|  |  | SabEx | 195 | 29 | 50 |  |

Referring to Table 9, each variety was in a separate block and so means can only be statistically compared within varieties. There was an elevation difference of about 5-10 m in the field, and the varieties are arranged from the lowest-lying to the highest lying plot. Just after seedlings emerged, the area received about 25 cm of rain in three weeks and for that period of time, the seedling in the lowest lying (5245) plot were submerged, as was the adjacent end of the next plot. Thus, this part of the experiment is a test of the abilities of the treatments to assist plants in recovery from this stress. Foliar diseases were not seen in these plots. Plant heights, stalk diameters and SPAD readings were taken at about V12, just before tasseling. The seeding density was provided to give 80,279 plants/ha for all varieties, and the final measured plant density was 74,100/ha.

Figure 14A:
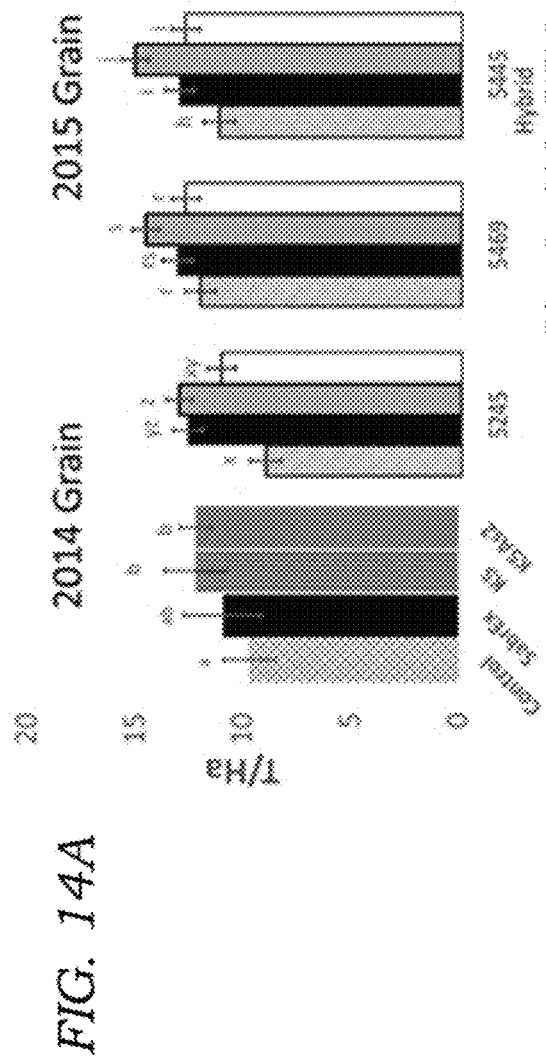
FIGS. 14A-14D depict grain and silage yields of field trials on corn in 2014 (Hybrid A91-92R) and 2015 (the other five hybrids) and estimates of the total C and N in biomass at harvest.
Figure 14B:
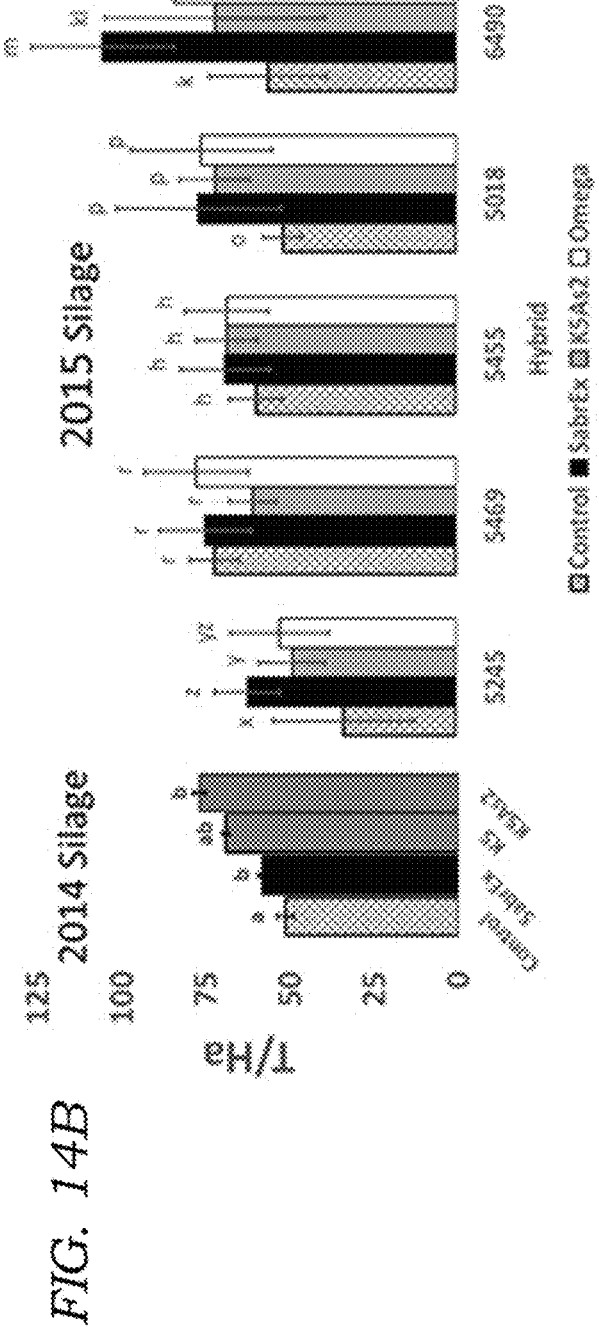
Figure 14C:
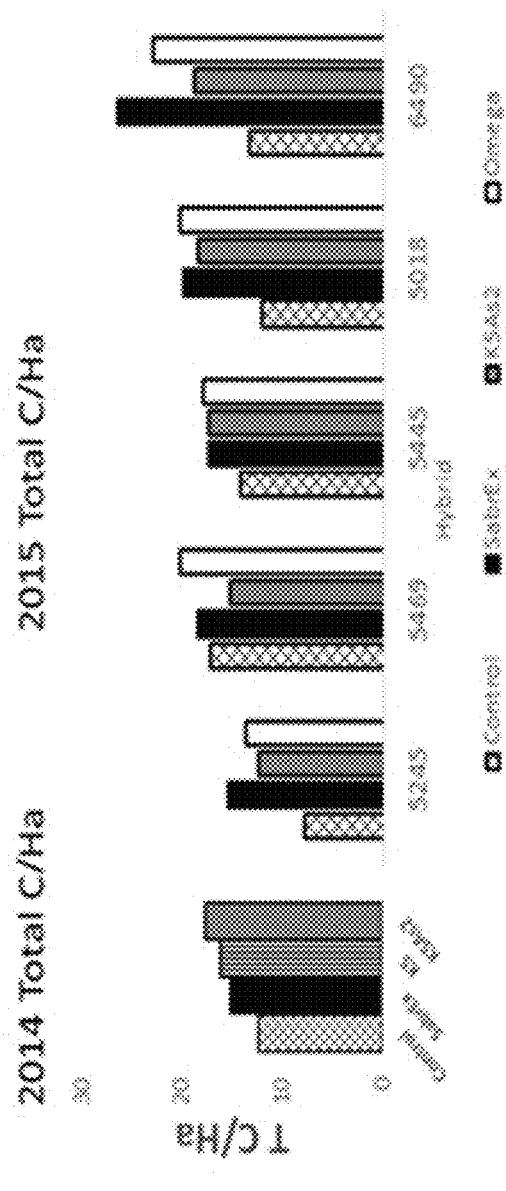

As in 2014, the treatments increased yields of grain, but the difference was nonsignificant with hybrid 5469 (FIG. 14C). Silage yields also were generally increased, but several combinations of hybrids×treatments were nonsignificant. Most notably, the two hybrids designated for use with grain and not silage (5469 and 5455) gave small and nonsignificant changes, while others that are dual purpose hybrids for use for both grain and silage production, gave better results (FIGS. 14A-D).

Referring to FIGS. 14A-D, prior to planting all seeds were treated with a commercial pesticide (Acceleron in 2014 and Cruiser Max in 2015). In 2014, seeds other than the control were treated with the commercial *Trichoderma* product SABREX LQ (strains *T. afroharzianum* K2 and *T. atroviride* K4), with *Trichoderma atroviride* strain K5, with K5 plus *Bacillus amyloliquifaciens* strain As2, or with K5 alone. In 2015, the seeds were treated with SABREX LQ, with K5+As2, or with a formulation containing the metabolite 1-octen-3-ol. The adjuvants used in the K5As2 treatments differed between the treatments in 2014 and 2015. Plots were in randomized blocks with 4 replicates/treatment in 2014 and in 2015, in strip trials that were divided into 4 replicates per treatment. Full statistical analyses are presented in Table 3 using multiple comparisons of means using Dunnet contrasts. For comparisons within this Figure, bars representing standard deviations and lower case letters indicate levels of significance at P=0.10 are shown. Analyses compare only different treatments across specific hybrids and do not reflect differences between different hybrids. The two lower graphs provide the estimated total levels of C and N in plants produced with the different seed treatments. Within each year, there was no difference in the percentage of C or N in plants across treatments. The values shown represent the % C or N×the biomass of silage×an estimate of the contribution of the roots to the total biomass according to the following equation:

$$\text{Total C or N per hectare} = DW_S \times PRNorC \times RC_E,$$

Where:

$DW_S$ is the dry weight of silage per hectare per treatment.

PRNorC is the fractional proportion of C or N in the plant.

$RC_E$ is relative contribution of roots to the total biomass. Based on root tube experiments, the total biomass was estimated to be 1.88×the weight of the above ground silage for the control, 2×the weight with SABREX, 2.05×the weight with K5 and K5As2 and 2.1×the weight with OMEGA. In other words, the roots appeared to be proportionally larger than the shoots in the experiments described for the pipe experiments shown later.

In contrast to our expectations, the OMEGA treatment mixture enhanced plant growth and development for the entire growing season about as efficiently as the microbial mixtures when used alone.

The two microbial treatments differed from each other, the SABREX treatment contained no adjuvants, and only two strains of *T. afroharzianum*, while the K5+As2 was a mixture of *T. atroviride* strain K5+*B. amyloquifaciens* strain As2. Both stain mixtures were used in 2014, but the composition of the K5+As2 seed treatment differed between years: in 2014, the treatment was yeast extract plus humate, and in 2015, this strain mixture was applied in combination with the metabolite in the OMEGA formulation.

In this trial, hybrid 5245 was located in the lowest part of the field, and due to very heavy rains for about 3 weeks just after planting, this variety was flooded or submerged for these three weeks. Growth was substantially impeded, but after the flooding period, normal growth resumed. Throughout the season thereafter, visible differences were evident even as late as tasseling in terms of plant height, stalk diameter and leaf greenness (Table 2B). At harvest, grain yields were increased 23 to 44% in plants grown from treated seeds relative to the control, and silage yields were 46 to 85% more than the control. These substantial yield increases are at least partially due to rapid recovery from flooding stress by the biological or biorational treatments.

Figures 17A, 17B:
FIG. 17A depicts a photograph of the appearance of above ground and roots of hybrid 6490 from the field trial for which data is shown in FIGS. 14A-14D.
FIG. 17B depicts appearance of corn and ears from the corn in Illinois in the drought of 2012. Plants in the row on the left were grown with seeds treated with a commercial fungicide-insecticide mix with the same fungicide mix plus SABREX.
Figure 17C:
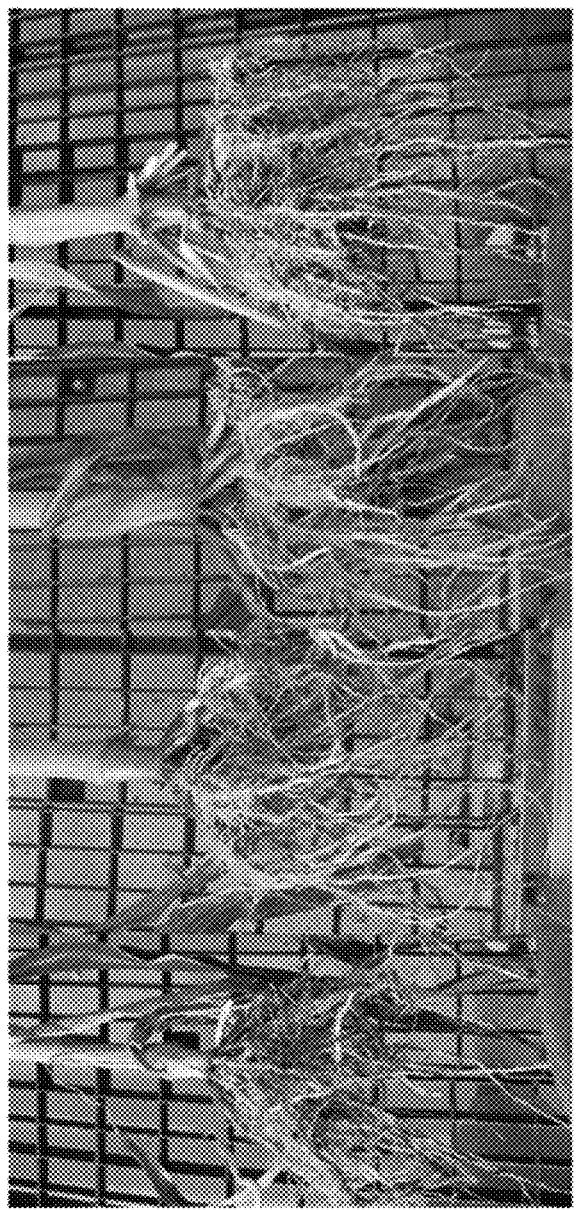
FIG. 17C depicts a photograph of the appearance of roots of hybrid 6490 from the field trial for which data is shown in FIGS. 14A-14D.

In both 2014 and 2015, increases in root mass were also noted (Table 8 and FIG. 17C). However, in field soil it was not possible to accurately quantitate these differences throughout the soil depth.

We determined the content of C, N, Ca, P, Mg, K and S in silage samples at the end of the 2014 and 2015 seasons (Table 4). The C and N contents measured here are in good agreement with published literature; corn stem tissue grown in Texas contained 43% C and 1.1% N and corn root tissue contained 43% N and 1.6% N (Zibilske and Materon 2005); values similar to those reported here.

Figure 14D:
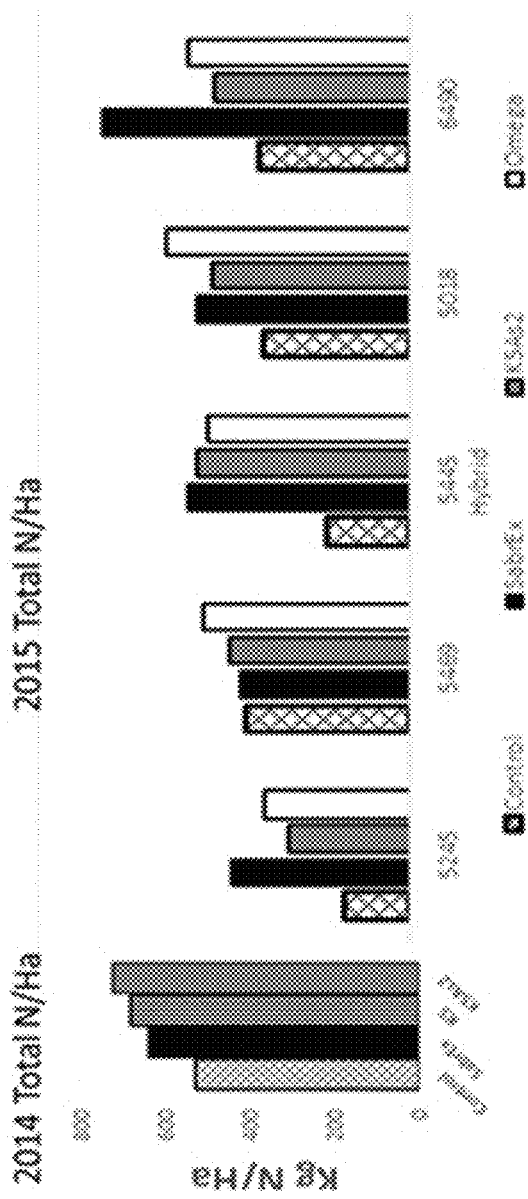

While there were no differences in any of these elements on a percentage basis, there was a sizable increase in the total quantity on a per hectare basis due to the increases in total biomass. Further, as noted in measurements in field trials (Table 5) not only was the above ground plant biomass greater, but roots were also larger (FIG. 17C). FIG. 14C and FIG. 14D provide the calculated total C and N contained with the plants when both roots and shoots are considered; methods and assumptions for calculating total biomass are given in Table 11.

TABLE 10

2014 Grain Yields

Multiple Comparisons of Means: Dunnett Contrasts
Fit: aov(formula = GrainYld.T.Ha.__twt ~ Treatment, data = d)
Linear Hypotheses:
    Estimate Std. Error t value Pr(>|t|)
K5 - Control == 0    2.4681 0.9674 2.551 0.0628 .
K5As2 - Control == 0 2.4707 0.9674 2.554 0.0628 .
SabrEx - Control == 0  1.2116  0.9674  1.252  0.4790
---
Signif. codes: 0 '*' 0.001 '' 0.01 '*' 0.05 '.' 0.1 ' ' 1
(Adjusted p values reported -- single-step method)
2014 Silage Yields
Fit: aov(formula = Silage..t.ha. ~ Treatment, data = d)
Linear Hypotheses:
    Estimate Std. Error t value Pr(>|t|)
K5 - Control == 0    17.853 5.956 2.997 0.02836 *
K5As2 - Control == 0 25.620 5.956 4.301 0.00256 **
SabrEx - Control == 0  13.726  5.956  2.304  0.09683 .
---
Signif. codes: 0 '*' 0.001 '' 0.01 '*' 0.05 '.' 0.1 ' ' 1
(Adjusted p values reported -- single-step method)
> test.dunnett = glht(aov.out, linfct=mcp(Treatment="Dunnett"))
> confint(test.dunnett)
2015 Grain Yields
Overall > my.aov<-aov(Yield__t.ha15pctMC ~ VAR + REP + TRT, data=d)
> summary(my.aov)

TABLE 10-continued

2014 Grain Yields

```
            Df Sum Sq Mean Sq F value   Pr(>F)
VAR          1  53.95   53.95  18.912 3.50e-05 ***
REP          1   0.29    0.29   0.102  0.75
TRT          4 103.04   25.76   9.029 3.31e-06 ***
Residuals   93 265.31    2.85
Signif. codes:  0 '***' 0.001 '**' 0.01 '*' 0.05 '.' 0.1 ' ' 1
5245

> my.aov<-aov(Yield_t.ha15pctMC ~ REP + TRT, data=v5018)
> summary(my.aov)
            Df Sum Sq Mean Sq F value Pr(>F)
REP          1  2.353   2.353   1.452 0.2482
TRT          4 23.396   5.849   3.608 0.0319 *
Residuals   14 22.693   1.621
Signif. codes:  0 '***' 0.001 '**' 0.01 '*' 0.05 '.' 0.1 ' ' 1
5469 my.aov<-aov(Yield_t.ha15pctMC ~ REP + TRT, data=v5469)
> summary(my.aov)
            Df Sum Sq Mean Sq F value Pr(>F)
REP          1  2.846   2.846   1.644 0.221
TRT          4 15.443   3.861   2.230 0.118
Residuals   14 24.240   1.731
5445

> my.aov<-aov(Yield_t.ha15pctMC ~ REP + TRT, data=v5445)
> summary(my.aov)
            Df Sum Sq Mean Sq F value Pr(>F)
REP          1  0.47   0.472   0.496 0.493
TRT          4 32.79   8.196   8.616 0.001 **
Residuals   14 13.32   0.951
5018

> my.aov<-aov(Yield_t.ha15pctMC ~ REP + TRT, data=v5018)
> summary(my.aov)
            Df Sum Sq Mean Sq F value Pr(>F)
REP          1  2.353   2.353   1.452 0.2482
TRT          4 23.396   5.849   3.608 0.0319 *
Residuals   14 22.693   1.621
6490 my.aov<-aov(Yield_t.ha15pctMC ~ REP + TRT, data=v6490)
> summary(my.aov)
            Df Sum Sq Mean Sq F value  Pr(>F)
REP          1  0.78   0.778   0.459 0.50936
TRT          4 37.44   9.361   5.517 0.00701 **
Residuals 14 23.75   1.697
Signif. codes:  0 '***' 0.001 '**' 0.01 '*' 0.05 '.' 0.1 ' ' 1
2015 Silage Yields
Overall aov.out = aov(revHaWT ~ TRT*VAR, data=d)
> summary(aov.out)
            Df Sum Sq Mean Sq F value   Pr(>F)
TRT          4  5754  1438.6   7.375 3.55e-05 ***
VAR          1  2326  2325.8  11.923 0.000851 ***
TRT:VAR      4  1613   403.3   2.067 0.091769 .
Residuals   89 17362   195.1
Signif. codes:  0 '***' 0.001 '**' 0.01 '*' 0.05 '.' 0.1 ' ' 1
By Hybrid
5245

Df Sum Sq Mean Sq F value  Pr(>F)
TRT          4  1831   457.8   5.666 0.00553 **
Residuals   15  1212    80.8
---
Signif. codes:  0 '***' 0.001 '**' 0.01 '*' 0.05 '.' 0.1 ' ' 1
Multiple Comparisons of Means: Dunnett Contrasts
Fit: aov(formula = revHaWT ~ TRT, data = d5245)
Linear Hypotheses:
                          Estimate Std. Error t value
K5As2 Omega - Control == 0   14.625      6.356   2.301
Omega - Control == 0         18.250      6.356   2.871
SabrExLQ - Control == 0      27.300      6.356   4.295
                          Pr(>|t|)
K5As2 Omega - Control == 0  0.11012
Omega - Control == 0        0.03782 *
SabrExLQ - Control == 0     0.00231 **
---
Signif. codes:  0 '***' 0.001 '**' 0.01 '*' 0.05 '.' 0.1 ' ' 1
(Adjusted p values reported -- single-step method)
5469 aov.out = aov(revHaWT ~ TRT, data=d5469)
> summary(aov.out)
            Df Sum Sq Mean Sq F value Pr(>F)
TRT          4  750.6   187.7   0.903  0.489
Residuals   14 2910.6   207.9
Multiple Comparisons of Means: Dunnett Contrasts
Fit: aov(formula = revHaWT ~ TRT, data = d5469)
Linear Hypotheses:
                          Estimate Std. Error t value
K5As2 Omega - Control == 0  -10.850     10.196  -1.064
Omega - Control == 0          5.217     11.012   0.474
SabrExLQ - Control == 0       2.725     10.196   0.267
                          Pr(>|t|)
K5As2 Omega - Control == 0  0.680
Omega - Control == 0        0.970
SabrExLQ - Control == 0     0.996
(Adjusted p values reported -- single-step method)
5445

> aov.out = aov(revHaWT ~ TRT, data=d5455)
> summary(aov.out)
            Df Sum Sq Mean Sq F value Pr(>F)
TRT          4   226   56.51   0.554  0.699
Residuals   15  1529  101.95
> lsd<-LSD.test(aov.out, "TRT", alpha=0.1)
> lsd
Multiple Comparisons of Means: Dunnett Contrasts
Fit: aov(formula = revHaWT ~ TRT, data = d5455)
Linear Hypotheses:
                          Estimate Std. Error t value
K5As2 Omega - Control == 0    8.350      7.140   1.170
Omega - Control == 0          8.400      7.140   1.177
SabrExLQ - Control == 0       8.850      7.140   1.240
                          Pr(>|t|)
K5As2 Omega - Control == 0  0.604
Omega - Control == 0        0.599
SabrExLQ - Control == 0     0.558
(Adjusted p values reported -- single-step method)
5018

> aov.out = aov(revHaWT ~ TRT, data=d5018)
> summary(aov.out)
            Df Sum Sq Mean Sq F value Pr(>F)
TRT          4  1820   455.1   2.302  0.106
Residuals   15  2966   197.7
> lsd<-LSD.test(aov.out, "TRT", alpha=0.1)
> lsd
$statistics
  Mean     CV    MSerror      LSD
64.075 21.94518 197.7222 17.43039
Multiple Comparisons of Means: Dunnett Contrasts
Fit: aov(formula = revHaWT ~ TRT, data = d5018)
Linear Hypotheses:
                          Estimate Std. Error t value
K5As2 Omega - Control == 0   19.375      9.943   1.949
Omega - Control == 0         23.050      9.943   2.318
SabrExLQ - Control == 0      24.025      9.943   2.416
                          Pr(>|t|)
K5As2 Omega - Control == 0  0.2022
Omega - Control == 0        0.1069
SabrExLQ - Control == 0     0.0894 .
---
Signif. codes:  0 '***' 0.001 '**' 0.01 '*' 0.05 '.' 0.1 ' ' 1
(Adjusted p values reported -- single-step method)
6490

> aov.out = aov(revHaWT ~ TRT, data=d6490)
> summary(aov.out)
```

TABLE 10-continued

2014 Grain Yields

|  | Df | Sum Sq | Mean Sq | F value | Pr(>F) |
|---|---|---|---|---|---|
| TRT | 4 | 5643 | 1410.8 | 9.029 | 0.00064 *** |
| Residuals | 15 | 2344 | 156.3 |  |  |

Signif. codes: 0 '*' 0.001 '' 0.01 '*' 0.05 '.' 0.1 ' ' 1
Multiple Comparisons of Means: Dunnett Contrasts
Fit: aov(formula = revHaWT ~ TRT, data = d6490)
Linear Hypotheses:

|  | Estimate | Std. Error | t value |
|---|---|---|---|
| K5As2 - Control == 0 | 15.200 | 8.839 | 1.720 |
| Omega - Control == 0 | 26.375 | 8.839 | 2.984 |

TABLE 10-continued

2014 Grain Yields

| SabrEx - Control == 0 | 47.000 | 8.839 | 5.317 |
|---|---|---|---|
| Pr(>|t|) |  |  |  |
| K5As2 - Control == 0 | 0.2910 |  |  |
| Omega - Control == 0 | 0.0305 * |  |  |
| SabrEx - Control == 0 | <0.001 *** |  |  |

Signif. codes: 0 '*' '' 0.001 '*' 0.01 '.' 0.05 0.1 ' ' 1
(Adjusted p values reported -- single-step method)

Field Trials, 2016. The field results on grain yields in 2015 were validated in 2016 across three of the same hybrids used in NY in 2015 (FIGS. 14A-D, FIGS. 15A-C and FIGS. 16A-C). In addition, we hypothesized that N fertilization levels might contribute to results and therefore tested N management systems that utilize the seed treatments described herein. Growing conditions in 2016 were nearly ideal and the trials were conducted in deep silty loam soils with good organic matter content. It should be noted that the K5 treatment differed from that in 2014 or 2015, in that for 2016 K5 was used alone with no other biological or adjuvant treatment.

All of the seed treatments resulted in greater yields than the control (FIGS. 15A-C and FIGS. 16A-C). The total yields for each variety across the different N levels are shown in the left panel. Since changes in yields are difficult to see in these graphs, the yield changes with each hybrid and treatment are shown in the right panel (FIG. 4). Overall differences in yields of all variables (treatment, hybrid and N level were highly significant (FIG. 4). The N fertility levels made a large difference; with the lowest level of N giving smaller and less uniform yields than the higher levels. As N increased, the error terms (see bars representing SD) decreased, and the seed treatments also decreased the error terms. Higher levels of variability were most notable at the lower N levels. Across all treatments and N levels, the yields were greater when treated seeds were used, with the only exception being with OMEGA at 336 kg N/ha. In many cases the yield increase was large, up to about 2.5 Kg/Ha. In general, the yield increases associated with OMEGA were greatest at the lower N levels.

Referring to FIGS. 15A-C and FIGS. 16A-C, shown are yields and yield increases of three cultivars of corn from field trials in Wisconsin in the presence of three different biological seed treatments, plus a control, and over four rates of nitrogen fertilizer. Each value is the mean across four replicates and the bars in the left hand set of graphs represent standard deviations. There were high levels of significance and numerous interactions.

TABLE 10 providing overall statistical analyses using Dunnett's contrasts follows:

| Variable | Df | Sum Sq | Mean Sq | F value | Pr(>F) |
|---|---|---|---|---|---|
| Treatment | 3 | 6981 | 2327 | 4.116 | 0.0075 ** |
| hybrid | 1 | 21176 | 21176 | 37.459 | 5.96e-09 *** |
| Nitrogen | 1 | 190618 | 190618 | 337.186 | <2e-16 *** |
| Replicate | 1 | 31 | 31 | 0.055 | 0.8150 |
| TRT:hybrid | 3 | 1594 | 531 | 0.940 | 0.4226 |
| TRT:Nitrogen | 3 | 1204 | 401 | 0.710 | 0.5474 |
| hybrid:Nitrogen | 1 | 1078 | 1078 | 1.907 | 0.1690 |
| TRT:hybrid:Nitrogen | 3 | 105 | 35 | 0.062 | 0.9797 |
| Residuals | 175 | 98931 | 565 |  |  |

Signif. codes: 0 '*' 0.001 '' 0.01 '*' 0.05 '.' 0.1 ' ' 1

Field observations. In Illinois in 2012 there was a severe drought, with widespread crop failure. Differences in drought susceptibility were obvious in the mature crop between fields that received the SABREX seed vs not (all receiving the standard chemical treatment). The seed treatment was applied several months before the drought became acute. These differences were observed as plant survival, in ear growth, and grain filling. Especially prominent was the degree of browning and apparent leaf death between the treatments (FIG. 17B).

Figure 15A:
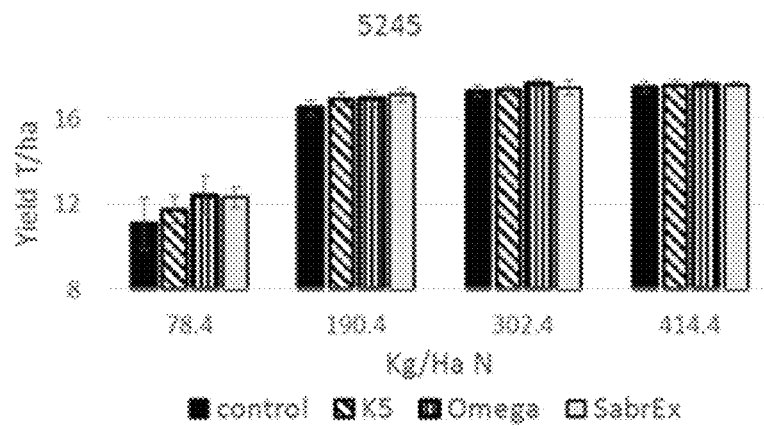
FIGS. 15A-15C depicts yields and yield increases of three cultivars of corn from field trials in Wisconsin in the presence of three different biological seed treatments, plus a control, and over four rates of nitrogen fertilizer. Each value is the mean across four replicates and the bars in the left hand set of graphs represent standard deviations.
Figure 15B:
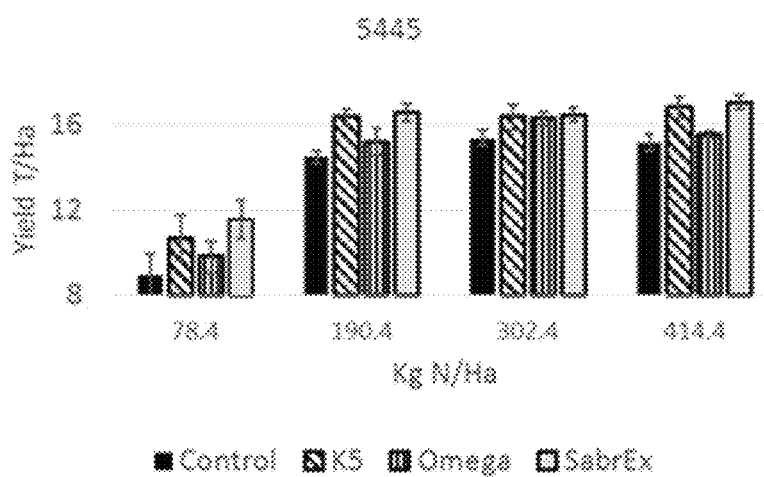
Figure 15C:
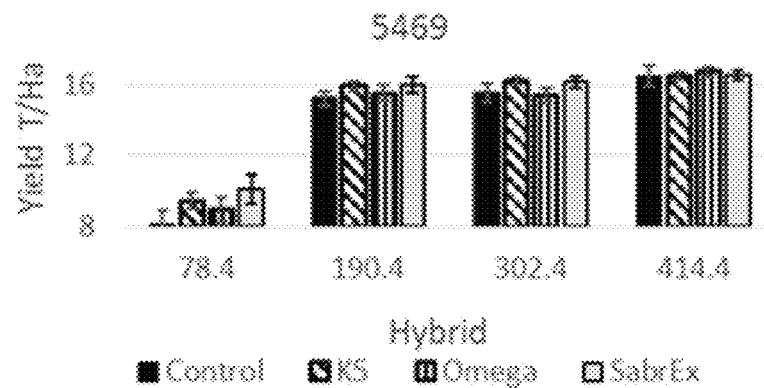
Figure 16A:
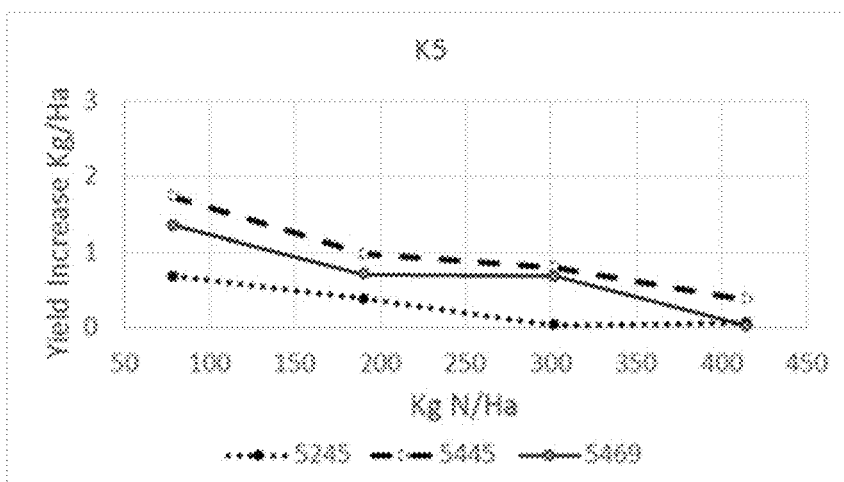
FIGS. 16A-16C depict linear data for yields and yield increases of three cultivars of corn from field trials in Wisconsin in the presence of three different biological seed treatments, plus a control, and over four rates of nitrogen fertilizer.
Figure 16B:
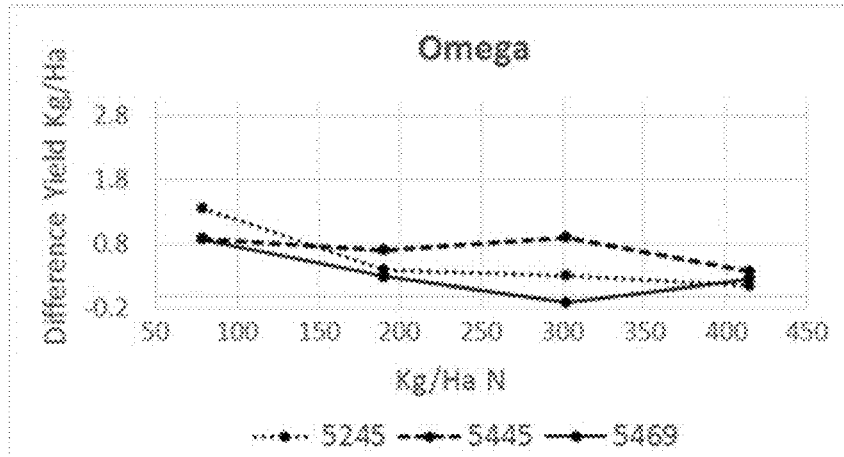
Figure 16C:
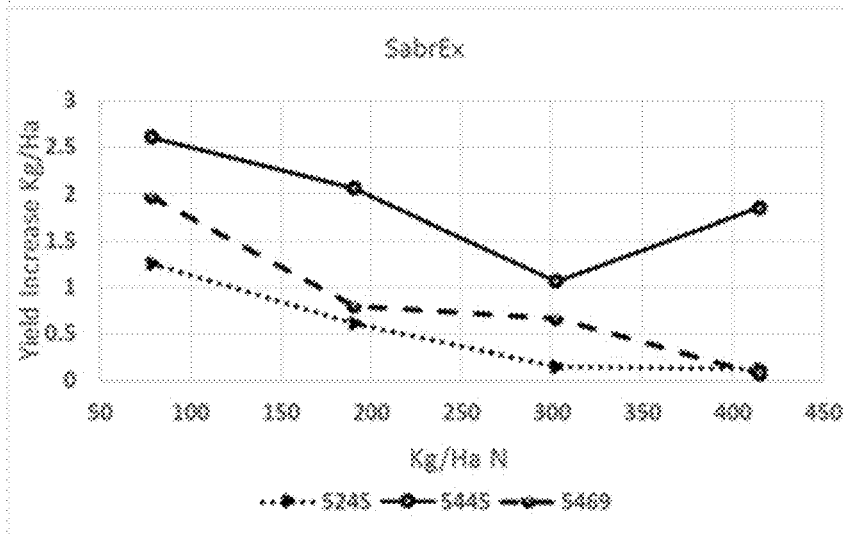

We also show visual presentations of plants from the 2015 trials. Both shoots and roots were substantially larger (FIG. 17A), and this is consistent with measured plant sizes in 2014 and 2015. Differences in plant sizes observed prior to tasseling may not be reflective of final plant sizes; with some plant types (grain vs dual purpose); early growth of plants may not translate as to biomass of silage (FIG. 15A-C).

Measurement of Root Sizes.

In field and greenhouse experiments, the seed treatments with the biological and biorational seed treatments described in this paper were observed to increase root growth (Table 8, FIG. 17C). However, it has been impossible to examine mature roots in detail when the plants are grown in the field. Therefore, the PVC pipe system was put in place wherein plants are grown in field soil but contained within the PVC pipes (20 cm diameter×178 cm long), with the pipes being buried to maintain appropriate soil temperatures. At the end of the season, the pipes were pulled from the ground, cut open to expose the roots and soil and the soil carefully washed away. Root lengths were substantially increased in plants grown from treated seeds (FIG. 17C), with up to a 2-fold increase in root biomass (fresh weight) with the K5 treatment. In other experiments (data not shown) a nonreplicated experiment was conducted similarly but the tubes were above ground and contained a transparent section through which root lengths could be measured visually. With this treatment, root elongation in the control treatments ceased about the time of tasseling, which with the treatments, root growth persisted until plant maturity and death.

We recognized that this is a somewhat artificial system, so in field grown plant plots we dug transects and, with a shovel removed soil to expose the root system. All of the treatments resulted in plants with larger root systems than the control; these single observations were conducted to validate the pipe experiments (FIG. 19).

Referring now to FIGS. 17A-C, illustrated are the appearance of above ground and roots of hybrid 6490 from the field trial for which data is shown; the above ground portions shown are from the same plants for each treatment. The treatments are the control (C), SABREX (S), K5As2 (K5As2) and OMEGA. The photographs were composites to group all treatments in the same Figure. The panel at right (C) shows appearance of corn and ears from the corn in Illinois in the drought of 2012. Plants in the row on the left were grown with seeds treated with a commercial fungicide-insecticide mix with the same fungicide mix plus SABREX.

Figure 18:
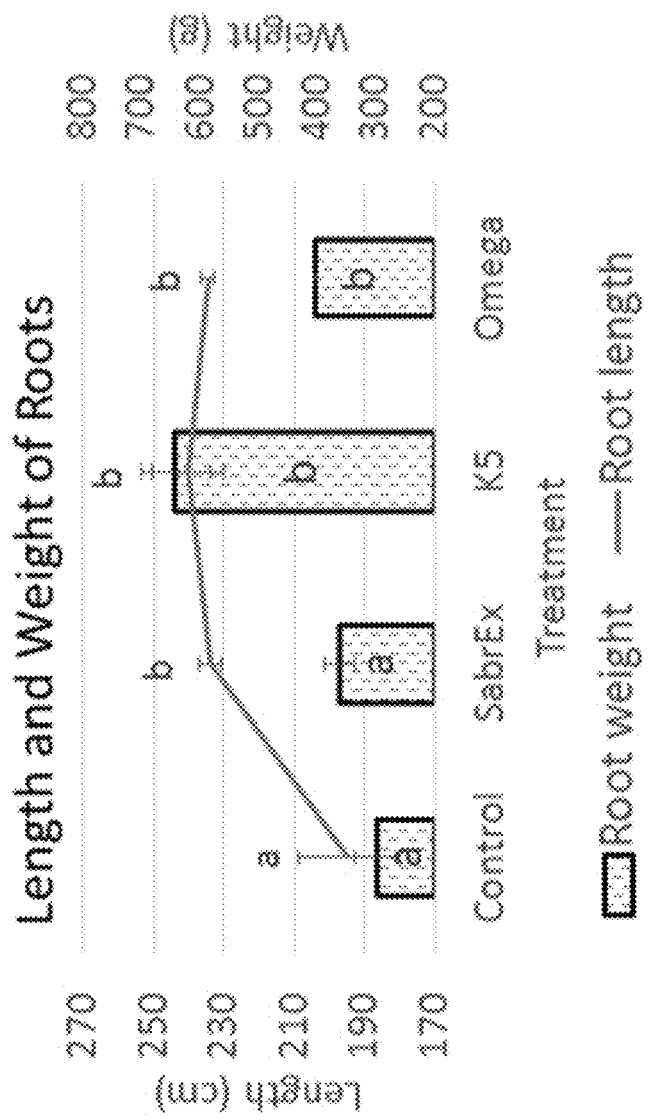
FIG. 18 depicts the lengths and fresh weights of roots of hybrid 5343 whose seeds were treated with the treatments shown and grown in PVC pipes 20 cm in diameter×214 cm long filled with field soil with adequate fertility and water. There were 3 or 4 replicates per treatment; bars shown reflect standard deviations, and lower case letters indicate statistical significance at $P=0.10$.

Turning now to FIG. 18, shown are the lengths and fresh weights of roots of hybrid 5343 whose seeds were treated with the treatments shown and grown in PVC pipes 20 cm in diameter×214 cm long filled with field soil with adequate fertility and water. There were 3 or 4 replicates per treatment; bars shown reflect standard deviations, and lower case letters indicate statistical significance at P=0.10. Root lengths of the more successful treatments completely filled the tubes from top to bottom. Note that in this experiment, seeds were treated with K5 alone and not K5As2 as in the previous experiments.

Figure 19:
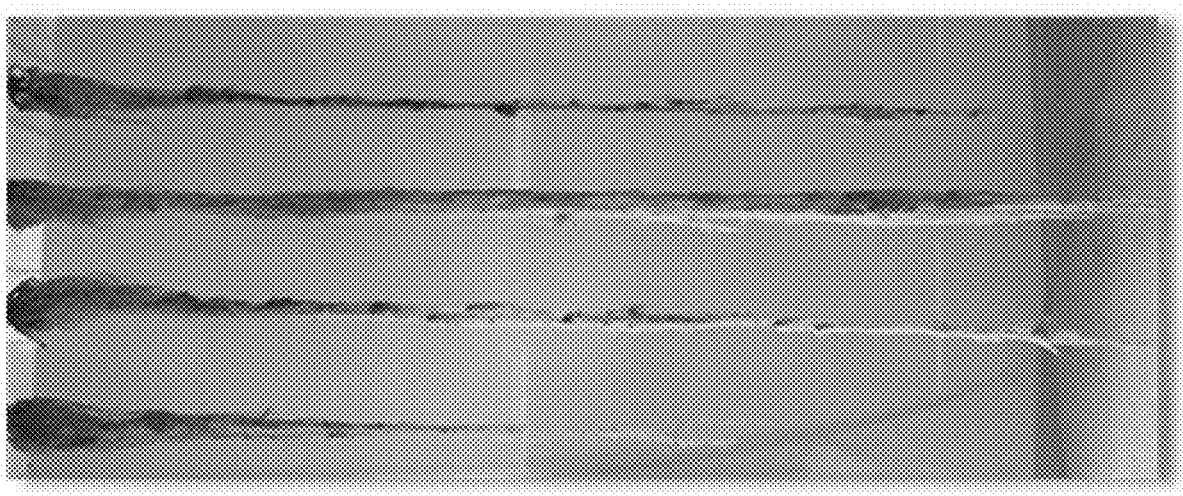
FIG. 19 depicts the appearance of individual roots that were part of the measurements in FIG. 18. The total length of the photograph is 289 cm; some roots in the tubes reached and exceeded the tube length

Referring to FIG. 19, there is shown the appearance of individual roots that were part of the measurements in FIG. 6A. Roots designated by C are control roots, S is from roots grown from SABREX treated seeds, K5 is from K5 treated seeds and O is from OMEGA treated seeds. The total length of the photograph is 289 cm; some roots in the tubes reached and exceeded the tube length.

Figure 20:
FIG. 20 depicts single observations of roots in field trials dealing with corn management. Corn of hybrid 6538 were grown in the field after seed treatments with no biological treatment (C), SABREX (S), K5As2 (K5As2) with no adjuvants, and OMEGA (O).
Figure 21C:
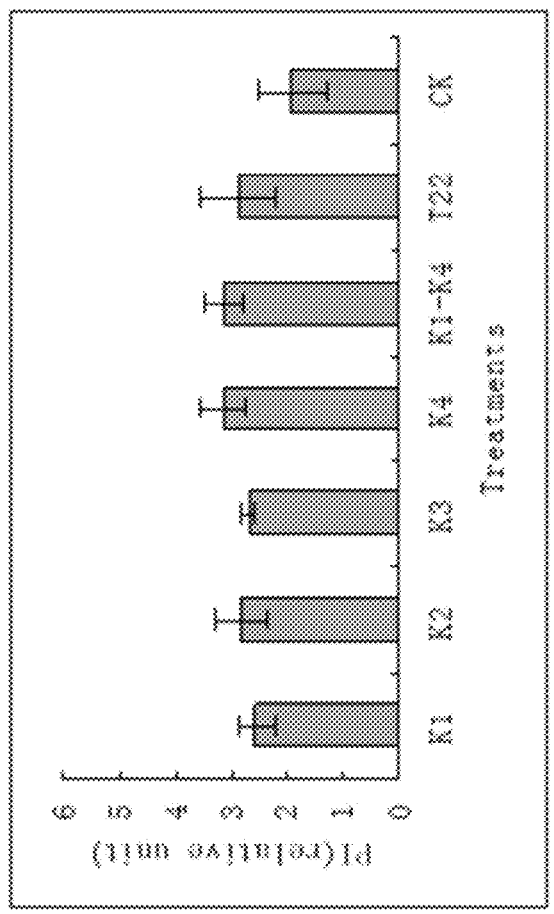
Figure 21D:
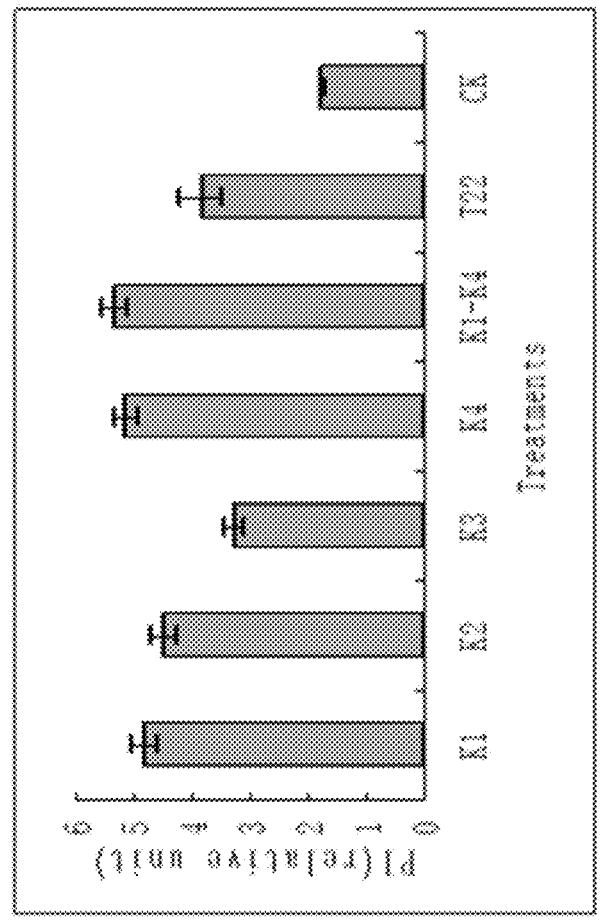

Now referring to FIG. 20, there is shown single observations of roots in field trials in 2016 that was part of a larger multilocation trial dealing with corn management. Corn of hybrid 6538 were grown in the field after seed treatments with no biological treatment (C), SABREX (S), K5As2 (K5As2) with no adjuvants, and OMEGA (O). These plots were exposed to very low moisture conditions from emergence through tasseling, with adequate moisture thereafter. The plots originally received 70 kg/ha N, and was side dressed 4 weeks after emergence with 370 kg/ha N. After plots were harvested, transverse trenches were dug and roots exposed on the vertical sides of the trench. Lengths of roots were measured from the ground surface to the longest visible root tip.

The embodiments set forth herein demonstrate that seed treatments with the microbial or biorational materials provided superior yields and possessed other useful qualities compared to plants without the treatments. All the plants within a single hybrid contain the same genome, but the holobionts produced from seeds with the microbial or biorational treatments provided differential responses to environmental conditions than the seeds treated only with standard seed treatment chemistries. Hereafter, the plants produced from biological or biorational treatments in this paper are described as Enhanced Holobionts (EH), and ones produced by different treatments are EH+the name of the treatment (e.g. EH SABREX OMEGA, etc). Advantages with the EH included increased shoot and root growth, higher yields, improved resistance to abiotic stresses, and enhanced photosynthetic capability (this latter attribute is discussed more fully later in this discussion). In 2014, induced resistance to disease was observed, and in recent work, nematode damage was less in the EH plots than controls (unpublished data by the authors). While the utility of EH treatments has been demonstrated in this work, their use and manipulation in the field environment may require the development of altered farm management practices. For example, in 2016, the yield increase as a percentage of the control was substantially less at higher N fertility levels than at lower ones. ABM has conducted several hundred commercial trials with SABREX over the past several years, yield advantages were observed about ⅔ of the time. While results described here are promising, it is likely that plants with advanced genetics that function efficiently with the microbial and biorational materials described in this paper can improve the results described here.

The results described herein are with strains selected over several decades that possess the critically important features of endophytic and rhizospheric competence. These strains rapidly colonized roots internally. They are contained within roots and do not proliferate in the above ground parts of the plants, including seeds and grain. The organisms can be efficiently and effectively applied as seed treatments, from which they become integrated into the plants and become a permanent part of the internal plant phytobiome. This then becomes a plant-microbe symbiont that results in enhanced plant growth and development.

Surprisingly, in view of the apparent advantages to the fungal components of this endophytic symbiosis, this seems a rare capability among *Trichoderma* strains. This is most convincingly demonstrated by the fact that these fungi are very prevalent in crop ecosystems around the world. The total numbers of these fungi in field soils outnumber the amount added by seed treatments described here several thousand-fold, yet the wild strains clearly do not enhance yields or take of advantage of the endophytic life style. If they did, the strains as added as seed treatments would be unlikely to provide the advantages we demonstrate since the native microflora would be at a competitive advantage and therefore control symbiosis-driven improvements in plant performance.

However, other strains of *Trichoderma* with endophytic capabilities are known as described in the introduction. A strain of *T. asperellum* was demonstrated to endophytically colonize cucumber roots and induce many of the advantages shown. Strain T22 of *T. harzianum* (now *T. afroharzianum*) colonized roots but not shoots of corn and induced resistance to foliar anthracnose, and a strain of *T. viride* that enhanced photosynthetic efficiency was limited to colonization of root cortices of plants. A strain of *T. asperellum* increased water use efficiency and photosynthesis in rice. These examples and the data included herein demonstrate that highly efficient root colonization and induction of systemic changes in plant physiology are strain specific and apparently have little relationship to species in which they are included.

Unexpected is the effect of the OMEGA biorational seed treatments that contain the fungal metabolite 1-octen-3-ol, yeast extract and humic acid (Leonardite shale). The metabolite was used at an extremely low concentration of 65 pL/seed. In the greenhouse we have tested higher concentrations, ranging from 200 to 20,000 pL in different formulations and consistently see plant growth promotive effects on seedling growth (data not shown). Humic acid was applied at 16 µg seed and the yeast extract 4 µg/seed. Thus the quantities applied are very small and cannot grow or proliferate on or in plants so their effects were expected to be transitory. However, as demonstrated in the field trials reported here, the effects were season-long in two different years in at two separate states under quite different environmental conditions. Not only was shoot growth (as evidenced by increases in silage) and grain yield improved but root length was increased as well.

Humic acid preparations, including Leonardite shale as used in this study, have been shown to increase plant growth and to enhance photosynthetic processes, however the low levels used seem unlikely to give long-term direct effects. Moreover, at least the yeast extract and the 1-octene-3-ol are readily degraded by microflora and the metabolite is volatile, so neither of these materials are likely to persist in the spermosphere for only very short periods of time. Even the metabolite persists in some form, as the plants grow, the concentration would be diluted to miniscule levels. These materials are exerting influences long after, and in plant parts, remote, from the time and site here they were applied. Thus, in the trials reported here, the effects were separated from the time of application/seed sowing both spatially and temporally. Another report indicates that *Trichoderma* metabolites increased disease resistance, antioxidant levels and plant growth in grape when the site of application was spatially distant from the site of the effect.

There are a number of possible explanations for these observations including alterations in chromatin structure leading to changes in plant gene expression involved in plant performance, or recruitment of additional rhizosphere inhabitants with the ability to enhance plant performance. In support of the latter hypothesis, we have assessed the microbiome from roots of plants from EH OMEGA, K5As2 and Sabrex. There were significant alterations in the microbial profiles of field-grown plants sampled at about tasseling (Ms in preparation). As regards the first hypothesis, various chemical plant elicitors of plant disease resistance have been shown to induce chromatin modifications. These changes result in histone modification patterns in the chromatin of defense genes that allow the genes to be fully and rapidly expressed when proper stimuli are present, resulting in reprogramming of plant gene expression. If this is the case with our systems, then the specific mode of action for the induction of scores of genes in the presence of our agents could be modification of plant chromatin, although other possibilities exist as well.

As is evident from embodiments set forth herein, different strains of *Trichoderma* or *Trichoderma* plus *Bacillus* also induce similar changes. Conceptually, it is somewhat easier to envision the effects of these microbes since at least the *Trichoderma* strains endophytically colonize and persist on and in the roots and produce signal molecules such as 1-octen-3-ol perceived by the plant component of the holobiont. This gives rise to the changes in plant phenotype that are indicated and are accompanied by changes in plant gene and protein expression. Given the magnitude of the plant responses demonstrated here, developing a highly reproducible system of implementation of the crop plant EH in commercial agriculture could be of enormous benefit in light of predicted changes in climate, world population, and arable land status.

The total C on per area basis was substantially increased in plants produced from seeds treated with the microbial and biorational treatments, even though in our trials and those of others (Zibilske and Materon 2005), mature corn contained a very constant 42-43% C. In one case (hybrid 6490) grown from seeds treated with EH K5As2, the total C per hectare was about doubled, although more modest increases were frequently noted. The source of this additional C is likely derived from C sequestration from the air. One critical feature of the improved EHs described herein logically include improved photosynthetic efficiency. Others have also reported significant increases in photosynthetic rates induced by treatment with other strains (Mastouri 2010; Vargas et al. 2009). All of the improved corn phenotypes described here, ranging from increased growth and root development to improved resistance to abiotic stresses and disease resistance, are energy requiring. In plants additional energy must come from enhanced levels of photosynthate. Thus, plants grown from seeds treated with any of the biological or biorational treatments must have improved abilities to enhance photosynthetic efficiency.

Photosynthetic efficiency is the fundamental upper limit on crop and one that has not been fundamentally improved by plant breeding efforts. As a consequence, the historically rapid advance in crop yields has slowed. The need to provide more food for the expected increase human population is critical, especially in the face of the expected increase biotic and abiotic stresses caused by global climate change.

However, recent advances in satellite-based remote sensing based on measurements of sun-induced chlorophyll fluorescence (SCIF) indicate that some of the most photosynthetically active regions on the planet are in the Corn Belt. The highly managed agricultural systems that have been developed there are based on plants bred for maximum yields and grown in an intensive fashion. The C incorporated into plants were estimated at >15 g C/m2/day or 150 kg C/ha/day. If this continued at that level for 60 days this would yield a total of 9.0 t C/ha/season (Guanter et al. 2014). Since corn typically grows for 90-120 days depending on hybrid, and the fact that clearly smaller or more senescent plants occupy the field at different times, this 9 t C/ha/season seems a useful rough number.

This compares reasonably well with typical corn biomass yields. Good, but not remarkably high, silage yields in the US Corn Belt are 25 tons/acre in the US. This is typically 30% dry matter, and with 42% C, this totals 7.062 t C/ha/season. Of course, this quantity represents only the above ground, harvested portion of the plant. The roots also contain about 42% C, and if the above and below ground plant biomasses are equal, then the total C fixed in one hectare of land would be approximately 14 t C/ha.

In this work, in the 2014 and 2015 field trials, we estimated that the level of C, in both above and below ground portions to be 13.5 t C/ha in the control plants, which is close to the values noted above and represented in FIGS. 14A-D (see Table 10 for methods of calculation). However, with the EH treatments, the total C estimated is higher (up to about 25 t C/ha at the highest level) in almost all cases than that of the control. Thus, the EH treatments gave a strong increase in C sequestered but differed according to the hybrid chosen, and are expected also to vary according to farm management practices as was evident in the effect of N fertilizer in the 2016 trials on grain yield.

Thus, that EH treatments increase photosynthetic efficiency was supported by these yield data, as was expected based on other work summarized herein.

Stresses of all types are primary impediments to optimized photosynthesis and maximum yield. Plants under stress overproduce reactive oxygen species (ROS) which are destructive to biomolecules. We suggest that the EH treatments induced plants to overcome the deleterious effects of ROS. Plants accumulate ROS through various mechanisms including over-excitation of photosynthetic efficiency in high light environments and as a consequence of stresses imposed through adverse abiotic and biotic environmental factors. In earlier work with tomatoes and *T. afroharzianum* strain T22, it was shown that drought, salt or even effects of low vigor seeds were largely overcome by upregulation of the pathways minimizing accumulation of harmful ROS (Mastouri et al. 2010, 2012); similar results have been described for other plant-*Trichoderma* combinations (Guler et al. 2016); and as summarized in FIG. 1. We hypothesize that, in that the presence of our organisms or metabolite, plants have higher throughput systems of antioxidant-mediated cycling of ROS and thereby attain a favorable internal redox environment At the same time, the EH treatments increased N and other nutrients in plants on a per hectare, but not on a percentage of total biomass, basis. The source of these nutrients, unlike C, must be derived from fertilizers or endogenous N in the soil. We hypothesize that this enhanced uptake is made possible by the deeper roots observed with the EH treatments and by the greater levels of photosynthate. These higher levels of photosynthate are surely required for the extra energy needed for uptake and utilization of nutrients that reside in the soil. Moreover, once nitrogen is taken up in the plant, it must be off-loaded into the tissues and converted into amino acids, nucleic acids and other C and N containing compounds, which again requires additional photosynthate, both to support plant physiology and as storage compounds. This greater total utilization of nitrogen and other compounds would be expected to reduce nitrate pollution in waterways, an effect that would be enhanced by the deeper roots that can intercept nitrate that otherwise might leach into waterways. Another source of pollution by nitrogen compounds is evolution of nitrous oxide into the atmosphere; at least one report indicates that nitrous oxide evolution is reduced by plants grown in the presence of *T. viride*. Changes in the microbial community structure around growing roots can markedly affect nitrous oxide generation. The combined effects directly of the microbes and on changes in associated root microflora that occurs with the EH plants should affect air and water pollution from nitrogenous compounds as well as to C levels.

There are substantial advantages to the enhanced accumulation of C in EH plants. Paustian et al (Paustian et al. 2016) estimate that a doubling of roots can result in a >5 t/ha/year increase in C incorporated into soil. This level of increase will enhance soil organic matter and sequester C to avoid this contribution to global climate change. One ton of C is equivalent to about 2.3 t of $CO_2$, so 5 t C in soil results in the removal of 11.9 t $CO_2$ from the atmosphere. Our data (from FIGS. 14A-D) estimate an increase in C levels in plants of 0 to 12 t total C; if 50% is in roots, the C levels that move into soil would equal 0 to 6 t/ha, and thus are consistent with the increases in root biomass in our root tube experiments (FIG. 18). If this C is incorporated into soil organic matter, this would also increase N that is contained within the soil; soil organic matter has a C:N ratio of about 10:1 (Paustian et al. 2016) so an increase in soil C, as soil organic content, also increases the carrying capacity of N in soil, and thereby minimizes water and air pollution. Deeper rooting also is anticipated to increase soil organic matter more than just enhanced root mass alone. Deeper soil layers typically contain less organic C than upper layers, and therefore have a greater capacity for C storage, and deeper soils are expected to metabolize C to $CO_2$ at a slower rate than occurs at upper layers since oxygen tensions typically are lower and there is less disturbance from cultivation systems. Worldwide, 25-50% increases in root C with moderate increases in deeper rooting could increase C stores in soil by 35-100 Mt/yr (Paustian et al. 2016) (equal to 80.5 to 230 Mt of atmospheric $CO_2$), and so can contribute significantly to reducing greenhouse gases contributing to global climate change (The total amount of increase of $CO_2$ in the atmosphere is about 16 GT annually (Committee on Geoengineering Climate 2015)) and of course can be continued over many years.

An increase in soil organic content is also necessary for maintenance and increasing soil productivity. Modern agricultural practices over time have resulted in a loss of 20 to 80 t/h of C as loss of soil organic matter (SOM), most of which was emitted into the atmosphere. Modern intensive agriculture including intensive corn culture, which is the primary focus of this paper, has contributed significantly to SOM loss. Losses in soil organic content (SOC) results in lower soil productivity; an increase in SOC of 1 t/ha can increase plant productivity on degraded soils of 1 to 40 kg/ha depending on the crop. Degraded soils have poorer structure (aggregation, bulk density, water infiltration and porosity), fertility, water holding capacity and lessened microbial diversity. Degradation of soils can be masked by fertilization and management practices, but is not sustainable. Increases in SOM contribute to agricultural productivity.

Corn is an obvious choice for improving C sequestration and consequent improvements in SOM since corn farming already provides the highest level of photosynthesis on the planet. However, limitations on the level of C sequestration and SOM exist regardless of the method of increasing root biomass. Soils have a maximum capacity for C sequestration. If C is continually added to soil, eventually there is a plateau where $CO_2$ emissions from oxidative processes equal the amount added. Where this equilibrium is established depends on many factors, including soil type and depth and tillage. Undisturbed soils maintained through minimum or other conservation tillage systems can allow C accumulation but deep plowing or other disruptive systems can result in rapid loss of soil C to the atmosphere.

This paper demonstrates that improved corn, including root phenotypes, occur in the EH plants. These are similar to those called for and suggested as urgent by several authors for the reasons just described. The obvious method for improving root phenotypes is plant breeding including genetic engineering of the plant, but clearly alteration of the plant root phytobiome can give rise to holobionts that are substantially improved for this characteristic. The EH plants are available now with no lag phase for selection and development of genetically altered plant genotypes.

However, there are obvious optimization steps that need to occur. First, it appears that not all corn hybrids respond equally; our data suggests that types adapted to dual purpose or silage only are likely to give the largest responses. There are undoubtedly pairings of specific plant genotype and microbial endophytes or metabolites that will give superior results to the untargeted selection of corn hybrids used in this work. This is undoubtedly true for other useful holobiont phenotypes including resistance to drought, stress, diseases and nematodes. Studies on the combination of optimization of microbe and plant genotype should provide rapid progress in development of superior products for modern agriculture. No doubt formulation of effective products is important. Formulation and possible microbial or metabolite combinations need to be pursued.

In summary, seeds treated with endophytic *Trichoderma* strains or formulations of the metabolite 1-octen-3-ol gave rise to EHs with improved characteristics. The *Trichoderma* strains colonized corn or soybean roots internally, and corn plants were larger, and at the end of season, gave increased yields of grain and silage. Root growth in particular was increased. Moreover, on a per hectare basis total crop C was increased, which strongly suggests an increase in photosynthetic efficiency. Total levels of other plant components such as N, P, K and Ca also were increased on a per acre basis. Further, the EH plants exhibited resistance to abiotic stresses such as flooding or water stress. Limited data in this work, plus other unpublished data support enhanced resistance to foliar diseases even though the beneficial fungi are present only in roots. These results, with both the endophytic fungi and the metabolite, are expected to result from changes in plant gene expression as shown in FIG. 1. Moreover, we recently have observed substantial shifts in the root microbiome as a consequence of the seed treatments (Ms in preparation). Thus, both endophytic symbiotic root colonizing agents and their metabolites substantially alter the phenotype at least the life of an annual crop. These EHs should be considered as improved crop plants that differ in their properties and advantages compared to plants without the holobiont modifications even though the genomes of plants are identical. Optimization of plant:microbe combinations, field management systems and microbial formulation all need to be done. However, the recent calls for plants with improved root phenotypes in crops such as corn to improve yields, enhanced soil organic matter and greater C sequestration to minimize global climate change can largely be met with the enhanced holobionts by changing the phytobiome, as described in this paper, without the time consuming and costly plant modification that would otherwise be required. Recently, a requirement for actual reduction of CO2 levels, rather than maintenance of current levels, has been suggested to avoid severe damage to the Earth ecosystems has been proposed since many of the effects of current GHG levels have slow reaction times. For such 'negative emissions' to be achieved, C scrubbing from the atmosphere by plant systems would be the least costly approach (Hansen et al. 2016). The corn-based system described here is clearly well suited to this need.

Corn and other crop yields are dependent upon conversion of sunlight into carbohydrates due to photosynthesis. Carbohydrates are then converted into proteins and all the other components of the plant, including grain or silage yield. The fundamental requirement for greater yields is photosynthesis.

Unfortunately, the basic yield of photosynthesis has not improved markedly over the years of breeding. Yields have increased, of course, due to improvements in the (a) abilities of plants to intercept light, and (b) the maximum distribution of the carbohydrate into the harvested portion of the plant. However, the fundamental resource, the ability of the photosynthesis machinery to more efficiently convert light energy into biomass energy has not increased.

This low level of conversion (about 20% under the most favorable conditions) is substantially reduced in the field. Even under good growing conditions, high light intensities over excite the photosynthetic pigments (primarily chlorophyll) and result in the production of reactive oxygen species (ROS). These ROS are damaging to the photosynthetic efficiency. High light reacting with plants is a little like leaving a battery on high charge for an extended period of time. Both cause a flow of electrons that can damage downstream systems. In plants, much of the excess electron flow reacts with oxygen in the air, and the resulting activated oxygen is very damaging. Consider what would happen if a corn field was sprayed with the ROS hydrogen peroxide; many of the immediate products of excess electron flow in plants are more toxic then hydrogen peroxide. The levels of ROS increase even more under stressful conditions. For example, under drought conditions, the levels of ROS increase to very damaging levels. This is a primary reason that drought stricken plants lose their green color and become tan—the ROS destroys and inactivates the photosynthetic apparatus.

In an exemplary embodiment superior microbes and formulation compositions are highly effective seed treatments. The microbes are selected for superior performance. They colonize plant roots and become functional parts of the plants. They are restricted to the outer layers of the root and do not colonize the above-ground parts of plants. They grow with the plant root system and result in season-long benefits to the plants. From their root location, they interact with the plant and induce system-wide changes in the plants' gene expression. In terms of photosynthesis, these system-wide changes include enhanced levels of the photosynthetic systems, so plants frequently are greener. In some studies, the levels of base photosynthesis in corn have increased 45%, which can be immediately used by the plant in providing the base for yield enhancement. Further, plants have enzyme systems that enhance degradation of ROS into nontoxic compounds. ABM's *Trichoderma* strains in SABREX and in the compositions of the present invention, provide resistance to drought, in large part by protecting the critical photosystems from ROS. Thus a high level of resistance to drought and other stresses is frequently seen.

Enhanced photosynthetic capabilities in plants grown from SABREX treated seeds provides sufficient carbohydrates to produce larger, healthier and more robust plants with larger root systems. These larger plants are more resistant to lodging and take up nutrients more effectively than ones from untreated seeds. No other microbial system is known to combine these advantages.

However, to attain greater grain yields, care must be taken to marry the right corn genetics with the microbial systems. Some corn lines provide ears of pre-determined size and these may be unable to grow sufficiently to take advantage of the greater carbohydrates produced by the more efficient photosynthesis systems of plants whose roots are colonized by elite strains. However, other varieties produce ears that are capable of a flexible response, i.e., able to use and continue to grow if adequate carbohydrates are available. The combination of the genetics in such elite *Trichoderma* strains and the best corn genetics makes a powerful synergistic combination for maximum yields and ROI for the grower.

As such, maximum plant photosynthetic efficiency has proven recalcitrant to improvement through conventional breeding systems, and is beginning to form an upper limit to efforts to improve plant performance and yield. Moreover, functional photosynthetic efficiency (FPE) is substantially less than the maximum because of obvious and nonobvious stress factors. Photosynthesis and photosynthesis machinery are highly susceptible to damage by reactive oxygen species (ROS). ROS can be produced under conditions of high light intensity (a nonobvious stress factor) and even more so, by obvious stresses such as drought. Conversely, beneficial fungi (*Trichoderma* spp.) colonize roots and increase basal levels of photosynthesis by at least 45%. Plants have redox cycling systems for the maintenance of optimal redox levels in plants. However, these cycling systems are usually insufficient to cope with the high levels of ROS that occur even under good field growing conditions, much less under high levels of stress such as drought. *Trichoderma* species induce coordinated upregulation of plant redox cycling enzymes that can maintain and improve plant productivity in the presence of both obvious and nonobvious stresses. This microbe-mediated system to maintain FPE permits greater productivity of plants in ways that have not been achieved through plant breeding and genetic improvement strategies used to date. Microbial agents that drive these effects are currently produced and available commercially. The capabilities of these strains create new opportunities to enhance plant productivity through plant genetics as well as through changes in agronomic practices. This improvement of FPE has applications in reduction of CO2 as a greenhouse gas.

All of the food we eat, and the oxygen in the air we breathe, is produced by energy from the sun. The conversion from sunlight to food and oxygen is via photosynthesis. Chlorophyll in plants (or in aquatic environments, algae and other organisms) is organized in special structures and catalyzes the splitting of CO2 into oxygen and carbon, with the carbon subsequently synthesized into sugars providing energy for plants. Ultimately, this same sugar is converted into all of the food that we consume. There is no other source for either food or oxygen. Photosynthesis is therefore the ultimate limiting factor in the growth of plants. Without adequate supplies of sugars, plants cannot grow. With adequate supplies of sugars and the materials that they are converted into, plants and all the organisms that depend upon them, from humans to bacteria, can grow and flourish.

Yield potential (YP) of crop plants can be approximated as the product of the solar radiation received over the unit of land in a single growing season (Q), the efficiencies of the plant to intercept the radiation (E1), conversion of radiation energy into biomass energy (E2), and partitioning of the biomass into the harvestable parts of the plants (E3) (YP=Q·E1·E2·E3) (Long, Marshall-Colon et al. 2015).

Modern developments in plant improvement, as exemplified by advances in the green revolution, have focused primarily on E1 and E3, while E2, a trait not easily evaluated in most breeding programs, has not been targeted. E1 is the proportion of available light intercepted by plant stands and is currently around 90%, while E3 has been improved by selecting varieties that convert more of their biomass into harvestable product rather than total biomass. For wheat, improvements in E3 were accomplished by dwarfed genotypes that reduced the amount of biomass allocated to the stem relative to that incorporated into the grain. For corn (maize) E3 was enhanced by genetically limiting the number of ears per plant to one, even though some plants had the potential to produce more ears/stalk or larger ears. The development of E3 strategies has been primarily to provide the greatest yields in plants where photosynthate is the primary limiting factor. For crops where maximum biomass is required, such as sugar cane and corn for silage, the need for improvement in E2 is particularly important. Further, if E2 was improved some of the standard dogmas of plant breeding—e.g., only one ear/stalk of corn, E3 strategies may be less desirable than is the cases currently.

Unfortunately, the best observed photosynthesis rates (E2) are only about 20% of the theoretical maximum and this has not noticeably improved through plant improvement efforts. To put it another way, yields have increased without improving the photosynthetic rate, which is the fundamental limiting factor. The rate of increase in yield improvements of major crops has decreased in recent years, in part because the other inputs and improvements are becoming limited by the lack of improvement in photosynthetic efficiency. Recently, ten approaches to increasing photosynthetic efficiency were proposed; all of them require complex transgenic engineering of the plant, including in some cases, actual modification of the plant structure relative to photosynthetically active sites.

This lack is even more acute because the E2 evaluation has been conducted under ideal conditions, but in the field, ideal conditions seldom, if ever, occur. Even small environmental variations may have effects. For example, one significant factor is related to the fact that maximum photosynthetic rates, relative to light inputs, occur at low light levels. When leaves are exposed to higher light levels, photosynthetic efficiency drops. This, in part, occurs because at high light levels, chlorophyll molecules remain highly excited and transfer excess energy to oxygen species, which in turn, produce reactive oxygen species (ROS) which are toxic and destructive. This results in damage to the basic photosynthetic machinery, including pigments, proteins and lipids, thus impairing the photosynthetic apparatus. This can be exacerbated by fluctuations in light levels, so even such apparently trivial factors as transient leaf shading by one leaf by another can result in damage to the photosynthetic apparatus and adversely affect photosynthesis. Photosynthetic systems (as well as other systems and pathway in plants) are further damaged by more serious stresses such as drought, salt and heat.

The performance index of barley photosynthesis (a measure that integrates several different aspects of photosynthesis) was reduced by 14 to 28% under mild and severe drought stress in a drought resistant cultivar and by 23 to 49% in the same two conditions in a susceptible cultivar. This reduction in measured photosynthesis was accompanied by decreases in chlorophyll content, carotenoid content and levels of the protein D1 in chloroplasts (these are critical pigments and a crucial structural protein in photosynthetic reaction centers, respectively). These changes also were associated with changes in stomatal conductance and CO2 assimilation rate, which are other critical measures of photosynthesis. All of these changes were indicative of drought-mediated damage to the photosynthetic systems in the drought affected plants. Resistant plants were more able to repair damage to these systems, a trait associated with higher levels of the plant antioxidant α-tocopherol that detoxifies ROS. Under conditions of stress, the levels of α-tocopherol increased in the resistant, but not the susceptible line.

This demonstrates that photosynthetic efficiency is one parameter of plant performance that has not been increased by plant breeding efforts, and that the upper limit for additional enhancement of plant yield will come closer and closer to the ceiling imposed by photosynthetic efficiency. Further, the functional photosynthetic efficiency (FPE), is negatively affected in the field. Even under good growing conditions, high light intensity or variable light intensity will saturate chlorophyll, giving rise to toxic and damaging levels of ROS. Other factors, such as drought stress, will further degrade photosynthetic efficiency and result in physical and chemical degradation of the entire photosynthetic system.

Management of the redox environment of the plant cell. Plant cellular health is determined in part by reduction/oxidation levels. Production of high levels of ROS causes the balance to shift to highly oxidized states that are damaging to cellular processes and that cause physical destruction of the cellular components and organelles that are essential to efficient operation of photosynthesis and other basic cellular systems within plants.

Plants contain a highly efficient cycling system to maintain proper redox levels in the cellular environment. These involve reducing (antioxidant) compounds including ascorbic acid and glutathione, along with other chemicals such as α-tocopherol. These compounds effectively reduce and detoxify ROS, but this results in the result of which is conversion of antioxidants to inactive, oxidized forms. Plants cells contain various biochemical pathways, such as the water-water cycle, the glutathione-ascorbate cycle, catalase, and superoxide dismutase. All of these pathways and enzymes have a similar function, which is to convert the oxidized forms of these antioxidants back to the reduced, active form. The result is systems whereby plant antioxidants repeatedly cycle between the reduced and active form. This is a strongly energy requiring process with a cost to the plant, but the faster the cycles process substrate, the more reduced antioxidant is available to the plant. The redox pathways are all known, and the genes that encode the necessary proteins also are known and understood.

Microbial modulation of the redox cycle. Certain microorganisms colonize plant roots internally and act as beneficial endophytes. These organisms, from their location within plant roots, produce chemical signals that act upon plant receptors that, in turn, give rise to plant signals that induce cascades of proteins that upregulate entire pathways. Among the pathways whose activities are increased are those involved in the redox pathways. The most prominent and well known are fungi in the genus *Trichoderma*, and several of these exist as commercial products (see iGET in www.abm1st.com). These strains have numerous benefits to plants, i.e., they increase plant growth (especially roots), enhance nutrient uptake efficiency, increase the levels of chlorophyll (plant greenness), and induce resistance to plant pathogens.

The increased growth and development must be associated with increased levels of photosynthesis in order to supply the energy for the various processes that we know are induced. This is substantiated by the data indicating that the plants colonized by such strains are frequently greener than ones without. In studies on another strain of *Trichoderma* uptake of $CO_2$ was increased by about 45% (Vargas, Mandawe et al. 2009), while in that and other studies, expression of proteins involved were shown to increase in the apparent absence of stress (Shoresh and Harman 2008).

This permits plants to grow bigger and produce overall higher yields of both harvestable products and total biomass.v It is an effect that has not been realized by many approaches to enhancing crop efficiency and the information presented above demonstrated that maximization of harvestable yield vs total biomass was a successful approach in plant breeding (Long, Marshall-Colon et al. 2015).

This greater level of photosynthesis is probably in part due to the greater level of total photosynthetic machinery (e.g, chlorophyll and critical proteins) as described in the preceding paragraph. Yet, in the field, optimization of FPE by modulation of the redox potential of the plants is probably even more important, since even nonobvious sources of stress such as very high light and light level changes can result in production of ROS induced by transitory overexcitement of chlorophyll.

Moreover, the beneficial fungi can optimize redox potential of plants and thereby enhance FPE under stresses such as drought. The presence of the beneficial microbes results in increased concentrations of redox cycling enzymes via up-regulation of the genes encoding these enzymes. The expression of these inducible changes is greater under stresses such as drought, just as was observed in the levels of α-tocopherol in barley resistant to drought. With plants colonized by *Trichoderma*, the levels of total antioxidants (ascorbic acid and glutathione) are not affected, but the ratio of reduced to oxidized forms is increased especially in the presence of drought (Mastouri, Bjorkman et al. 2012). Thus, the induction of genes that are involved in ROS elimination include entire pathways that are coordinately regulated according to the requirements of the plant.

In another embodiment, maximization of crop production strategies if FPE can be enhanced. In field trials with our best microbial inoculants on corn, plant yields were enhanced. With the composition of strains of the present invention, the biomass (silage yield) increased by about 50%, from 23 to 34 tons/acre, which is a 47% increase. Grain yield increased less, from 163 to 202 bu/acre, which is "only" a 24% yield increase. Both increases were statistically significant (P=0.10) and both were grown from seeds first treated with the recommended fungicides and insecticides. However, with the most effective microbial inoculant, two ears formed on most stalks, which did not occur frequently in the plants grown without the inoculants. However, at about the time of silking, the secondary ears aborted, so that the numbers of ears harvested was not affected. Beyond this, the ears that did form were large and completely filled, suggesting that, for the number of stalks at one ear/stalk, we were probably near the maximum grain yield potential for that variety at that plant density.

These results demonstrate that, in the plants grown with microbial inoculants, E3 deviated from the accepted norms since the biomass was substantially larger than with the control plants. This provided benefits in yield, especially in silage, where smaller plants optimized for resource partitioning into grain was less desirable. This suggests that we need to optimize growing conditions/plant genotypes to take maximum advantage of the opportunities that ABM's microbial inoculants provide. In particular, the ability of the strains to enhance FPE provides benefits that could not otherwise be realized.

With better photosynthetic efficiency, plants have more photosynthate, and therefore more energy, to produce biomass and final product. This suggests, for example, that a corn plant with the 3rd generation microbial strains, has the resources to produce more than one ear/plant, or larger ears, without diluting its photosynthate to a biomass energy level that is insufficient for this crop load. There are commercial maize genetics variants for ear genotype including flexible, fixed, determinant, indeterminate and prolific. Determinate and fixed ear types are limited in their response to environment. Flexible and/or indeterminate ear types, by contrast which can adjust to growing conditions by changes in ear size. Varieties or lines that can expand both numbers of rows of kernels and length according to environmental conditions are available.

Yields of corn were improved in all three growing seasons when yields were low, i.e., stresses on plants were greatest. The yield improvements decreased at medium yields and were low or nonexistent at the highest yields. Of course, this data was obtained using ABM's 2nd generation microbes and the 3rd generation products are expected to be more efficient across all yield ranges. Nonetheless, it appears that it may be that varieties with determinate size and yield were used in many cases, and so increases, even though enhanced photosynthate and crop development did not happen due to genetically imposed limits of corn variety. This would provide a ceiling on the possible increase in yields at the highest yield levels. If varieties with the capacity to increase yields when photosynthate levels permitted had been used, this apparent upper limit of yield improvement may not have occurred. In certain trials, the variety used was categorized as a "semi-flex." This means that it has some genetic capability to respond to higher levels of photosynthate and/or to overcome effects of low plant densities. However, it has lower capacity in these regards than the highest responding varieties.

CO2 sequestration and global greenhouse gases These discoveries have obvious implications for the management and reduction of greenhouse gases. As indicated above, CO2 sequestration as a result of induction by *Trichoderma* strains can be increased by 45%. This means that a crop plant growing with *Trichoderma* can remove much more CO2 from the atmosphere than one without. This is only a transitory change in annual plants so far as the above ground parts of the plants are concerned, since the fixed carbon will be released rapidly back to the atmosphere as the crops are consumed or otherwise used, and residues on the surface of the soil will rapidly decompose and release CO2 back into the air. However, *Trichoderma* colonization also results in greater root development, and carbon sequestered into root biomass is much longer lasting. The breakdown of root tissue is slower, but even when breakdown does occur, the sequestered carbon becomes part of the organic material in the soil. This increase in soil organic matter improves the soil and results in better soil tilth and yield potential. As a consequence, the soil becomes a sponge for long-term storage of carbon that otherwise would contribute to global climate change. The appendix provides data and pictures demonstrating the efficacy of the *Trichoderma*-based FPE system.

FIGS. 21A-D provide laboratory data demonstrating enhanced capabilities of tomatoes grown in the presence of elite *Trichoderma* strains in the absence of stress or under water deficit (soil moisture maintained at 60-70% of saturation) conditions.

FIGS. 21A-D show leaf greenness (due to different levels of chlorophyll) as measured with a Minolta SPAD meter in the presence and absence of mild drought conditions, and photosynthetic efficiency (performance index) as determined with a HansaTech Photosynthetic Efficiency Apparatus based on chlorophyll fluorescence kinetics. Note that both measures are greater in the presence of water deficit, suggesting enhanced activation of the ROS optimization apparatus and increased levels of antioxidant cycling. Conversely, in the absence of the strains, both chlorophyll content and photosynthetic efficiency are reduced by drought/water stress. Strains K1, K2, K3 and K4 are strains sold by ABM in its iGET systems, while T22 is an older strain of *Trichoderma*. See also FIG. 17B.

Figure 22:
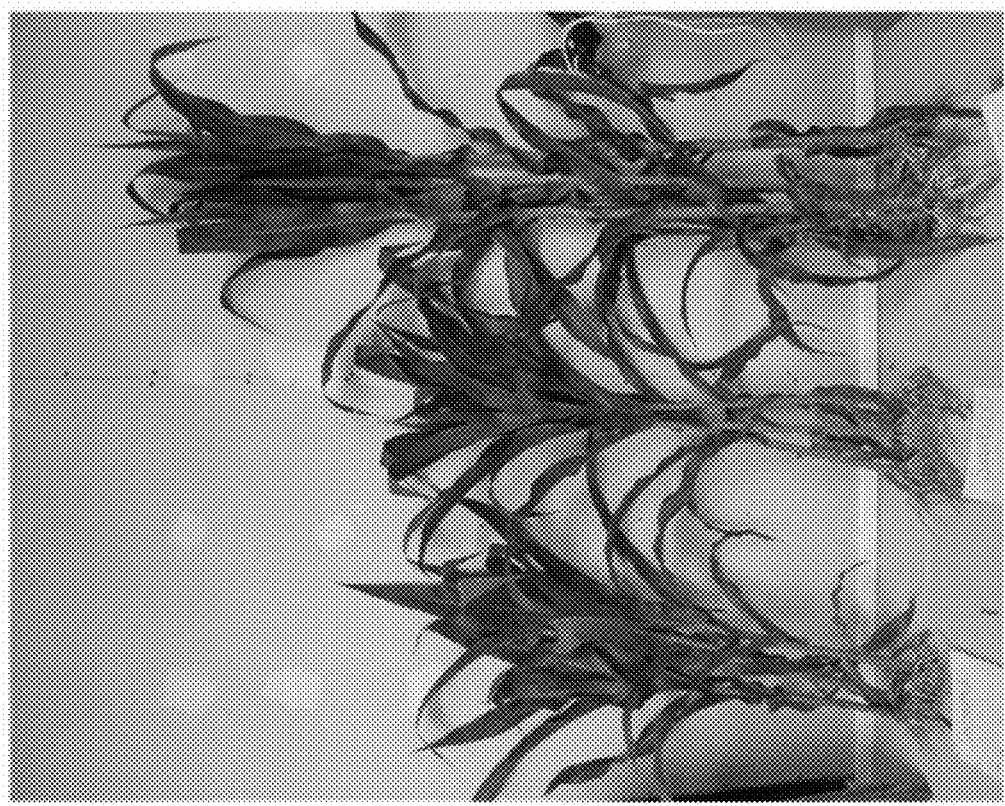
FIG. 22 depicts plants grown in the field in the presence and absence of *Trichoderma*, and that compares the control (left), treatment with the SABREX products (middle) and the treatments of the formulation of the present invention (right).

FIG. 22 shows photographs of plants grown in the field in the presence and absence of *Trichoderma*, and that compares the capabilities of ABM's current (2nd generation) SABREX products and the upcoming 3rd generation products. ABM believes that the capabilities induced by at least the 3rd generation plants could readily support and provide adequate photosynthate to support more than a single ear per plant. This would, in turn, result in greater yields and should maximize the benefits of these symbiotic *Trichoderma* and/ or mixtures of endophytic *Trichoderma* and *Bacillus* strains.

Therefore in an exemplary embodiment of the present invention, third generation formulations are provided comprising: (1) a symbiotic *Trichoderma* strain, such as: *Trichoderma viride* strain K5, *Trichoderma viride* strain NRRL B-50520, or *T. atroviride* strain WW10TC4; (2) a symbiotic *Bacillus* strain such as: *Bacillus amloliqofaciens* As1, As2, and/or As3; and (3) a metabolite such as 6-pentyl pyrone, harzianic acid, hydtra 1, harzinolide and 1-octene-3-ol. The third generation formulation may further comprise humic acids and lecithin associated with the metabolite.

In reference to test data associated with the third generation formulations set forth herein the following trial data presents measured yield data compared to the base (control) yields of several field trials (see Tables 11-14, wherein SABREX and EXCALIBRESA references represent various commercial products, OMEGA represents metabolite product alone, OMEGA CD represents a cyclodextrin encapsulated formulation of OMEGA, and various K5 references, including K5AS2 represents exemplary compositions of the present invention). In each of the field trials, yield was compared from base yields, which are considered the control variable. Least Statistical Difference (LSD) is set forth in Table 14 with regard to the various field trials.

TABLE 11

2018 Linden, IN, Field Trial for wheat varieties involving existing commercial products and products of the present invention.

| Exp. Num | Year | Crop/ Variety | Treatment | FORM | Yield | Yield Units | StdDev | TestWt | Yield (kg/ha) | Diff. from base (yld) | Diff. from base (%) |
|---|---|---|---|---|---|---|---|---|---|---|---|
| 3 | 2018 | Wheat/ FS 624 | Omega | LQ | 96.36 | bu/ac | 1.94 | 59.80 | 6464.26 | 1.14 | 1.19 |
| 3 | 2018 | Wheat/ FS 624 | K5AS2 + Omega | LQ | 95.28 | bu/ac | 1.80 | 59.70 | 6381.57 | 0.06 | 0.07 |
| 3 | 2018 | Wheat/ FS 624 | K5AS2 | LQ | 94.52 | bu/ac | 2.02 | 59.70 | 6330.32 | −0.70 | −0.74 |
| 3 | 2018 | Wheat/ FS 624 | Omega | LQ | 94.28 | bu/ac | 2.69 | 58.50 | 6187.43 | 4.03 | 4.46 |
| 3 | 2018 | Wheat/ FS 624 | SabrEx for Wheat | LQ | 93.26 | bu/ac | 1.92 | 59.60 | 6235.70 | −1.96 | −2.06 |
| 3 | 2018 | Wheat/ FS 624 | K5AS2 + Omega | LQ | 91.23 | bu/ac | 1.57 | 58.50 | 5987.32 | 0.98 | 1.08 |
| 3 | 2018 | Wheat/ FS 624 | K5AS2 | LQ | 88.57 | bu/ac | 2.10 | 58.60 | 5822.88 | −1.68 | −1.86 |
| 3 | 2018 | Wheat/ FS 624 | SabrEx for Wheat | LQ | 88.49 | bu/ac | 2.21 | 58.40 | 5797.78 | −1.76 | −1.95 |
| 3 | 2018 | Wheat/ Madsen | SabrEx for Wheat | | 87.98 | bu/ac | 1.91 | 58.80 | 5803.41 | −2.31 | −2.56 |
| 3 | 2018 | Wheat/ Madsen | SabrEx for Wheat | | 74.21 | bu/ac | 1.80 | 58.50 | 4870.39 | 2.59 | 3.62 |

TABLE 12

2018 Whitewater, WI, field trial for soybean varieties involving existing commercial products and products of the present invention.

| Exp. Num | Year | Crop/ Variety | Treatment | FORM | Yield | Yield Units | StdDev | TestWt | Yield (kg/ha) | Diff. from base (yld) | Diff. from base (%) |
|---|---|---|---|---|---|---|---|---|---|---|---|
| 5 | 2018 | Soybean | ExcalibreSA K1 + K5 | WP | 82.02 | bu/ac | 3.63 | 58.58 | 5389.93 | 6.27 | 8.27 |
| 5 | 2018 | Soybean | ExcalibreSA K5 | WP | 80.50 | bu/ac | 1.20 | 58.65 | 5296.82 | 4.75 | 6.26 |
| 5 | 2018 | Soybean | ExcalibreSA | WP | 78.94 | bu/ac | 3.55 | 58.50 | 5180.89 | 3.19 | 4.20 |

TABLE 13

2018 Harvard, IL, field trial for corn varieties involving existing commercial products and products of the present invention.

| Exp. Num | Year | Crop/ Variety | Treatment | FORM | Yield | Yield Units | StdDev | TestWt | Yield (kg/ha) | Diff. from base (yld) | Diff. from base (%) |
|---|---|---|---|---|---|---|---|---|---|---|---|
| 8 | 2018 | Corn | SabrEx for Corn In Furrow | LQ | 258.00 | bu/ac | 5.49 | 56.80 | 16440.15 | 14.00 | 5.74 |
| 8 | 2018 | Corn | Omega CD | LQ | 257.00 | bu/ac | 7.74 | 56.70 | 16347.59 | 13.00 | 5.33 |
| 8 | 2018 | Corn | SabrEx for Corn | LQ | 253.00 | bu/ac | 9.06 | 56.80 | 16121.54 | 9.00 | 3.69 |
| 8 | 2018 | Corn | SabrEx for Corn In Furrow | LQ | 222.00 | bu/ac | 4.66 | 57.40 | 14295.60 | 12.00 | 5.71 |
| 8 | 2018 | Corn | Omega CD | LQ | 219.00 | bu/ac | 8.51 | 57.40 | 14102.42 | 9.00 | 4.29 |
| 8 | 2018 | Corn | SabrEx for Corn | LQ | 211.00 | bu/ac | 5.88 | 57.40 | 13587.26 | 1.00 | 0.48 |

TABLE 14

Statistical data from field trials (Tables 11-13).

| Exp | Crop/ Variety | Location | LOC_avg | LOC_sd | LOC_t | LOC_pvalue | LOC_lsd | AltYLD_lsd |
|---|---|---|---|---|---|---|---|---|
| 3 | Wheat/ FS 624 | Whitewater WI 2.9OM | 58.5 | 0.207275 | 0.141256 | 0.988879 | 0.280368 | |
| 3 | Wheat/ FS 624 | Whitewater WI 5.1OM | 59.72857 | 0.135693 | 0.282609 | 0.938743 | 0.180082 | |
| 8 | Corn | Harvard IL | 57.4225 | 0.109749 | 1.598425 | 0.160786 | 0.123465 | 1.617109 |
| 5 | Soybean | Whitewater WI | 79.6 | 0 | 1.734064 | 0 | 3.327972 | 0 |
| 3 | Wheat/ Madsen | Whitewater WI 2.9OM | 89.1325 | 2.280587 | 2.488142 | 0.166 | 2.845689 | |
| 3 | Wheat/ Madsen | Whitewater WI 5.1OM | 72.91625 | 2.362867 | 3.127156 | 0.127 | 2.843274 | |

Those skilled in the art will recognize that the methods and compositions of the present invention may be implemented in many manners and as such are not to be limited by the foregoing exemplary embodiments and examples. In this regard, any number of the features of the different embodiments described herein may be combined into single or multiple embodiments, and alternate embodiments having fewer than, or more than, all of the features described herein are possible.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

DOCUMENTS INCORPORATED HEREIN BY REFERENCE

Adl, S. 2016. Rhizosphere, food security, and climate change: a critical role for plant-soil research. Rhizopshere 1:1-3.

Alfano, G., Lewis Ivey, M. L., Cakir, C., Bos, J. I. B., Miller, S. A., Madden, L. V., Kamoun, S., and Hoitink, H. A. J. 2007. Systemic modulation of gene expression in tomato by *Trichoderma harzianum* 382. Phytopathology 97:429-437.

Blaser, M. J., Cardon, Z. C., Cho, M. K., Dangl, J. L., Donohue, T. J., Green, J. L., Knight, R., Maxon, M. E., Northen, T. R., Pollard, K. S., and Brodie, E. L. 2016. Toward a predictive understanding of Earth's microbiomes to address 21st century challenges. mBio 7:e00714-00716.

Calvo, P., Watts, D. B., Kloepper, J. W., and Torbert, H. A. 2016. The influence of microbial-based inoculants on N2O emissions from soil planted with corn (*Zea mays* L.) under greenhouse conditions with different nitrogen fertilizer regimens. Canadian Journal of Microbiology 62:1041-1056.

Cawoy, H., Mariutto, M., Henry, G., Fisher, C., Vasilyeva, N., Thonart, P., Dommes, J., and Ongena, M. 2014. Plant Defense Stimulation by Natural Isolates of *Bacillus* Depends on Efficient Surfactin Production. Molecular Plant-Microbe Interactions 27:87-100.

Chaverri, P., Castlebury, L. A., Samuels, G. J., and Geiser, D. M. 2002. Multilocus phylogentic structure of *Trichoderma harzianum/Hypocrea lixii* complex. Molec. Phylogen. and Evol. Submitted.

Committee on Geoengineering Climate, B. o. A. S. a. C., Ocean Studies Board, National Research Council. 2015. Climate Intervention: Carbon Dioxide Removal and Reliable Sesquestration. National Academies Press, Washington D.C.

Djonovic, S., Pozo, M. J., Dangott, L. J., Howell, C. R., and Kenerley, C. M. 2006. Sm1, a proteinaceous elicitor secreted by the biocontrol fungus *Trichoderma virens* induces plant defense responses and systemic resistance. Molec. Plant Microbe Interact. 8:838-853.

Doni, F., Zaln, C. R. C. M., Isahak, A., Faturrahaman, F., Anhar, A., Mohamad, W., Yusoff, W. M. W., and Uphoff, N. 2017. A simple, efficient, and farmer-friendly *Trichoderma*-based biofertilizer evaluated with the SRI rice management system. Organic Agric. In press.

Ertani, A., Francioso, O., Tugnoli, V., Righi, V., and Nardi, S. 2011. Effect of Commercial Lignosulfonate-Humate on *Zea mays* L. Metabolism. Journal of Agricultural and Food Chemistry 59:11940-11948.

Feofilova, E. P. 2010. The fungal cell wall: Modern concepts of its composition and biological function. Microbiology 79:711-720.

Gopal, M., and Gupta, A. 2016. Microbiome selection could spur next-generation plant breeding strategies. Front. in Micrbiol. 7:1971.

Guanter, L., Zhang, Y., Jung, M., Joiner, J., Voigt, M., Berry, J. A., Frankenberg, C., Huete, A. R., Zarco-Tejada, P., Lee, J.-E., Moran, M. S., Ponce-Campos, G., Beer, C., Camps-Valls, G., Buchmann, N., Gianelle, D., Klumpp, K., Cescatti, A., Baker, J. M., and Griffis, T. J. 2014. Global and time-resolved monitoring of crop photosynthesis with chlorophyll fluorescence. Proceedings of the National Academy of Sciences of the United States of America 111:E1327-E1333.

Guler, N. S., Pehlivan, N., Karaoglu, S. A., Guzel, S., and Bozdeveci, A. 2016. *Trichoderma atroviride* ID20G inoculation ameliorates drought stress-induced damages by improving antioxidant defence in maize seedlings. Acta Physiologiae Plantarum 38:132.

Han, H. S., and Lee, K. D. 2005. Plant growth promoting rhizobacteria effects on antioxidant status, photosynthesis, mineral uptake and growth of lettuce under soil salinity. Res. J. Agric. Biol. Sci. 1:205-215.

Hansen, J., Satio, M., Kharecha, P., von Schukmann, K., Beerling, D. J., Cao, J., Marcott, S., Masson-Delmotte, V., Prather, M. J., Rohling, E. J., Shakun, J., and Smith, P. 2016. Young People's Burden: Requirement of negative CO2 emissions. Earth Syst. Dynamic. Discussion.

Harman, G. E. 2000. Myths and dogmas of biocontrol. Changes in perceptions derived from research on *Trichoderma harzianum* T-22. Plant Dis. 84:377-393.

Harman, G. E. 2014. *Trichoderma* strains that induce resistance to plant disease and/or increase plant growth. in: USPTO, USPTO, ed. Cornell University, USA.

Harman, G. E., and Lei, X. 2016. Highly efficient organic fertilizer and components thereof in: USPTO, USPTO, ed. Cornell University, USA.

Harman, G. E., Petzoldt, R., Comis, A., and Chen, J. 2004a. Interactions between *Trichoderma harzianum* strain vinT22 and maize inbred line Mo17 and effects of these interactions on diseases caused by *Pythium ultimum* and *Colletotrichum graminicola*. Phytopathology 94:147-153.

Harman, G. E., Howell, C. R., Viterbo, A., Chet, I., and Lorito, M. 2004b. *Trichoderma* species—opportunistic, avirulent plant symbionts. Nature Rev. Microbiol. 2:43-56.

Jaskiewicz, M., Conrath, U., and Peterhaensel, C. 2011. Chromatin modification acts as a memory for systemic acquired resistance in the plant stress response. EMBO Reports 12:50-55.

Kane, D. 2015. Carbon sequestration potential on agricultural lands: A review of current science and available practices. National Sustainable Agriculture Coalition, Breakthrough Strategies and Solutions LLC.

Kell, D. B. 2012. Large-scale sequestration of atmospheric carbon via plant roots in natural ecosystems: why and how. Philosophical Transactions of the Royal Society of London B Biological Sciences 367-1597:1589-1597.

Kogel, K. H., Achatz, B., Baltruschat, H., Becker, K., Deshmukh, S., Felle, H., Franken, P., Fodor, J., Gaupels, F., Harrach, B. D., Hueckelhoven, R., Neumann, C., and van Bel, A. 2003. Systemic activation of the antioxidant system in monocots is a significant feature of enhanced disease resistance and tolerance to abiotic stresses mediated by root endophytes. Free Radical Research 37:3-4.

Lal, R. 2004. Soil carbon sequestration impacts on global climate change and food security. Science 304:1623-1627.

Long, S. P., Marshall-Colon, A., and Zhu, X.-G. 2015. Meeting the global food demand of the future by engineering crop photosynthesis and yield potential. Cell 161:56-66.

Lorito, M., Woo, S. L., Harman, G. E., and Monte, E. 2010. Translational research on *Trichoderma*: from 'omics to the field. Annu. Rev. Phytopathol. 48:395-417.

Marra, R., Ambrosino, P., Carbone, V., Vinale, F., Woo, S. L., Ruocco, M., Ciliento, R., Lanzuise, S., Ferraioli, S., Soriente, I., Tuna, D., Fogliano, V., Scala, F., and Lorito, M. 2006. Study of the three-way interaction between *Trichoderma atroviride*, plant and fungal pathogens using a proteome approach. Curr. Genet. 50:307-321.

Mastouri, F. 2010. Use of *Trichoderma* spp. to improve plant performance under abiotic stress. PhD. Cornell University, Ithaca, N.Y.

Mastouri, F., Bjorkman, T., and Harman, G. E. 2010. Seed treatments with *Trichoderma harzianum* alleviate biotic, abiotic and physiological stresses in germinating seeds and seedlings. Phytopathology 100:1213-1221.

Mastouri, F., Bjorkman, T., and Harman, G. E. 2012. *Trichoderma harzianum* strain T22 enhances antioxidant defense of tomato seedlings and resistance to water deficit. Molec. Plant Microbe Interact. 25:1264-1271.

Mo, Y., Wang, Y., Yang, R., Zheng, J., Liu, C., Li, H., Ma, J., Zhang, Y., Wei, C., and Zhang, X. 2016. Regulation of plant growth, photosynthesis, antioxidation and osmosis by an arbuscular mycorrhizal fungus in watermelon seedlings under well-watered and drought conditions. Frontiers in Plant Science 7.

Morath, S. U., Hung, R., and Bennett, J. W. 2012. Fungal volatile organic compounds: A review with emphasis on their biotechnological potential. Fungal Biol. Rev. 26:73-83.

Nath, K., Jajoo, A., Poudyal, R. S., Timilsina, R., Park, Y. S., Aro, E.-M., G., N. H., and Lee, C.-H. 2013. Towards a critical understanding of the photosystem II repair mechanism and it regulation under stress conditions. FEBS Letters 587:3372-3381.

Pascale, A., Vinale, F., Manganiello, G., Nigro, M., Lanzuise, S., Ruocco, M., Marra, R., Lombardi, N., Woo, S. L., and Lorito, M. 2017. *Trichoderma* and its secondary metabolites improve yield and quality of grapes. Crop Protection 92:176-181.

Paustian, K., Campell, N., Dorich, C., Marx, E., and Swan, A. 2016. Assessment of potential greenhouse gas mitigation from changes to crop root management and architecture. Booz Allen Hamilton Inc., Washington D.C.

Samuels, G. J., and Hebbar, P. K. 2015. *Trichoderma*. Identification and Agricultural Properties. The American Phytopathological Society, St. Paul Minn.

Shoresh, M., and Harman, G. E. 2008a. The relationship between increased growth and resistance induced in plants by root colonizing microbes. Plant Signal. Behavior 3:737-739.

Shoresh, M., and Harman, G. E. 2008b. The molecular basis of maize responses to *Trichoderma harzianum* T22 inoculation: a proteomic approach. Plant Physiol. 147:2147-2163.

Shoresh, M., Mastouri, F., and Harman, G. E. 2010. Induced systemic resistance and plant responses to fungal biocontrol agents. Annu. Rev. Phytopathol. 48:21-43.

Thompson, K. A., Bent, E., Abalos, D., Wagner-Riddle, C., and Dunfleld, K. E. 2016. Soil microbial communities as potential regulators of in situ N20 fluxes in annual and perennial cropping systems. Soil Biology & Biochemistry 103:262-273.

Vargas, W. A., Mandawe, J. C., and Kenerley, C. M. 2009. Plant-derived sucrose is a key element in the symbiotic association between *Trichoderma virens* and maize plants. Plant Physiol 151:792-808.

Waller, F., Achatz, B., Baltruschat, H., Fodor, J., Becker, K., Fischer, M., Heier, T., Hueckelhoven, R., Neumann, C., von Wettstein, D., Franken, P., and Kogel, K.-H. 2005. The endophytic fungus *Piriformospora indica* reprograms barley to salt-stress tolerance, disease resistance, and higher yield. PNAS 102:13386-13391.

Xu, S., Fu, X., Ma, S., Bai, Z., Xiao, R., Li, Y., and Zhuang, G. 2014. Mitigating Nitrous Oxide Emissions from Tea Field Soil Using Bioaugmentation with a *Trichoderma viride* Biofertilizer. Scientific World Journal:793752.

Yedidia, I., Benhamou, N., and Chet, I. 1999. Induction of defense responses in cucumber plants (*Cucumis sativus* L.) by the biocontrol agent *Trichoderma harzianum*. Appl. Environ. Microbiol. 65:1061-1070.

Zachow, C., Berg, C., Mulller, H., Monk, J., and Berg, G. 2016. Endemic plants harbor specific *Trichoderma* communities with an exceptional potential for biocontrol of phtopathogens. J. Biotechnol. In press (http://dx.doi.org/10.1016/j.biotec.2016.03.049).

Zibilske, L. M., and Materon, L. A. 2005. Biochemical properties of decomposing cotton and corn stem and root residues. Soil Science Society of America Journal 69:378-386.

Djonovic, S., Pozo, M. J., Dangott, L. J., Howell, C. R., and Kenerley, C. M. 2006. Sm1, a proteinaceous elicitor secreted by the biocontrol fungus *Trichoderma virens* induces plant defense responses and systemic resistance. Molec. Plant Microbe Interact. 8:838-853.

Doni, F., Zaln, C. R. C. M., Isahak, A., Faturrahaman, F., Anhar, A., Mohamad, W., Yusoff, W. M. W., and Uphoff, N. 2017. A simple, efficient, and farmer-friendly *Trichoderma*-based biofertilizer evaluated with the SRI rice management system. Organic Agric. In press.

Guler, N. S., Pehlivan, N., Karaoglu, S. A., Guzel, S., and Bozdeveci, A. 2016. *Trichoderma atroviride* ID20G inoculation ameliorates drought stress-induced damages by improving antioxidant defence in maize seedlings. Acta Physiologiae Plantarum 38:132.

Harman, G. E., and Mastouri, F. 2010. Enhancing nitrogen use efficiency in wheat using *Trichoderma* seed inoculants. Page 4 in: Biology of Plant-Microbe Interactions, vol. 7. H. Antoun, T. Avis, L. Brisson, D. Prevost and M. Trepanier, eds. International Society for Plant-Microbe Intereactons, St. Paul, Minn.

Harman, G. E., Howell, C. R., Viterbo, A., Chet, I., and Lorito, M. 2004. *Trichoderma* species—opportunistic, avirulent plant symbionts. Nature Rev. Microbiol. 2:43-56.

Marra, R., Ambrosino, P., Carbone, V., Vinale, F., Woo, S. L., Ruocco, M., Ciliento, R., Lanzuise, S., Ferraioli, S., Soriente, I., Tuna, D., Fogliano, V., Scala, F., and Lorito, M. 2006. Study of the three-way interaction between *Trichoderma atroviride*, plant and fungal pathogens using a proteome approach. Curr. Genet. 50:307-321.

Mastouri, F., Bjorkman, T., and Harman, G. E. 2012. *Trichoderma harzianum* strain T22 enhances antioxidant defense of tomato seedlings and resistance to water deficit. Molec. Plant Microbe Interact. 25:1264-1271.

Shoresh, M., and Harman, G. E. 2008. The molecular basis of maize responses to *Trichoderma harzianum* T22 inoculation: a proteomic approach. Plant Physiol. 147:2147-2163.

Shoresh, M., Mastouri, F., and Harman, G. E. 2010. Induced systemic resistance and plant responses to fungal biocontrol agents. Annu. Rev. Phytopathol. 48:21-43.

Vargas, W. A., Mandawe, J. C., and Kenerley, C. M. 2009. Plant-derived sucrose is a key element in the symbiotic association between *Trichoderma virens* and maize plants. Plant Physiol 151:792-808.

Yedidia, I., Benhamou, N., and Chet, I. 1999. Induction of defense responses in cucumber plants (*Cucumis sativus* L.) by the biocontrol agent *Trichoderma harzianum*. Appl. Environ. Microbiol. 65:1061-1070.

The present disclosure contemplates that many changes and modifications may be made. Therefore, while the presently-preferred form of the system has been shown and described, and several modifications and alternatives discussed, persons skilled in this art will readily appreciate that various additional changes and modifications may be made without departing from the spirit of the disclosure, as defined and differentiated by the following claims.

What is claimed is:

1. A method of increasing the amount of carbon dioxide sequestration from the atmosphere by a plant, comprising the steps of:
   a) applying to a plurality of seeds of the plant a liquid suspension consisting of an amount of *Trichoderma viride* strain K5 (NRRL B-50520) and, optionally, a humic acid;
   b) wherein said amount of *Trichoderma viride* strain K5 (NRRL B-50520) applied in step (a) is sufficient to enhance photosynthetic efficiency of the plant; and
   (c) wherein said amount applied is sufficient to increase a root biomass of the plant, and wherein the increased carbon dioxide is sequestered in the increased root biomass of the plant.

2. The method of claim 1, wherein step (a) comprises applying a liquid suspension including a humic acid.

3. The method of claim 1, wherein step (a) comprises applying the liquid suspension of *Trichoderma viride* strain K5 (NRRL B-50520) to the plurality of seeds of the plant at a level of from $5.6 \times 10^8$ to $9 \times 10^8$ colony forming units per kilogram of seeds.

4. The method of claim 1, wherein the amount applied in step (a) is sufficient to enhance nitrogen utilization efficiency by said plant and to result in an increase in measured nitrogen in said plant.

5. The method of claim 1, wherein the amount applied in step (a) is sufficient to increase a crop yield of said plant.

6. The method of claim 1, wherein the plant is selected from the group consisting of alfalfa, rice, wheat, barley, oats, rye, cotton, sorghum, sunflower, peanut, potato, sweet potato, bean, pea, chicory, lettuce, endive, cabbage, brussels sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, maize, clover, sugarcane, *Arabidopsis thaliana*, *Saintpaulia*, petunia, pelargonium, poinsettia, chrysanthemum, carnation, zinnia, roses, snapdragon, geranium, lily, daylily, *Echinacea*, dahlia, hosta, tulip, daffodil, peony, phlox, herbs, ornamental shrubs, ornamental grasses, switchgrass, and turfgrass, or any other plant or seed or crop, or combinations thereof.

* * * * *